(12) United States Patent
Morrison

(10) Patent No.: US 10,975,158 B2
(45) Date of Patent: Apr. 13, 2021

(54) CD138-TARGETED INTERFERON DEMONSTRATES POTENT APOPTOTIC AND ANTI-TUMOR ACTIVITIES

(71) Applicant: The Regents of the University of California, Oakland, CA (US)

(72) Inventor: Sherie L. Morrison, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/789,828

(22) Filed: Oct. 20, 2017

(65) Prior Publication Data

US 2018/0162948 A1 Jun. 14, 2018

Related U.S. Application Data

(62) Division of application No. 14/649,888, filed as application No. PCT/US2013/073410 on Dec. 5, 2013, now Pat. No. 9,803,021.

(60) Provisional application No. 61/734,851, filed on Dec. 7, 2012.

(51) Int. Cl.
| | |
|---|---|
| C07K 16/28 | (2006.01) |
| C07K 14/56 | (2006.01) |
| A61K 38/21 | (2006.01) |
| A61K 39/395 | (2006.01) |
| A61K 45/06 | (2006.01) |
| C07K 16/30 | (2006.01) |
| A61K 39/00 | (2006.01) |
| A61K 38/00 | (2006.01) |
| A61P 35/00 | (2006.01) |
| C07K 14/565 | (2006.01) |
| C07K 14/57 | (2006.01) |

(52) U.S. Cl.
CPC ........ *C07K 16/2896* (2013.01); *A61K 38/212* (2013.01); *A61K 38/215* (2013.01); *A61K 38/217* (2013.01); *A61K 39/39558* (2013.01); *A61K 45/06* (2013.01); *C07K 14/56* (2013.01); *C07K 14/565* (2013.01); *C07K 14/57* (2013.01); *C07K 16/30* (2013.01); *A61K 38/00* (2013.01); *A61K 2039/505* (2013.01); *C07K 2317/56* (2013.01); *C07K 2317/565* (2013.01); *C07K 2317/622* (2013.01); *C07K 2317/73* (2013.01); *C07K 2319/00* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 5,696,237 A | 12/1997 | Fitzgerald et al. | |
| 5,824,782 A | 10/1998 | Hölzer et al. | |
| 5,980,895 A | 11/1999 | Pastan et al. | |
| 6,428,788 B1 | 8/2002 | Debinski et al. | |
| 6,800,735 B2 | 10/2004 | Whitty et al. | |
| 6,893,625 B1 | 5/2005 | Robinson et al. | |
| 7,005,498 B1 | 2/2006 | Steinaa et al. | |
| 7,151,164 B2 | 12/2006 | Hansen et al. | |
| 7,919,078 B2 | 4/2011 | Schreiber et al. | |
| 8,258,263 B2 * | 9/2012 | Morrison | A61K 38/212 530/351 |
| 8,563,692 B2 * | 10/2013 | Morrison | A61K 38/212 530/351 |
| 8,980,267 B2 * | 3/2015 | Grewal | C07K 16/18 424/134.1 |
| 9,139,634 B2 | 9/2015 | Morrison et al. | |
| 9,534,033 B2 * | 1/2017 | Morrison | A61K 38/212 |
| 9,803,021 B2 | 10/2017 | Morrison | |
| 10,093,745 B2 | 10/2018 | Morrison et al. | |
| 10,182,984 B2 | 1/2019 | Morrison et al. | |
| 10,822,427 B2 | 11/2020 | Morrison et al. | |
| 2002/0193569 A1 * | 12/2002 | Hanna | A61K 38/212 530/351 |
| 2003/0219433 A1 | 11/2003 | Hansen et al. | |
| 2004/0005647 A1 | 1/2004 | Denardo et al. | |
| 2005/0008649 A1 | 1/2005 | Shin et al. | |
| 2005/0079154 A1 | 4/2005 | Yarkoni et al. | |
| 2005/0232931 A1 | 10/2005 | Ma et al. | |
| 2006/0228300 A1 | 10/2006 | Chang et al. | |
| 2006/0263368 A1 | 11/2006 | Rosenblum et al. | |
| 2006/0287509 A1 | 12/2006 | Marks et al. | |

(Continued)

FOREIGN PATENT DOCUMENTS

| | | |
|---|---|---|
| CN | 1751122 A | 3/2006 |
| JP | 11-505132 A | 5/1999 |

(Continued)

OTHER PUBLICATIONS

Lesinski et al. Cancer Res. 68(20), pp. 6351-8360 (Year: 2008).*

(Continued)

*Primary Examiner* — Gary B Nickol
*Assistant Examiner* — Jegatheesan Seharaseyon
(74) *Attorney, Agent, or Firm* — Tom Hunter; Weaver Austin Villeneuve & Sampson LLP

(57) ABSTRACT

In various embodiments chimeric moieties (constructs) are provided that show significant efficacy against cancers. In certain embodiments the constructs comprise a targeting moiety that specifically binds CD138 attached to an interferon or to a mutant interferon. In certain embodiments, the constructs comprise anti-CD138 antibody attached to an interferon alpha (IFN-α) or to a mutant interferon alpha.

13 Claims, 35 Drawing Sheets

Specification includes a Sequence Listing.

(56) References Cited

U.S. PATENT DOCUMENTS

| | | | |
|---|---|---|---|
| 2008/0166319 A1 | 7/2008 | Schreiber et al. | |
| 2009/0169570 A1* | 7/2009 | Daelken | C07K 16/2896 424/179.1 |
| 2010/0047164 A1 | 2/2010 | Bigner et al. | |
| 2010/0172868 A1 | 7/2010 | Morrison et al. | |
| 2010/0297076 A1 | 11/2010 | Morrison et al. | |
| 2011/0104112 A1* | 5/2011 | Morrison | A61K 38/212 424/85.4 |
| 2011/0123554 A1* | 5/2011 | Osterroth | A61K 47/48276 424/178.1 |
| 2011/0165122 A1 | 7/2011 | Shahangian et al. | |
| 2011/0171229 A1 | 7/2011 | Ferrone et al. | |
| 2012/0237442 A1 | 9/2012 | Rossi et al. | |
| 2012/0258073 A1 | 10/2012 | Gerdes et al. | |
| 2014/0079668 A1 | 3/2014 | Morrison et al. | |
| 2016/0115239 A1 | 4/2016 | Morrison | |
| 2016/0115242 A1 | 4/2016 | Morrison et al. | |
| 2017/0151342 A1 | 6/2017 | Morrison et al. | |
| 2019/0135939 A1 | 5/2019 | Morrison et al. | |

FOREIGN PATENT DOCUMENTS

| | | | |
|---|---|---|---|
| JP | 11-513669 A | 11/1999 | |
| JP | 2003-508023 A | 3/2003 | |
| JP | 2003-535908 A | 12/2003 | |
| JP | 2004-93527 A | 3/2004 | |
| JP | 2004-528014 A | 9/2004 | |
| JP | 2005-520853 A | 7/2005 | |
| JP | 2006-500904 A | 1/2006 | |
| JP | 2008-505174 A | 2/2008 | |
| JP | 2009-511495 A | 3/2009 | |
| JP | 2010-540453 A | 12/2010 | |
| JP | 5591701 B2 | 9/2014 | |
| JP | 2015-515453 A | 5/2015 | |
| WO | WO 97/13529 A1 | 4/1997 | |
| WO | WO 97/24137 | 7/1997 | |
| WO | WO 01/03737 A1 | 1/2001 | |
| WO | WO 01/097844 A1 | 12/2001 | |
| WO | WO 02/46227 A2 | 6/2002 | |
| WO | WO 03/068821 A2 | 8/2003 | |
| WO | WO 2003/080106 A1 | 10/2003 | |
| WO | WO 2004/074486 A2 | 9/2004 | |
| WO | WO 2006/000448 A2 | 1/2006 | |
| WO | WO 2006/010891 A2 | 2/2006 | |
| WO | WO 2006/019447 A1 | 2/2006 | |
| WO | WO 2006/127757 A2 | 11/2006 | |
| WO | WO 2007/027106 A1 | 3/2007 | |
| WO | WO 2007/044616 A2 | 4/2007 | |
| WO | WO 2008/041014 A2 | 4/2008 | |
| WO | WO-2008041014 A2 * | 4/2008 | C07K 14/56 |
| WO | WO 2009/039409 A1 | 3/2009 | |
| WO | WO 2009/134870 A1 | 11/2009 | |
| WO | WO 2012/075324 A1 | 6/2012 | |
| WO | WO 2013/050725 A1 | 4/2013 | |
| WO | WO 2013/134138 A1 | 9/2013 | |
| WO | WO 2014/089354 A1 | 6/2014 | |
| WO | WO 2014/194100 A1 | 12/2014 | |

OTHER PUBLICATIONS

Vasuthasawat et al. Mabs, vol. 8(7), pp. 1386-1397 (Year: 2016).*
Von Strandmann et al. 2006 (Blood 107(5):1955-1962 (Year: 2006).*
Vasuthasawat et al., Targeted immunotherapy using anti-CD138-interferon a fusion proteins and bortezomib results in synergistic protection against multiple myeloma. Mabs (2016), vol. 8(7), pp. 1386-1397. (Year: 2016).*
Trinh et al., Synergistic Inhibition of Multiple Myeloma Growth by Anti-CD138-Interferon-alpha14 Fusion Protein and Lenalidomide. J. Mol. Immunology (2018), vol. 3 (1). pp. 1-9. (Year: 2018).*
U.S. Office Action [Requirement for Restriction/Election] dated May 13, 2016 issued in U.S. Appl. No. 14/649,888.
U.S. Office Action dated Oct. 3, 2016 issued in U.S. Appl. No. 14/649,888.
U.S. Notice of Allowance dated Jun. 16, 2017 issued in U.S. Appl. No. 14/649,888.
U.S. Office Action [Requirement for Restriction/Election] dated Mar. 10, 2011 issued in U.S. Appl. No. 12/678,981.
U.S. Office Action dated Jul. 5, 2011 issued in U.S. Appl. No. 12/678,981.
U.S. Office Action dated Jun. 14, 2012 issued in U.S. Appl. No. 12/678,981.
U.S. Final Office Action dated Mar. 26, 2013 issued in U.S. Appl. No. 12/678,981.
U.S. Office Action dated Jun. 17, 2014 issued in U.S. Appl. No. 12/678,981.
U.S. Ex Parte Quayle Action dated Mar. 3, 2015 issued in U.S. Appl. No. 12/678,981.
U.S. Notice of Allowance dated May 14, 2015 issued in U.S. Appl. No. 12/678,981.
U.S. Office Action dated Feb. 1, 2011 issued in U.S. Appl. No. 12/650,329.
U.S. Office Action dated Aug. 8, 2011 issued in U.S. Appl. No. 12/650,329.
U.S. Final Office Action dated Apr. 30, 2012 issued in U.S. Appl. No. 12/650,329.
U.S. Notice of Allowance dated Jun. 18, 2012 issued in U.S. Appl. No. 12/650,329.
U.S. Office Action dated Jul. 6, 2012 issued in U.S. Appl. No. 12/985,122.
U.S. Final Office Action dated Apr. 2, 2013 issued in U.S. Appl. No. 12/985,122.
U.S. Notice of Allowance dated Aug. 9, 2013 issued in U.S. Appl. No. 12/985,122.
U.S. Office Action dated Mar. 19, 2015 issued in U.S. Appl. No. 14/015,838.
U.S. Final Office Action dated Dec. 18, 2015 issued in U.S. Appl. No. 14/015,838.
U.S. Notice of Allowance dated Aug. 24, 2016 issued in U.S. Appl. No. 14/015,838.
U.S. Office Action dated Oct. 2, 2017 issued in U.S. Appl. No. 15/359,456.
U.S. Office Action dated Aug. 10, 2017 issued in U.S. Appl. No. 14/893,912.
PCT International Search Report and Written Opinion dated Mar. 18, 2014 issued in PCT/US2013/073410.
PCT International Preliminary Report on Patentability and Written Opinion dated Jun. 18, 2015 issued in PCT/US2013/073410.
PCT International Search Report and Written Opinion dated Jan. 12, 2009 issued in PCT/US08/77074 (WO2009/039409).
PCT International Preliminary Report on Patentability dated Mar. 24, 2010 issued in PCT/US08/77074 (WO2009/039409).
PCT International Search Report and Written Opinion dated Oct. 1, 2014 issued in PCT/US2014/040036.
PCT International Report on Patentability and Written Opinion dated Dec. 10, 2015 issued in PCT/US2014/040036.
Australian Office Action dated Feb. 26, 2013 issued in 2008302111.
Canadian Examiner's Report dated Feb. 4, 2015 issued in 2,699,944.
Canadian Examiner's Report dated Mar. 10, 2016 issued in 2,699,944.
Canadian Examiner's Report dated Nov. 22, 2016 issued in 2,699,944.
Chinese First Office Action dated May 2, 2012 issued in CN200880117225.8.
Chinese Second Office Action dated Feb. 4, 2013 issued in CN200880117225.8.
Chinese Third Office Action dated Jul. 15, 2013 issued in CN200880117225.8.
Chinese Final Rejection dated Jan. 6, 2014 issued in CN200880117225.8.
Chinese First Office Action dated Jul. 17, 2015 issued in CN201410160383.9.
Chinese Second Office Action dated Jun. 6, 2016 issued in CN201410160383.9.
Chinese Third Office Action dated Feb. 16, 2017 issued in CN201410160383.9.
European Extended Search Report dated Apr. 26, 2012 issued in EP08831632.8.

(56) References Cited

OTHER PUBLICATIONS

European Office Action dated Feb. 8, 2013 issued in EP08831632.8.
European Summons to attend Oral Proceedings dated Oct. 14, 2013 issued in EP08831632.8.
European Response [EP Summons to attend Oral Proceedings dated Oct. 14, 2013] dated Jan. 7, 2014 for EP08831632.8.
European Findings upon submission relating to Oral Proceedings dated Jan. 13, 2014 issued in EP08831632.8.
European Brief Communication [regarding the Oral Proceedings of Mar. 13, 2014] dated Jan. 16, 2014 issued in EP08831632.8.
European Written Submission [response to Communication of Jan. 16, 2014] dated Jan. 29, 2014 issued in EP08831632.8.
European Findings upon submission relating to Oral Proceedings dated Feb. 10, 2014 issued in EP08831632.8.
European Notification relating to Oral Proceedings dated Feb. 13, 2014 issued in EP08831632.8.
European Communication regarding Intention to Grant dated Mar. 4, 2014 issued in EP08831632.8.
European Communication regarding Intention to Grant dated Oct. 2, 2014 issued in EP08831632.8.
European Communication regarding Decision to Grant dated Jan. 15, 2015 issued in EP08831632.8.
European Extended Search Report dated Feb. 26, 2015 issued in EP 14 180 412.0.
European Office Action dated Dec. 11, 2015 issued in EP 14 180 412.0.
European Reply to Communication from Examining Division dated Mar. 29, 2016 for EP 14 180 412.0.
European Intention to Grant dated Jun. 24, 2016 issued in EP 14 180 412.0.
European Decision to Grant dated Nov. 10, 2016 issued in EP 14 180 412.0.
European Extended Search Report dated Feb. 24, 2017 issued in EP 16 19 5608.1.
European Office Action dated Nov. 29, 2017 issued in EP 16 19 5608.1.
Israeli Office Action dated Apr. 5, 2012 issued in IL-204644.
Israeli Office Action dated Apr. 17, 2013 issued in IL-204644.
Israeli Office Action dated Apr. 19, 2015 issued in IL-233305.
Israeli Office Action dated Nov. 24, 2016 issued in IL-233305.
Indian Office Action dated Dec. 30, 2016 issued in IN-1404/KOLNP/2010.
Indian Office Action (Hearing Notice) dated Nov. 29, 2017 issued in IN-1404/KOLNP/2010.
Japanese Office Action dated Jan. 29, 2013 issued in JP 2010-526011.
Japanese Final Office Action dated Mar. 10, 2014 issued in JP 2010-526011.
Japanese First Office Action dated Jul. 6, 2015 issued in JP 2014-154820.
Japanese Second Office Action dated Jul. 4, 2016 issued in JP 2014-154820.
Japanese Notice of Allowance [No Translation] dated Jan. 4, 2017 issued in JP 2014-154820.
Japanese First Office Action dated Jul. 31, 2017 issued in JP 2016-215048.
Korean Office Action dated Mar. 27, 2015 issued in KR 2010-7008737.
Korean Final Rejection dated Feb. 25, 2016 issued in KR 2010-7008737.
Korean Office Action dated Jun. 21, 2016 issued in KR 2016-7014105.
Mexican Office Action [No translation] dated May 7, 2013 issued in MX/a/2010/003099.
Mexican Office Action [No translation] dated Feb. 12, 2014 issued in MX/a/2010/003099.
Mexican Office Action [brief description in English] dated Apr. 25, 2016 issued in MX/a/2014/010567.
Mexican Second Office Action [No translation] dated Nov. 10, 2016 issued in MX/a/2014/010567.

NCBI, GenBank accession No. CAP17327.1, "interferon gamma [*Homo sapiens*]", (Oct. 15, 2008), 2pp.
Alfthan et al. (1995) "Properties of a single-chain antibody containing different linker peptides," *Protein Engineering* 8(7):725-731.
Arai et al. (Aug. 2001) "Design of the linkers which effectively separate domains of a bifunctional fusion protein," *Protein Engineering*, 14(8):529-532.
Bai et al. (Sep. 2006) "Improving the oral efficacy of recombinant granulocyte colony stimulating factor and transferrin fusion protein by spacer optimization," *Pharmaceutical Research*, 23(9):2116-2121.
Berger et al. (2002) "Licensure of Gemtuzumab Ozogamicin for the Treatment of Selected Patients 60 Years of Age or Older with Acute Myeloid Leukemia in First Relapse," *Invest. New Drugs*, 20(4):395-406.
Bird et al. (1988) "Single-Chain Antigen-Binding Proteins," *Science*, 242:423-426.
Bosly et al. (2004) "Role of anti-CD20 monoclonal antibody in association with immunomodulatory agents," *Pathologie Biologie* 52:39-42 [English Abstract Only].
Cheng et al. (2008) "Antibody-fused interferons as an effective approach to enhance target specificity and antiviral efficacy of type I interferons," *Cell Research* 18:1230-1232.
Curtis et al. (1991) "Enhanced hematopoietic activity of a human granulocyte/macrophage colony-stimulating factor-interleukin 3 fusion protein," *Proc. Natl. Acad. Sci. USA*, 88:5809-5813.
Dela Cruz et al. (2004) "Antibody-cytokine fusion proteins: innovative weapons in the war against cancer," *Clin Exp Med*, 4:57-64.
Ebbinghaus et al. (2004) "An Antibody-Interferon Gamma Fusion Protein for Cancer Therapy," *A dissertation submitted to the Swiss Federal Institute of Technology Zurich for the degree of Doctor of Natural Sciences* pp. 1-137.
Ebbinghaus et al. (2005) "Engineered vascular-targeting antibody-interferon-γ fusion protein for cancer therapy," *Int. J. Cancer*, 116(2):304-313.
Field-Smith et al. (2006) "Bortezomib (Velcade™) in the treatment of multiple myeloma," *Therapeutics and Clinical Risk Management*, 2(3):271-279.
Flannery et al. (1984) "Immunomodulation: NK cells activated by interferon-conjugated monoclonal antibody against human osteosarcoma," *Eur J Cancer Clin Oncol.*, 20(6):791-798.
Frey et al. (2011) "Antibody-Based Targeting of Tumor Vasculature and Stroma," *The Tumor Microenvironment 4* Part VI Chapter 22:419-450.
Frey et al. (2011) "Antibody-based targeting of interferon-alpha to the tumor neovasculature: a critical evaluation," *Integr. Biol.*, 3:468-478.
Goldstein et al. (1988) "The role of interferon in cancer therapy: A current perspective," *CA Cancer J. Clin.*, 38(5):258-277.
Helguera et al. (2006) "Cytokines fused to antibodies and their combinations as therapeutic agents against different peritoneal HER2/neu expressing tumors," *Molecular Cancer Therapeutics, American Association of Cancer Research*, 5(4):1029-1040.
Heuser et al. (2003) "ANTI-CD30-IL-12 Antibody-Cytokine Fusion Protein That Induces IFN-Γ Secretion of T Cells and NK Cell-Mediated Lysis of Hodgkin's Lymphoma-Derived Tumor Cells," *Int. J. Cancer*, 106:545-552.
Huang et al. (2006) "Fusion of anti-HER2/ neu with inflammatory cytokines IFN-alpha and TNF-alpha results in molecules that elicit an anti-tumor response or potentiate wound healing," *Dissertation*, pp. 1-120 XP009158273.
Huang et al. (2007) "Targeting IFN-α to B cell lymphoma by a tumor-specific antibody elicits potent antitumor activities," *Journal of Immunology*, 179(10):6881-6888.
Huston et al. (1988) "Protein engineering of antibody binding sites: Recovery of specific activity in an anti-digoxin single-chain Fv analogue produced in *Escherichia coli*," *Proc. Natl. Acad. Sci.*, 85:5879-5883.
Jain et al. (2007) "Engineering antibodies for clinical applications," *Trends in Biotechnology*, 25(7):307-316.

(56) References Cited

OTHER PUBLICATIONS

Kaspar et al. (2007) "The Antibody-Mediated Targeted Delivery of Interleukin-15 and GM-CSF to the Tumor Neovasculature Inhibits Tumor Growth and Metastasis," *Cancer Res*, 67(10):4940-4948.
Klimka et al. (2003) "Construction of proteolysis resistant human interleukin-2 by fusion to its protective single chain antibody," *Cytokine*, 22:134-141.
McCarron et al. (2005) "Antibody Conjufates and Therapeutic Strategies," *Molecular Interventions*, 5(6):368-380.
Marshall et al. (2001) "Engineering and Characterization of a Novel Fusion Protein Incorporating B7.2 and an Anti-ErbB-2 Single-Chain Antibody Fragment for the Activation of Jurkat T Cells," *J. Immunotherapy*, 24(1):27-36.
Mickle, John E.; Ph.D. et al. (2000) "Genotype-Phenotype Relationships in Cystic Fibrosis," *Med. Clin. N. America*, 84(3):597-607.
Mizokami et al. (2003) "Chimeric TNT-3 Antibody/Murine Interferon-γ Fusion Protein for the Immunotherapy of Solid Malignancies," *Hybridoma and Hybridomics*, 22(4):197-207.
Ozzello et al.(1993) "The use of natural interferon alpha conjugated to a monoclonal antibody anti mammary epithelial mucin (Mc5) for the treatment of human breast cancer xenografts," *Breast Cancer Res Treat.*, 25(3):265-276.
Ozzello et al.(1998) "Conjugation of interferon alpha to a humanized monoclonal antibody (HuBrE-3vl) enhances the selective localization and antitumor effects of interferon in breast cancer xenografts," *Breast Cancer Res Treat.*, 48(2):135-47.
Pallela et al. (2000) "Interferon-α-2b immunoconjugate for improving immunoscintigraphy and immunotherapy," *The Journal of Nuclear Medicine*, 41(6):1108-1113.
Peng et al. (1999) "A Single-Chain IL-12 IgG3 Antibody Fusion Protein Retains Antibody Specificity and IL-12 Bioactivity and Demonstrates Antitumor Activity," *J. Immunol.*, 163:250-258.
Portlock et al. (2006) "Pegylated interferon plus rituximab in advanced stage, indolent lymphoma: is there CD20 antigen upregulation?" *Leukemia & Lymphoma*, 47(7):1260-1264.
Rossi et al. (2009) "CD20-targeted tetrameric interferon-, a novel and potent immunocytokine for the therapy of B-cell lymphomas," *Blood*, 114:3864-3871.
Rossi et al. (2010) "A Bispecific Antibody-IFNα2b Immunocytokine Targeting CD20 and HLA-DR Is Highly Toxic to Human Lymphoma and Multiple Myeloma Cells," *Cancer Res.*, 70:7600-7609.
Scharma et al. (2006) "Antibody targeted drugs as cancer therapeutics," *Nature Reviews Drug Discovery*, 5:147-159.
Seyfried et al. (2008) "Up-regulation of NG2 proteoglycan and interferon induced transmembrane proteins 1 and 3 in mouse astrocytoma: A membrane proteomics approach," *Cancer Letters*, 263(2):243-252.
Song et al. (2007) "Construction of Expression Vector of Anti-HBsAg dsFv and Alpha-IFN Fusion Gene," *Chinese Journal of Public Health*, 23(9):1096-1099 [English Abstract].
Takaoka et al. (Jul. 31, 2003) "Integration of interferon-α/β signalling to p53 responses in tumour suppression and antiviral defence," *Nature*, 424(6948):516-523.
Thakur et al. (1997) "Improved antibody targeting with interferon-α-2b conjugate," *Journal of Immunotherapy*, 20(3): 194-201.
Theofilopoulos et al. (2014) "Type I interferons (alpha/beta) in immunity and autoimmunity." *Annual Reviews of Immunology*, 23: 307-336.
Von Gabain, A., et al. (1990) "Three human interferon-α2 subvariants disclose structural and functional differences," *Eur. J. Biochem.*, 190:257-261.
Wei et al. (1998) "Clone and expression of a fusion protein consisting of anti-HBsAg Fab fragment and interferon-α in *E.coli,*" *Chinese Journal of Hepatology*, 6(4):229-231 [Abstract Only].
Wells, J.A., (Sep. 18, 1990) "Additivity of Mutational Effects in Proteins," *Biochemistry*, 29(37):8509-8517.
Xuan et al. (2010) "Targeted delivery of interferon-alpha via fusion to anti-CD20 results in potent antitumor activity against B-cell lymphoma," *Blood*, 115(14):2864-2871.
Yoo et al. (Dec. 11, 2012) Anti-CD138-IFNα Fusion Proteins are Effective in Treating Multiple Myeloma, In: *54th American Society of Hematology Annual Meeting and Exposition*, Atlanta, GA, Abstract No. 939, 1 page.
Zaidi et al. (2011) "The two faces of interferon-gamma in cancer," *Clin. Cancer Res.*, 17(19):1-7.
Zheng et al. (1998) "The Construction and Expression of a Fusion Protein Consisting of anti-HBsAg Antibody Fragment Fab and interferon—αA in *E.coli,*" *Chinese Journal of Hepatology*, 6(4):229-231 [English Abstract Only].
U.S. Notice of Allowance dated Aug. 8, 2018 issued in U.S. Appl. No. 15/359,456.
U.S. Notice of Allowance dated Jun. 1, 2018 issued in U.S. Appl. No. 14/893,912.
Japanese Decision of Rejection dated Jul. 2, 2018 issued in JP 2016-215048.
European Office Action dated Jan. 17, 2019 issued in EP 16195608.1.
Brazilian Office Action dated Oct. 15, 2019 issued in BR 0817108-4.
European Office Action dated Oct. 11, 2019 issued in EP 16195608.1.
Huang and Morrison (2005) "A Trimeric Anti-HER2/neu ScFv and Tumor Necrosis Factor-α Fusion Protein Induces HER2/neu Signaling and Facilitates Repair of Injured Epithelia," *Journal of Pharmacology and Experimental Therapeutics*, 316(3): 983-991.
U.S. Notice of Allowance dated May 19, 2020 issued in U.S. Appl. No. 16/150,171.
European Office Action dated May 29, 2020 issued in EP 16195608.1.

\* cited by examiner

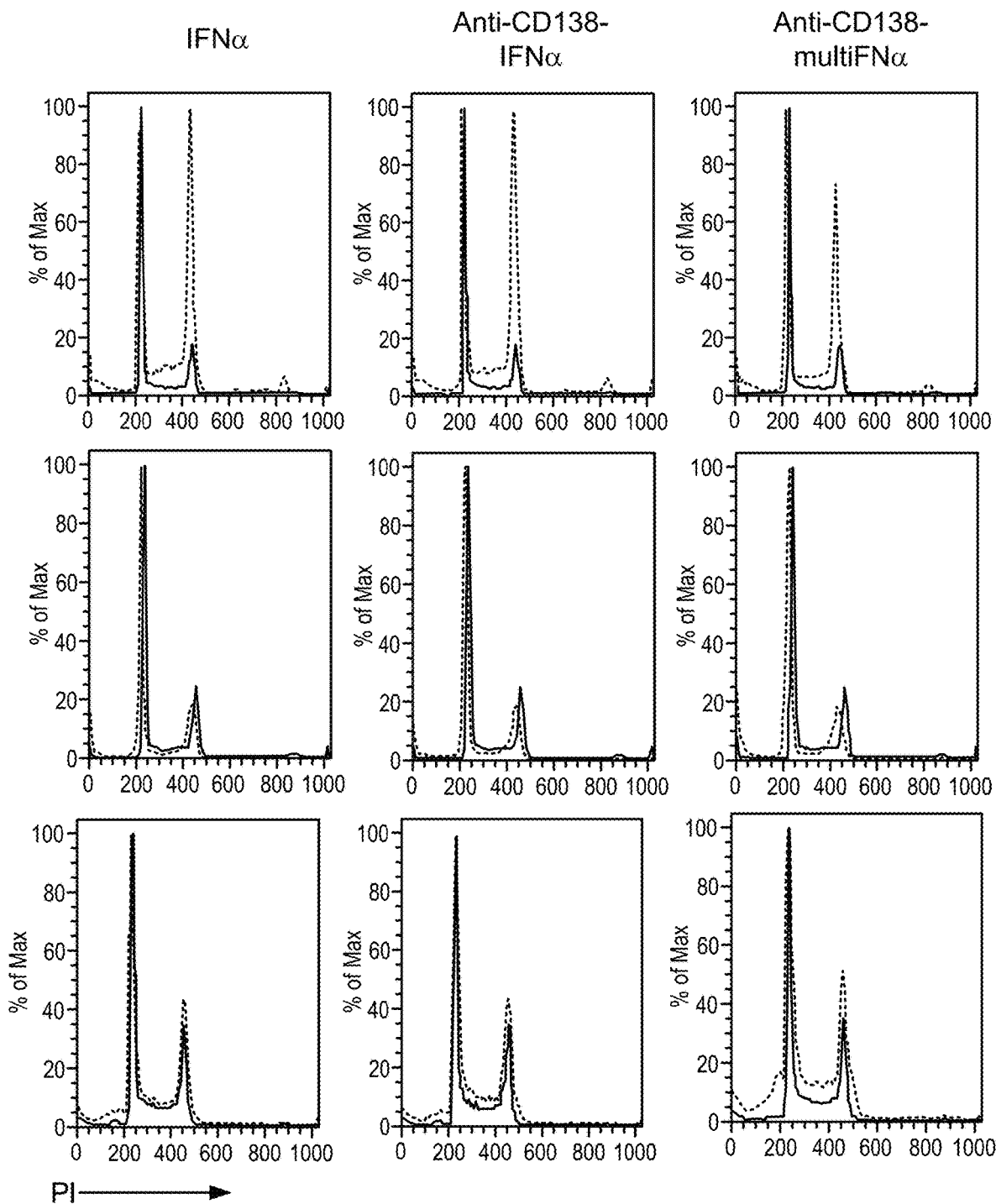
*Fig. 3B, cont'd.*

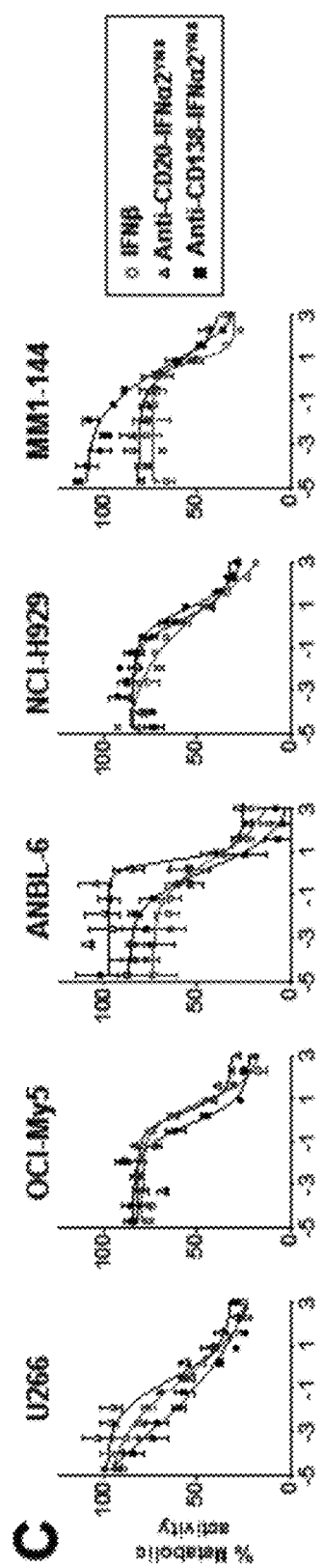
Fig. 14, cont'd.

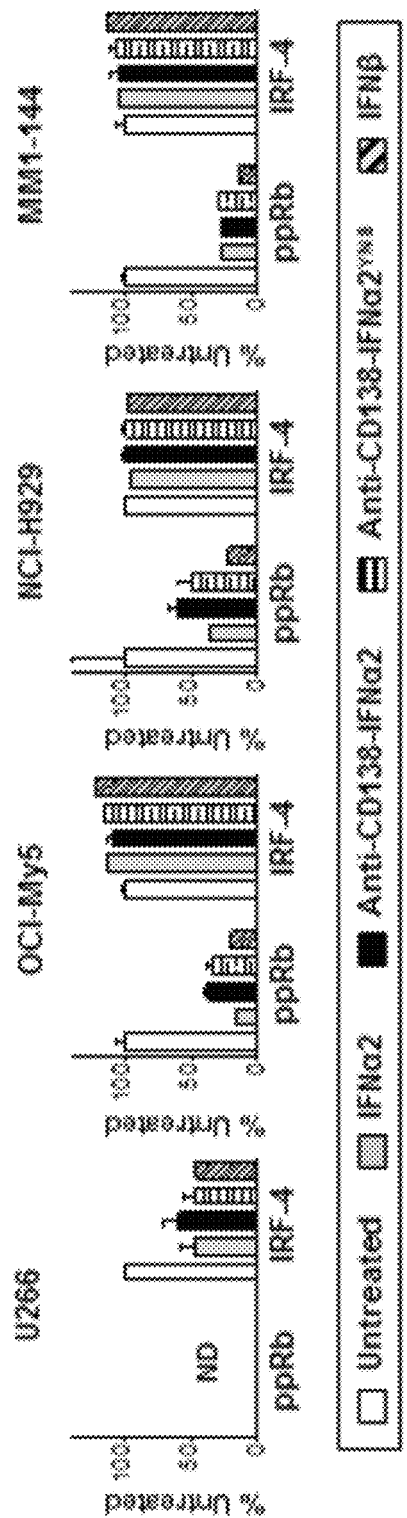
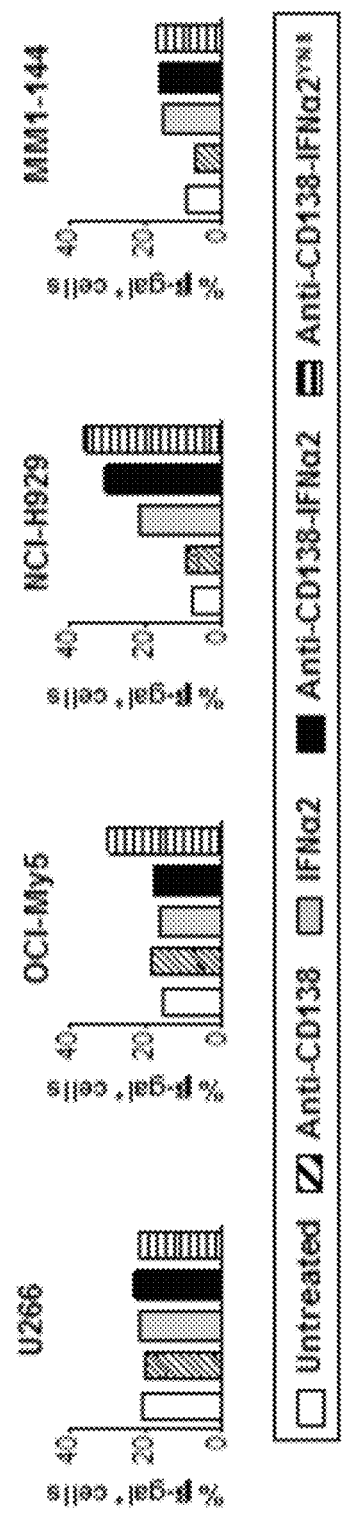
Fig. 16B
Fig. 16C

CD138-TARGETED INTERFERON DEMONSTRATES POTENT APOPTOTIC AND ANTI-TUMOR ACTIVITIES

CROSS-REFERENCE TO RELATED APPLICATIONS

This application is a Divisional of U.S. Ser. No. 14/649,888, filed Jun. 4, 2015, which is a U.S. 371 National Phase of PCT/US2013/073410, filed Dec. 5, 2013, which claims priority to and benefit of U.S. Ser. No. 61/734,851, filed Dec. 7, 2012, all of which are incorporated herein by reference in its entirety for all purposes.

STATEMENT OF GOVERNMENTAL SUPPORT

[ Not Applicable ]

INCORPORATION BY REFERENCE OF SEQUENCE LISTING PROVIDED AS A TEXT FILE

A Sequence Listing is provided herewith as a text file, "UCLA-P097D1US_ST25.txt" created on Feb. 27, 2018 and having a size of 25,659 bytes. The contents of the text file are incorporated by reference herein in their entirety.

BACKGROUND

Multiple myeloma (MM) is a disease characterized by an excess of malignant plasma cells in the bone marrow (BM). Most MM cells secrete IgG or IgA that contain somatic hypermutations, suggesting that the critical transformation processes occur in the germinal centers and may involve antigenic stimulation. Accumulation and proliferation of malignant myeloma cells result in disruption of normal hematopoiesis and changes to BM vascularization and bone physiology. MM is the second most prevalent hematologic malignancy in the US with a survival rate of 7-8 years when patients are treated with drugs such as proteasome inhibitor bortezomib, or thalidomide and lenalidomide, which target MM cells in the BM microenvironment (Kumar et al. (2008) Blood 111: 2516-2520).

MM is characterized by a wide variety of genetic mutations. Analyses of large numbers of patient MM cells and human myeloma cell lines (HMCLs; Carrasco et al. (2006) Cancer Cell 9: 313-325; Drexler et al. (2000) Leukemia, 14: 777-782; Lombardi et al. (2006) Genes Chromosomes Cancer, 46: 226-238; Moreaux et al. (2011) Haematologica, 96: 574-582) attest to the molecular heterogeneity of this disease. There are two oncogenic pathways that are responsible for the initial onset of MM or the premalignant disease called monoclonal gammopathy of undetermined significance (MGUS)—hyperdiploidy sometimes containing multiple trisomies of chromosomes 3, 5, 7, 9, 11, 15, 19, and 21 and primary immunoglobulin translocations involving 11q13 (CCND1), 4p16 (FGFR3/WHSC1), 6p21 (CCND3), 16q23 (MAF), and 20q11 (MAFB), which result in dysregulated expression of the target genes. Disease progression is marked by activating mutations to K- or N-Ras and inactivation of CDKN2A, CDKN2C, CDKN1B, and/or PTEN tumor suppressor genes. As tumors become more aggressive in later stages of the disease, secondary Ig translocations involving MYC have been found in MM. This is in contrast to human Burkitt's lymphoma and murine plasmacytoma in which c-myc translocation is an early oncogenic event. In addition, mutations and/or deletions of p18 and p53 have been observed as late events in MM pathogenesis.

Interferons have been contemplated for use in the treatment of cancer (Borden et al. (2000) Semin. Cancer Biol., 10: 125-144; Borden et al. (2007) Nat. Rev. Drug Discov., 6: 975-990). There are seven classes of type I IFNs with IFNα and IFNβ being the most abundant. Both IFNα and IFNβ bind to the same receptor composed of two transmembrane proteins, IFNAR 1 and 2, but IFNβ binds with much higher affinity than IFNα (Lamken et al. (2004) J Mol Biol 341: 303-318). IFNs have been shown to have anti-proliferative activity as well as the ability to induce apoptosis in hematological malignancies and solid tumors in addition to their anti-viral activity (as reviewed in Borden et al. (2007) Nat. Rev. Drug Discov., 6: 975-990). However, the effectiveness of IFNα for cancer therapy is overshadowed by side effects when used at high doses (Weiss (1998) Semin. Oncol., 25: 9-13) and by a short half-life of only 1 hour (Peleg-Shulman et al. (2004) J. Med. Chem., 47: 4897-904). Strategies to increase the half-life have included the covalent linkage of polyethylene glycols (PEG) to IFNα (Talpaz et al. (2001) Blood, 98: 1708-1713), but such modifications have resulted in lower activity (Rosendahl et al. (2005) Bioconjug. Chem., 16: 200-207).

SUMMARY

In various embodiments this invention pertains to the discovery that attaching an interferon to a targeting moiety (e.g., a molecule that specifically and/or preferentially binds a marker on or associated with a cell) substantially improves the therapeutic efficacy of the interferon and appears to reduce systemic toxicity. Accordingly, in various embodiments, this invention provides constructs comprising an interferon attached to a targeting moiety and uses of such constructs to specifically and/or preferentially inhibit the growth or proliferation or even to kill certain target cells (e.g., cancer cells). In certain embodiments the constructs comprise a mutant interferon, e.g., a mutant IFNα with higher affinity for the IFNAR to enhance the potency of the construct.

Accordingly, in certain embodiments, a chimeric construct is provided where the construct comprises an interferon (e.g., interferon-alpha, interferon-beta, interferon-gamma, mutant interferon-α, mutant interferon-β, and the like) attached to a targeting moiety that binds to a tumor associated antigen, in particular CD138. The construct when contacted to a tumor cell results in the killing or inhibition of growth or proliferation of the tumor cell.

In various aspects, the invention(s) contemplated herein may include, but need not be limited to, any one or more of the following embodiments:

Embodiment 1: A construct including an interferon attached to an antibody that binds CD138.

Embodiment 2: The construct of embodiment 1, wherein said construct when contacted to a cell that expresses or overexpresses CD138 cell results in the killing or inhibition of growth or proliferation of said cell.

Embodiment 3: The construct of embodiment 2, wherein said cell that expresses or overexpresses CD138 is a cancer cell.

Embodiment 4: The construct of embodiment 2, wherein said cell that expresses or overexpresses CD138 is a cancer from a cancer selected from the group consisting of multiple myeloma, ovarian carcinoma, cervical cancer, endometrial cancer, kidney carcinoma, gall bladder carcinoma, transitional cell bladder carcinoma, gastric cancer, prostate adenocarcinoma, breast cancer, prostate cancer, lung cancer, colon carcinoma, Hodgkin's and non-Hodgkin's lymphoma, chronic lymphocytic leukemia (CLL), acute lymphoblastic leukemia (ALL), acute myeloblastic leukemia (AML), a solid tissue sarcoma, colon carcinoma, non-small cell lung carcinoma, squamous cell lung carcinoma, colorectal carcinoma, hepato-carcinoma, pancreatic cancer, and head and neck carcinoma.

Embodiment 5: The construct according to any one of embodiments 1-4, wherein said interferon is a type I interferon.

Embodiment 6: The construct according to any one of embodiments 1-4, wherein said interferon is a type II interferon (IFNγ).

Embodiment 7: The construct of embodiment 5, wherein said interferon is an interferon-alpha (e.g., IFNα2).

Embodiment 8: The construct of embodiment 7, wherein said interferon is an interferon alpha 2 (IFNα2).

Embodiment 9: The construct of embodiment 7, wherein said interferon is an interferon alpha 14 (IFNα14).

Embodiment 10: The construct of embodiment 5, wherein said interferon is an interferon-beta (IFNβ).

Embodiment 11: The construct according to any one of embodiments 7-10, wherein said interferon is a human interferon.

Embodiment 12: The construct according to any one of embodiments 7-10, wherein said interferon is a non-human interferon.

Embodiment 13: The construct of embodiment 12, wherein said interferon is a murine interferon.

Embodiment 14: The construct according to any one of embodiments 1-4, wherein said interferon is a mutant type I interferon.

Embodiment 15: The construct of embodiment 14, wherein said interferon is a mutant interferon-alpha.

Embodiment 16: The construct of embodiment 14, wherein said interferon is a mutant human interferonα-2 having mutations at one or more sites selected from the group consisting of His57, Glu58, and Gln61.

Embodiment 17: The construct of embodiment 16, wherein said interferon is an interferonα-2 having a mutation at His57.

Embodiment 18: The construct of embodiment 17, wherein said mutation at His57 is a mutation to an amino acid selected from the group consisting of A, Y, and M.

Embodiment 19: The construct according to any one of embodiments 16-19, wherein said interferon is an interferonα-2 having a mutation at Glu58.

Embodiment 20: The construct of embodiment 19, wherein said mutation at Glu58 is a mutation to an amino acid selected from the group consisting of A, N, D, and L.

Embodiment 21: The construct according to any one of embodiments 16-20, wherein said interferon is an interferonα-2 having a mutation at Gln61.

Embodiment 22: The construct of embodiment 19, wherein said mutation at Gln61 is a mutation to an amino acid selected from the group consisting of A, S, and D.

Embodiment 23: The construct of embodiment 16, wherein said interferon includes the mutations H57Y, E58N, and Q61S.

Embodiment 24: The construct of embodiment 16, wherein said interferon includes the mutations H57M, E58L, and Q61D.

Embodiment 25: The construct of embodiment 16, wherein said interferon includes the mutations H57Y, E58L, and Q61D.

Embodiment 26: The construct of embodiment 16, wherein said interferon includes the mutations H57Y, E58A, and Q61S.

Embodiment 27: The construct of embodiment 16, wherein said interferon includes the mutations H57A, E58A, and Q61A.

Embodiment 28: The construct according to any one of embodiments 1-27, wherein said antibody includes the complementarity determining regions of the B-B4 monoclonal antibody.

Embodiment 29: The construct of embodiment 28, wherein said antibody includes the VH and/or VL domain of the B-B4 monoclonal antibody.

Embodiment 30: The construct according to any one of embodiments 1-29, wherein said antibody is an antibody selected from the group consisting of is a single chain Fv (scFv), a FAB , a (Fab')2, an (ScFv)$_2$, and a full IgG.

Embodiment 31: The construct according to any one of embodiments 1-29, wherein said antibody is an scFv.

Embodiment 32: The construct according to any one of embodiments 1-29, wherein said antibody is a full IgG.

Embodiment 33: The construct of embodiment 29, wherein said antibody is the B-B4 monoclonal antibody.

Embodiment 34: The construct according to any of embodiments 1-33, wherein said antibody is chemically coupled to said interferon.

Embodiment 35: The construct according to any of embodiments 1-33, wherein said antibody is directly joined to said interferon (e.g., at the C terminus of the heavy chain, at the C terminus of the light chain, at the N terminus of the heavy chain, or at the N-terminus of the light chain of the antibody).

Embodiment 36: The construct according to any of embodiments 1-33, wherein said antibody is directly joined to said interferon with a peptide linker (e.g., at the C terminus of the heavy chain, at the C terminus of the light chain, at the N terminus of the heavy chain, or at the N-terminus of the light chain of the antibody).

Embodiment 37: The construct of embodiment 36, wherein said peptide linker is proteolysis resistant.

Embodiment 38: The construct of according to any one of embodiments 36-37, wherein said peptide linker is fewer than 15 amino acids in length.

Embodiment 39: The construct of according to any one of embodiments 36-38, wherein said peptide linker is not (Gly$_4$Ser)$_3$.

Embodiment 40: The construct of embodiment 35, wherein the amino acid sequence of said peptide linker is selected from the group consisting of GGG, GGS, GGGGS (SEQ ID NO:7), SGGGGS (SEQ ID NO:8), GGGGSGGGGS (SEQ ID NO:9), A EAAAK A (SEQ ID NO:10), A EAAAK EAAAK A (SEQ ID NO:11), A EAAAK EAAAK EAAAK A (SEQ ID NO:12), A EAAAK EAAAK EAAAK EAAAK A (SEQ ID NO:13), A EAAAK EAAAK EAAAK EAAAK EAAAK A (SEQ ID NO:14), AEAAAKEAAAKAG (SEQ ID NO:15), AEAAAKEAAAKAGS (SEQ ID NO:16), GGGGG (SEQ ID NO:17), GGAGG (SEQ ID NO:18), GGGGGGGG (SEQ ID NO:19), GAGAGAGAGA (SEQ ID NO:20), RPLSYRPPFPFGFPSVRP (SEQ ID NO:21), YPRSIYIRRRHPSPSLTT (SEQ ID NO:22), TPSHLSHILPSFGLPTFN (SEQ ID NO:23), RPVSPFTFPRLSNSWLPA (SEQ ID NO:24), SPAAHFPRSIPRPGPIRT (SEQ ID NO:25), APGPSAPSHRSLPSRAFG (SEQ ID NO:26), PRNSIHFLHPLLVAPLGA (SEQ ID NO:27), MPSLSGVLQVRYLSPPDL (SEQ ID NO:28), SPQYPSPLTLTLPPHPSL (SEQ ID NO:29), NPSLNPP- SYLHRAPSRIS (SEQ ID NO:30), LPWRTSLLPSLPLRRRP (SEQ ID NO:31), PPLFAKGPVGLLSRSFPP (SEQ ID NO:32), VPPAPVVSLRSAHARPPY (SEQ ID NO:33), LRPTPPRVRSYTCCPTP (SEQ ID NO:34), PNVAHVLPLLTVPWDNLR (SEQ ID NO:35), CNPLLPLCARSPAVRTFP (SEQ ID NO:36), LGTPTPTPTPTGEF (SEQ ID NO:37), EDFTRGKL (SEQ ID NO:38), L EAAAR EAAAR EAAAR EAAAR (SEQ ID NO:39), L EAAAR EAAAR EAAAR (SEQ ID NO:40), L EAAAR EAAAR (SEQ ID NO:41), L EAAAR (SEQ ID NO:42), EAAAR EAAAR EAAAR EAAAR (SEQ ID NO:43), EAAAR EAAAR EAAAR (SEQ ID NO:44), EAAAR EAAAR (SEQ ID NO:45), and EAAAR (SEQ ID NO:46).

Embodiment 41: The construct of embodiment 35, wherein the amino acid sequence of said peptide linker is selected from the group consisting of GGGGS (SEQ ID NO:7), SGGGGS (SEQ ID NO:8), AEAAAKEAAAKAG (SEQ ID NO:15), and AEAAAKEAAAKAGS (SEQ ID NO:16).

Embodiment 42: The construct of embodiment 35, wherein the amino acid sequence of said peptide linker is SGGGGS (SEQ ID NO:8).

Embodiment 43: The construct of embodiment 1, wherein said construct includes the YNS mutant interferon attached to the B-B4 monoclonal antibody by a linker including or consisting of the amino acid sequence SGGGGS (SEQ ID NO:8).

Embodiment 44: The construct of embodiment 43, wherein said interferon is attached to the end of CH3 by said linker.

Embodiment 45: The according to any one of embodiments 1-44, wherein said construct or a component thereof is a recombinantly expressed fusion protein.

Embodiment 46: A pharmaceutical formulation including a construct according to any of embodiments 1-45 in a pharmaceutically acceptable excipient.

Embodiment 47: The pharmaceutical formulation according to embodiment 46, wherein said formulation is a unit dosage formulation.

Embodiment 48: The pharmaceutical formulation according to embodiment 46, wherein said formulation is a formulated for parenteral administration.

Embodiment 49: The pharmaceutical formulation according to embodiment 46, wherein said formulation is a formulated for administration via a route selected from the group consisting of oral administration, intravenous administration, intramuscular administration, direct tumor administration, inhalation, rectal administration, vaginal administration, transdermal administration, and subcutaneous depot administration.

Embodiment 50: A method of inhibiting growth and/or proliferation of a cell that expresses or overexpresses CD138, said method including contacting said cell with a construct according to any of embodiments 1-45, or a formulation according to any one of embodiments 46-49 in an amount sufficient to inhibit growth or proliferation of said cell.

Embodiment 51: The method of embodiment 50, wherein said cell is a cancer cell.

Embodiment 52: The method of embodiment 51, wherein said cancer cell is a metastatic cell.

Embodiment 53: The method of embodiment 51, wherein said cancer cell is in a solid tumor.

Embodiment 54: The method of embodiment 51, wherein said cancer cell is cell produced by a cancer selected from the group consisting of multiple myeloma, ovarian carcinoma, cervical cancer, endometrial cancer, kidney carcinoma, gall bladder carcinoma, transitional cell bladder carcinoma, gastric cancer, prostate adenocarcinoma, breast cancer, prostate cancer, lung cancer, colon carcinoma, Hodgkin's and non-Hodgkin's lymphoma, chronic lymphocytic leukemia (CLL), acute lymphoblastic leukemia (ALL), acute myeloblastic leukemia (AML), a solid tissue sarcoma, colon carcinoma, non-small cell lung carcinoma, squamous cell lung carcinoma, colorectal carcinoma, hepato-carcinoma, pancreatic cancer, and head and neck carcinoma.

Embodiment 55: The method of embodiment 51, wherein said cancer cell is a cell of a multiple myeloma.

Embodiment 56: The method according to any one of embodiments 50-55, wherein said method includes inhibiting, delaying and/or preventing the growth of a tumor and/or spread of malignant tumor cells.

Embodiment 57: The method according to any one of embodiments 50-56, wherein said contacting includes systemically administering said construct or formulation to a mammal.

Embodiment 58: The method according to any one of embodiments 50-56, wherein said contacting includes administering said construct or formulation directly into a tumor site.

Embodiment 59: The method according to any one of embodiments 50-56, wherein said contacting includes administering said construct or formulation via a route selected from the group consisting of oral administration, intravenous administration, intramuscular administration, direct tumor administration, inhalation, rectal administration, vaginal administration, transdermal administration, and subcutaneous depot administration.

Embodiment 60: The method according to any one of embodiments 50-56, wherein said contacting includes administering said construct or formulation intravenously.

Embodiment 61: The method according to any one of embodiments 50-60, wherein said cell is a cell in a human.

Embodiment 62: The method according to any one of embodiments 50-60, wherein said cell is a cell in a non-human mammal.

Embodiment 63: The method of embodiment 50, wherein said cancer cell is a cell produced by a multiple myeloma.

Embodiment 64: The method of embodiment 50, wherein said contacting includes systemically administering said construct to a mammal.

Embodiment 65: The method of embodiment 50, wherein said contacting includes administering said construct directly into a tumor site.

Embodiment 66: The method of embodiment 50, wherein said contacting includes intravenous administration of said construct.

Embodiment 67: The method of embodiment 50, wherein said cancer cell is a cancer cell in a human.

Embodiment 68: The method of embodiment 50, wherein said cancer cell is a cancer cell in a non-human mammal.

Embodiment 69: The method according to any one of embodiments 51-68, wherein said method further includes administering to said subject one or more cytotoxic agents and/or radiation in an amount effective to reduce tumor load, and/or to inhibit, delay, or prevent, the growth and/or spread of tumor cells including CD138 expressing cells.

Embodiment 70: The method of embodiment 69, wherein said method includes administering to said subject bortezomib (VELCADE®).

Embodiment 71: The method of embodiment 69, wherein said method includes administering to said subject lenalidomide.

Embodiment 72: A method for inhibiting, delaying and/or preventing the growth of a tumor and/or spread of malignant tumor cells in a subject in need thereof, said method including: administering to said subject a construct according to any of embodiments 1-45, or a formulation according to any one of embodiments 46-49; and administering to said subject one or more cytotoxic agents and/or radiation in an amount effective to reduce tumor load, and/or to inhibit, delay, or prevent the growth and/or spread of tumor cells including CD138 expressing cells.

Embodiment 73: The method of embodiment 72, wherein said method includes administering to said subject bortezomib (VELCADE®).

Embodiment 74: The method of embodiment 72, wherein said method includes administering to said subject lenalidomide.

Embodiment 75: A formulation including a construct according to any of embodiments 1-45, and bortezomib and/or lenalidomide.

Embodiment 76: A kit including: a formulation including a construct according to any of embodiments 1-45; and bortezomib and/or lenalidomide.

Embodiment 77: A synergistic combination of a construct according to any of embodiments 1-45, and bortezomib and/or lenalidomide.

Embodiment 78: A nucleic acid that encodes a fusion protein, said fusion protein including an interferon attached to an anti-CD138 single-chain antibody or to a polypeptide including an anti-CD138 chain antibody.

Embodiment 79: The nucleic acid of embodiment 78, wherein said interferon is an interferon as found in a construct according to any of embodiments 1-45.

Embodiment 80: The nucleic acid according to any one of embodiments 78-79, wherein said antibody is an anti-CD138 antibody as found in a construct according to any of embodiments 1-45.

Embodiment 81: The nucleic acid according to any one of embodiments 78-80, wherein said nucleic acid encodes a construct or a component of a construct according to any of embodiments 1-45.

Embodiment 82: A cell including a nucleic acid that expresses a fusion protein, said cell including a nucleic acid according to any of embodiments 78-81.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

An "antibody", as used herein, refers to a protein consisting of one or more polypeptides substantially encoded by immunoglobulin genes or fragments of immunoglobulin genes. In certain embodiments, the immunoglobulin genes are human immunoglobulin genes. Recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively.

A typical (native) immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively.

Antibodies exist as intact immunoglobulins or as a number of well characterized fragments produced by digestion with various peptidases or expressed de novo. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, IgE, scFv, dAb, nanobodies, unibodies, and diabodies. In various embodiments preferred antibodies include, but are not limited to Fab'$_2$, IgG, IgM, IgA, IgE, and single chain antibodies, more preferably single chain Fv (scFv) antibodies in which a variable heavy and a variable light chain are joined together (directly or through a peptide linker) to form a continuous polypeptide.

In certain embodiments antibodies and fragments used in the constructs described herein can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al. (1981) *Proc. Natl. Acad. Sci., USA*, 78: 5807), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest,* 4th ed. U.S. Dept. Health and Human Services, Public Health Services, Bethesda, Md. (1987).

The term "interferon" refers to a full-length interferon or to an interferon fragment (truncated interferon) or interferon mutant, that substantially retains the biological activity of the full length wild-type interferon (e.g., retains at least 50%, or preferably at least 60%, or preferably at least 70%, or preferably at least 80%, preferably at least 90%, more preferably at least 95%, 98%, or 99% of the full-length interferon in its free form (e.g., when not a component of a chimeric construct). Interferons include type I interferons (e.g., interferon-alpha and interferon-beta) as well as type II inteferons (e.g., interferon-gamma). The interferon (e.g., IFN-α) can be from essentially any mammalian species. In certain preferred embodiments, the interferon is from a species selected from the group consisting of human, equine, bovine, rodent, porcine, lagomorph, feline, canine, murine, caprine, ovine, a non-human primate, and the like. In various embodiments the mutated interferon comprises one or more amino acid substitutions, insertions, and/or deletions.

A single chain Fv ("sFv" or "scFv") polypeptide is a covalently linked $V_H$:$V_L$ heterodimer which, in certain embodiments, may be expressed from a nucleic acid including $V_H$- and $V_L$-encoding sequences either joined directly or joined by a peptide-encoding linker. Huston et al. (1998) *Proc. Nat. Acad. Sci. USA,* 85: 5879-5883. A number of approaches for converting the naturally aggregated, but chemically separated light and heavy polypeptide chains from an antibody V region into an sFv molecule that will fold into a three dimensional structure substantially similar to the structure of an antigen-binding site are known (see, e.g., U.S. Pat. Nos. 5,091,513 and 5,132,405, and 4,956,778).

"CD138" also known as syndecan-1 is a protein that in humans is encoded by the SDC1 gene. The protein encoded by this gene is a transmembrane (type I) heparan sulfate proteoglycan and is a member of the syndecan proteoglycan family. The syndecans mediate cell binding, cell signaling, and cytoskeletal organization and syndecan receptors are required for internalization of the HIV-1 tat protein. The syndecan-1 protein functions as an integral membrane protein and participates in cell proliferation, cell migration and cell-matrix interactions via its receptor for extracellular matrix proteins. Altered syndecan-1 expression has been detected in several different tumor types. While several transcript variants may exist for this gene, the full-length natures of only two have been described to date. These two represent the major variants of this gene and encode the same protein. Syndecan-1 (CD138) is a surface proteoglycan consisting of long unbranched glycosaminoglycan (GAG) chains covalently attached to a protein backbone.

The phrase "inhibition of growth and/or proliferation" of a cancer cell refers to decrease in the growth rate and/or proliferation rate of a cancer cell. In certain embodiments this includes death of a cancer cell (e.g. via apoptosis). In certain embodiments this term also refers to inhibiting the growth and/or proliferation of a solid tumor and/or inducing tumor size reduction or elimination of the tumor.

The term "cancer marker" refers to biomolecules such as proteins, carbohydrates, glycoproteins, and the like that are exclusively or preferentially or differentially expressed on a cancer cell and/or are found in association with a cancer cell and thereby provide targets preferential or specific to the cancer. In various embodiments the preferential expression can be preferential expression as compared to any other cell in the organism, or preferential expression within a particular area of the organism (e.g. within a particular organ or tissue).

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like. Where administration is described herein, "causing to be administered" is also contemplated.

BRIEF DESCRIPTION OF THE DRAWINGS

FIG. 1A: Schematic diagram of anti-CD138-IFNα fusion protein. The fusion protein contains murine variable region of antibody B-B4, which is specific for CD138, and human IgG1κ constant regions. Human IFNα2 is fused to the C-terminus of the antibody via a flexible SGGGGS (SEQ ID NO:8) linker. FIG. 1B: The effect of IFNα and anti-CD138-IFNα on Daudi cells. Cells were treated for 72 h with 0.0032-50 pM IFNα or 0.032-500 pM anti-CD138-IFNα, and cell viability was measured using the MTS assay. The experiment was performed once with data averaged from triplicates.

FIG. 3A: The effect of treatments on cell viability. HMCLs were treated with 0.00002 pM-1 nM of IFNα, anti-CD138-IFNα and anti-CD138-mutIFNα for 3 days (OCI-My 5, U266, H929 and MM144), 4 days (8226/S) or 7 days (ANBL-6) and analyzed for cell viability by MTS assay. The experiment was performed in triplicate for each concentration. FIG. 3B: Cell cycle analysis following treatment. HMCLs were treated with 500 pM of the indicated proteins for 4 days. Following permeabilization and staining with PI, DNA content was analyzed by flow cytometry. FIG. 3C: Determination of induction of apoptosis following treatment. HMCLs were treated with 500 pM of the indicated proteins for 3 days and then stained with Alexa Fluor 488 labeled Annexin V and PI and then analyzed by flow cytometry. The numbers in the upper right quadrant indicate the percentage of Annexin V$^+$PI$^+$ apoptotic cells.

FIG. 4A: Cells were treated for 3 days with 0.3 pM-25 nM of the indicated proteins. The proliferative status of the cells was determined by measuring $^3$[H]-thymidine incorporation. FIG. 4B: Cells were treated with 1 nM of the indicated proteins for 3 days. Cleavage of the substrate $C_{12}$FDG was detected by flow cytometry as an indication of β-gal activity at pH 6. The percentage of cells with β-gal activity is shown. The experiment was also performed at 4, 6 and 7 days after treatment with similar results.

FIG. 6A: SCID mice were injected subcutaneously with 1×10$^7$ OCI-My 5 cells and treated on days 14, 16 and 18 as indicated by the black arrows with 100 μg of the indicated proteins. Survival and tumor growth were monitored. n=8. FIG. 6B: NSG mice were injected subcutaneously with 1×10$^7$ U226 cells and treated on days 14, 16 and 18 as indicated by the black arrows with 100 μg of the indicated proteins. One group was treated three additional times with anti-CD138-mutIFNα on days 25, 32 and 63 as indicated by the grey arrows. Survival and tumor growth were monitored. n=8.

FIG. 13A shows a schematic diagram of anti-CD138 fusion proteins containing IFNα2 or IFNα2$^{YNS}$. The fusion proteins contain V regions of murine antibody B-B4, which is specific for CD138, and human IgG1κ constant regions. Human IFNα2 or IFNα2$^{YNS}$ is fused to the C-terminus of the antibody via a SerGly$_4$Ser peptide linker. FIG. 13B shows SDS PAGE analysis of reduced and unreduced purified fusion proteins and control IgG.

FIG. 15A) HMCLs were treated with 500 pM of the indicated proteins for 3 days and then stained with Alexa Fluor 488 labeled Annexin V and PI and analyzed by flow cytometry to assess induction of apoptosis at high dose. The number in the upper right quadrants indicates the percentage of Annexin V$^+$/PI$^+$ cells. The number in the lower right quadrants for OCI-My 5 cells indicates the percentage of Annexin V$^+$/PI$^-$ cells. FIG. 15B) HMCLs (except OCI-My5, which was treated with 5 pM) were treated with 1 pM of the indicated proteins to assess apoptosis at low dose. Cells were treated for 3 days and then stained with Alexa Fluor 488 labeled Annexin V and PI and analyzed by flow cytometry as described above. Some of the data are shown above in FIG. 3C.

FIGS. 16A-16D show that IFNα2 and fusion proteins can induce alterations in cell cycle progression and senescence in some HMCLs. FIG. 16A) HMCLs were treated with 500 pM of the indicated proteins for 4 days. Following permeabilization and staining with PI, DNA content was analyzed by flow cytometry. Shaded histograms are untreated cells, and solid lines are treated cells. The percentages of cells in different phases of the cell cycle are shown in Table 5. Some of the data are shown in FIG. 3B. FIG. 16B) Cells were treated with for 48 hours with 1 nM anti-CD138, IFNα2, anti-CD138-IFNα2, or anti-CD138-IFNα2$^{YNS}$. Cell lysates were used to determine the levels of ppRb and IRF-4 by Western blotting. Protein loading was monitored by probing the same membranes with anti-GAPDH. The bands from the blots were quantified using NIH Image J software, and the ratio of GAPDH to either protein is shown. ND=not detected. U266 data of 16B shown in FIG. 9. FIG. 16C) Cells were treated with 1 nM of the indicated proteins for 3 days. β-gal activity at pH 6, an indicator of senescence, was determined by following cleavage of the substrate $C_{12}$FDG. OCI-My5 data shown in FIG. 4B and again FIG. 11. H929 shown in FIG. 11. FIG. 16D) Cells were treated with 500 pM of the indicated proteins for 3 days. Expression of Ki-67 was determined by using rabbit anti-Ki-67 followed by anti-rabbit IgG-FITC and analyzed by flow cytometry. Dashed lines are unstained cells. Shaded histograms are untreated, stained cells and bold lines are treated, stained cells. The percentage of Ki-67 cells is shown.

FIG. 17A) Scid mice were injected subcutaneously with 1×10$^7$ OCI-My5 cells and treated on days 14, 16 and 18 as shown by the black arrows with 100 μg of the indicated proteins. Survival and tumor growth were monitored. Eight mice were treated for each group. One mouse survived to day 120. Similar data to FIG. 6A, but has p values. FIG. 17B) NSG mice were injected subcutaneously with 1×10$^7$ U226 cells and treated on days 14, 16 and 18 as indicated by the black arrows with 100 μg of the indicated proteins. Survival and tumor growth were monitored. Eight mice were treated for each group. P values were calculated between groups. ⁻p≥0.05, *p<0.02, p<0.008, *p≤0.0007. Similar data in FIG. 6B but has p values and does not show all of the groups.

DETAILED DESCRIPTION

Interferon alpha (IFNα) is an important cytokine in initiating the innate immune response and also demonstrates a wide spectrum of anti-tumor activities. The clinical use of interferon (e.g., IFNα) as an anticancer drug, however, is hampered by its short half-life, which significantly compromises its therapeutic effect. In certain embodiments this invention pertains to the discovery that the therapeutic index of interferon can be improved by attaching the interferon to a targeting moiety that specifically/preferentially binds a marker on or associated with the target cell (e.g., a tumor cell). This permits the delivery of higher doses of interferon to the target site with fewer systemic complications. In certain embodiments the construct shows lower side effects/toxicity than an untargeted interferon.

In particular, anti-CD138-IFNα2 antibody fusion proteins were constructed. CD138, also known as syndecan-1, is a heparan sulfate proteoglycan expressed by multiple myeloma (MM) cell lines, and in patients, it is expressed on malignant plasma cells in peripheral blood and in the bone marrow (Wijdenes 1996, Ridley 1993, Chilosi 1999). The ectodomain of CD138 is secreted into the serum in vivo (Dhodapkar 1997), and is shed by cultured cells (Subramanian 1997). CD138 mediates adhesion to growth factors (Kiefer 1990) and extracellular matrix components (Bernfield 1992) such as type I collagen (Ridley 1993).

As explained below and in the Example, targeting of human IFN (e.g., IFNα) via the anti-CD138 antibody moiety improves the cytoreductive effects of the cytokine. Multiple mechanisms of action such as induction of apoptosis, blockage in cell cycle progression and induction of senescence appear to be involved as HMCLs have different responses to treatment with fusion protein as explained below. It is also demonstrated that the fusion protein is effective against primary human myeloma patient cells and against MM tumors in a mouse xenograft model. In addition, mutations that increase the affinity of IFNα for IFNAR resulted in a more effective molecule in vitro and in vivo.

Figure 1A:
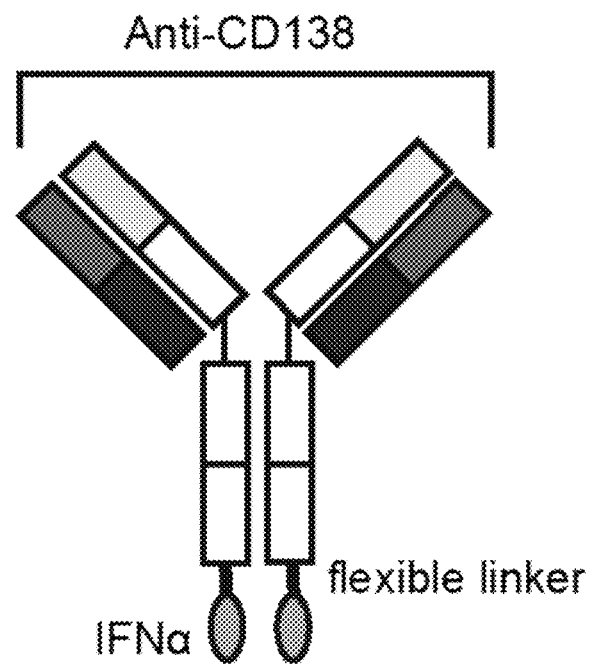
FIGS. 1A and 1B illustrate the production and activity of anti-CD138-IFNα.

Antibody fusions were produced by genetically fusing IFN to the end of CH3 of an IgG1κ antibody molecule. A schematic of this fusion protein specific for CD138 is illustrated in FIG. 1A.

As illustrated in the Examples, the proteins were expressed following gene transfection into Chinese hamster ovary (CHO) cells and were purified using protein A sepharose or agarose. The proteins expressed from the transfected genes were of the appropriate size and are assembled into H2L2 molecules.

A mutant IFNα (mutated IFNα2 or IFNα2$^{YNS}$ having the mutations H57Y, E58N, and Q61S (YNS) (see, e.g., Kalie et al. (2007) *J. Biol. Chem.*, 282: 11602-11611)) was fused to the terminus of CH3 in an identical fashion used to fuse wild-type IFNα. The mutant IFNα has higher affinity for IFNAR.

Figure 7:
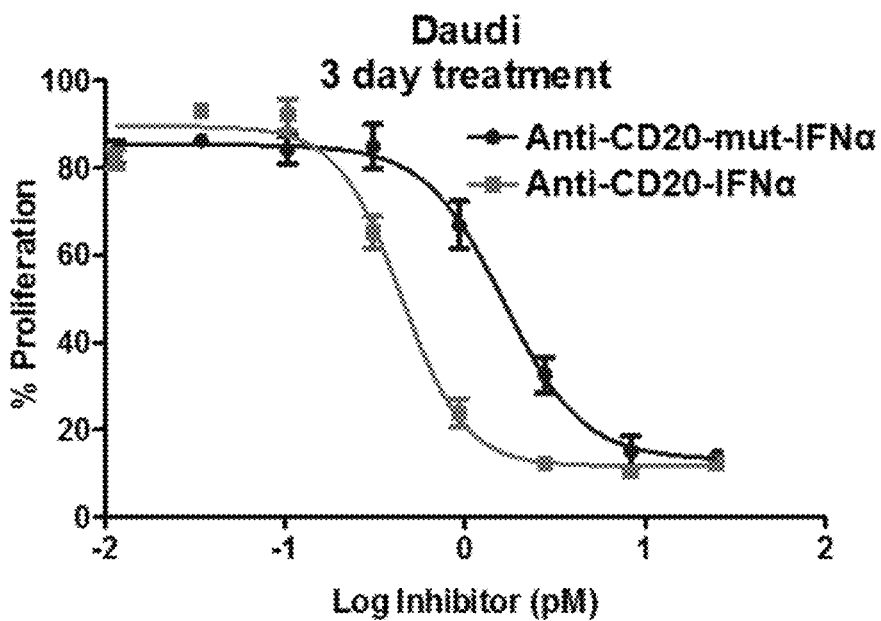
FIG. 7 comparison of anti-proliferative activity of anti-CD20-IFNα with anti-CD20-mut-IFNα.

A first construct was made comprising an antibody specific for CD20. Based on the published data for anti-CD20 antibodies we expected it to exhibit higher anti-proliferative activity against CD20 expressing lymphoma cells than fusion proteins containing wild-type IFNα. However, instead we found that it was less effective (see FIG. 7).

Figure 8:
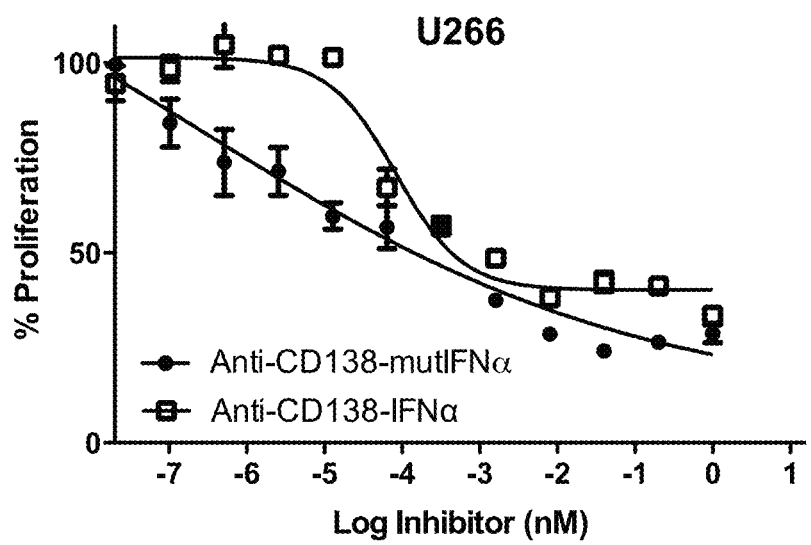
FIG. 8 comparison of anti-proliferative activity of anti-CD138-IFNα with anti-CD138-mut-IFNα.

When we changed the binding specificity of the fusion proteins containing mutIFNα from CD20 to CD138 (using an anti-CD138 antibody), to our surprise we found that they were more effective than those containing wild-type IFNα in inhibiting the proliferation of most myeloma cell lines. Shown in FIG. 8 are the results using myeloma cell line U266. Thus, anti-CD138-mutIFNα was more effective in inhibiting the proliferation of myeloma cells than anti-CD138-IFNα.

Figure 9:
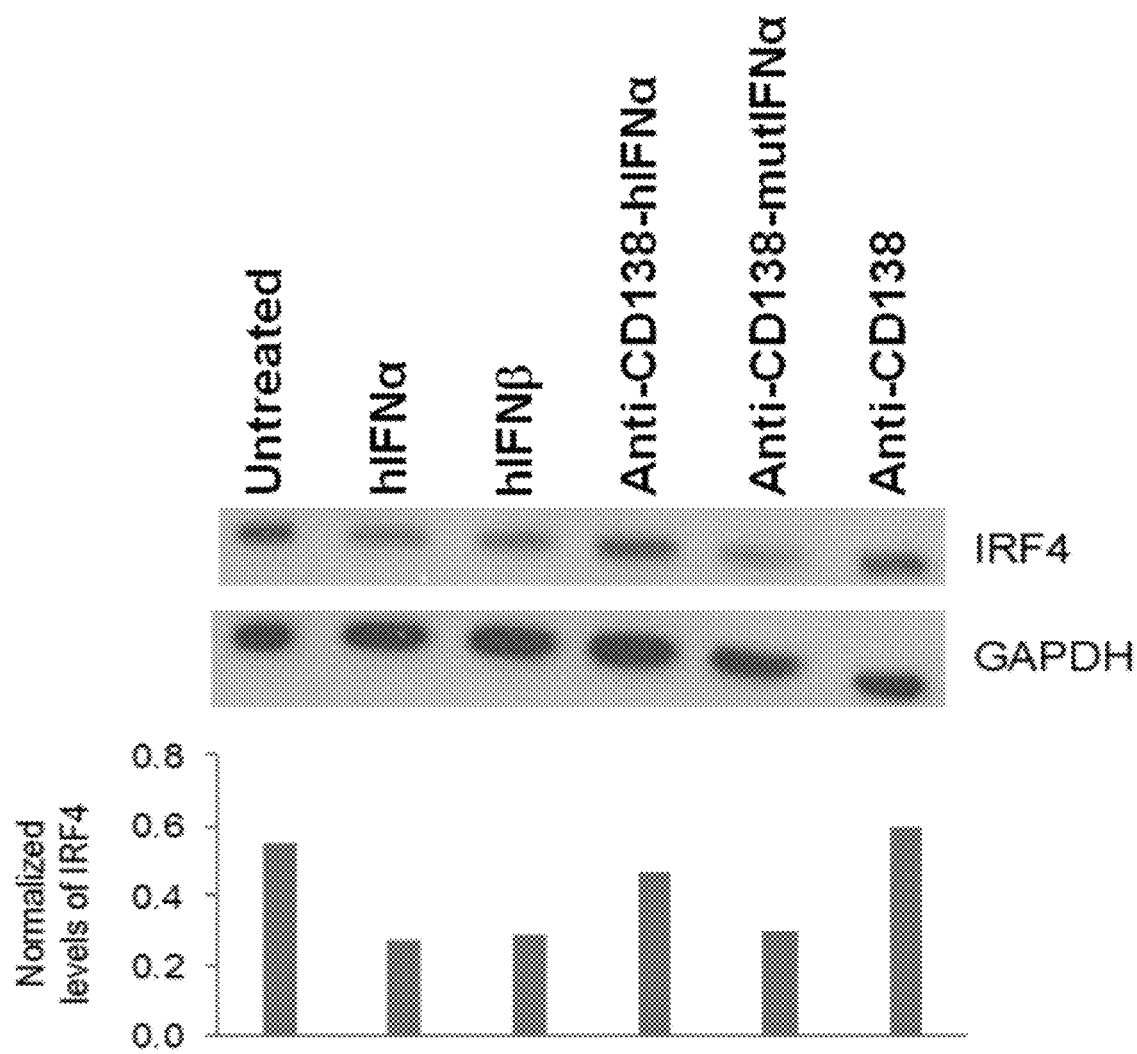
FIG. 9 shows a comparison of the ability the anti-CD138-mutIFNα and the anti-CD138-IFNα in inhibiting IRF4 protein expression in U266 cells. U266 cells were treated with 1 nM of the indicated proteins for 2 days and the expression level of IRF4 determined by Western blotting. After normalizing to GAPDH, the relative level of IRF4 expression was quantified using densitometry.

IRF4 is a protein shown to be essential for the survival of myeloma cells. The anti-CD138-mutIFNα construct was shown to be more effective than the anti-CD138-IFNα construct in inhibiting its expression in U266 cells (see, e.g., FIG. 9).

Figure 10:
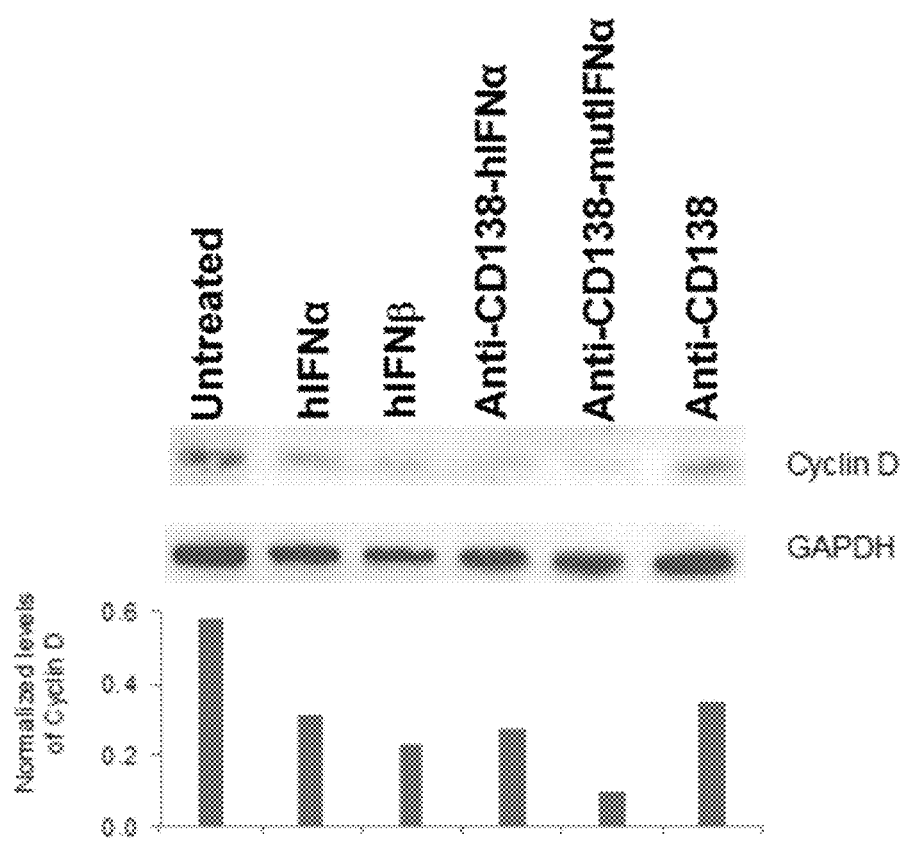
FIG. 10 shows a comparison of the ability the anti-CD138-mutIFNα and the anti-CD138-IFNα in inhibiting its expression of cyclin D expression in U266 cells. U266 cells were treated with 1 nM of the indicated proteins for 2 days and the expression level of cyclin D determined by Western blotting. After normalizing to GAPDH, the relative level of cyclin D expression was quantified using densitometry.

Increased expression of cyclin D has been shown to be associated with the growth of myeloma cells and anti-CD138-mutIFNα was shown to be more effective than anti-CD138-IFNα in inhibiting its expression in U266 cells (see FIG. 10).

Figure 11:
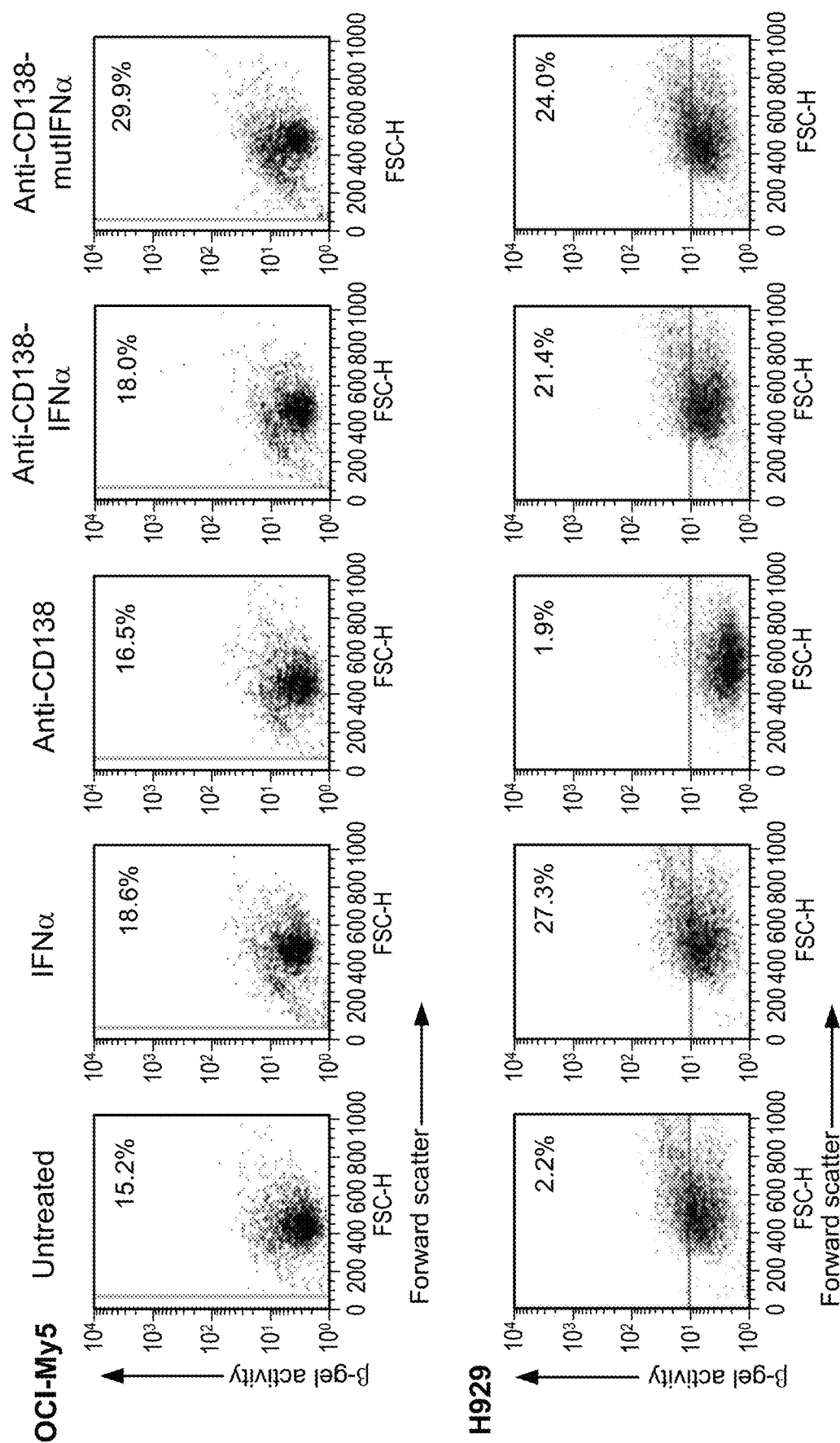
FIG. 11 shows a comparison of anti-CD138-mutIFNα2 and anti-CD138-IFNα2 in inducing senescence in H929 and OCI-My5 myeloma cells. Senescent cells are metabolically active in vitro, but do not divide. One common marker for the detection of senescence is beta galactosidase (β-gal) activity at pH 6, which is a barometer for increased lysosomal content of senescent cells. Cells were treated with 1 nM of the indicated proteins for 3 days. Cleavage of the substrate C12FDG was detected by flow cytometry as an indication of β-gal activity at pH 6. The percentage of cells with β-gal activity is shown.

Cellular senescence is one pathway for inhibiting tumor growth. Anti-CD138-mutIFNα was shown to be more effective than anti-CD138-IFNα in inducing cellular senescence in H929 and OCI-My5 myeloma cells (see FIG. 11).

Figure 12:
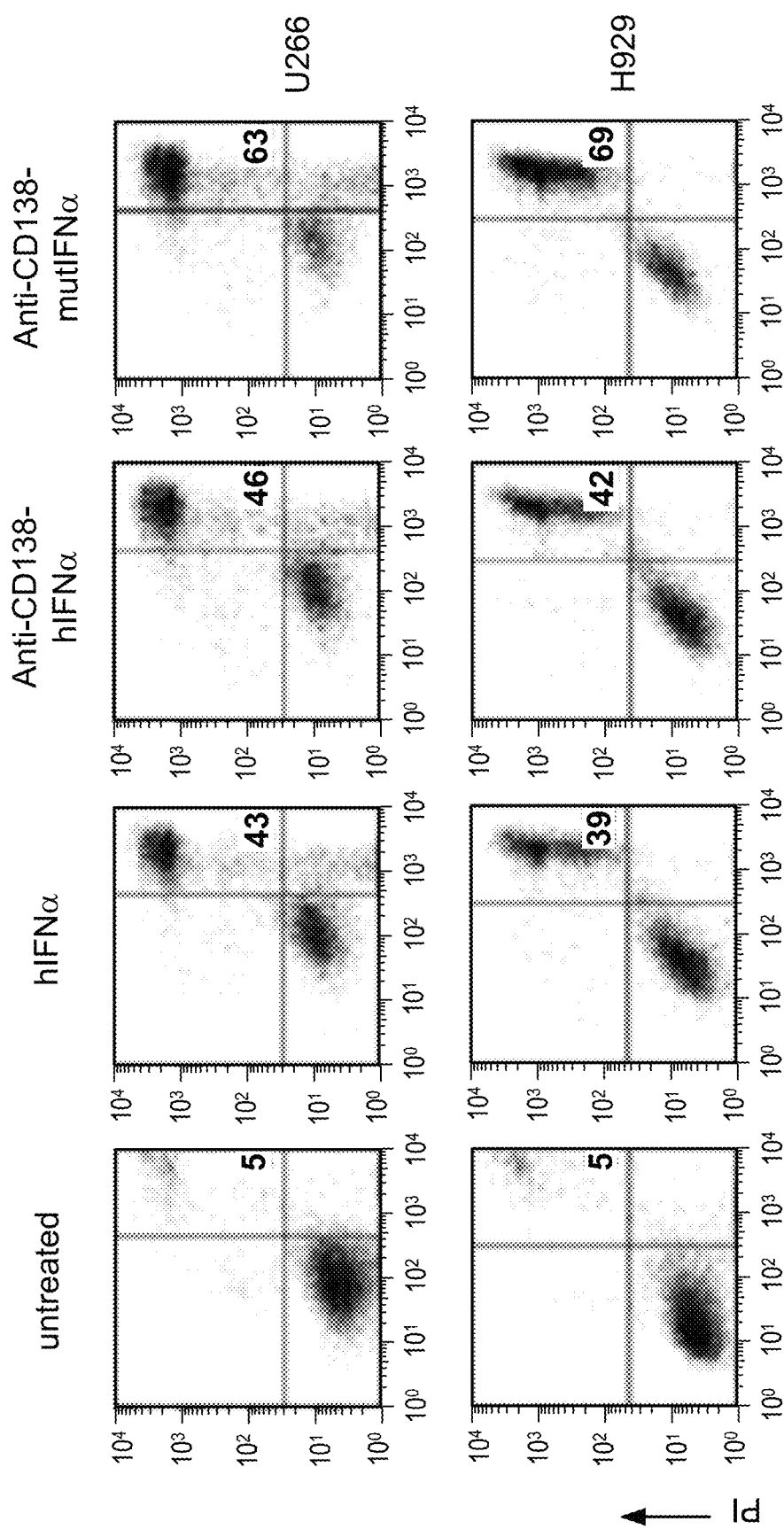
FIG. 12 shows a comparison of anti-CD138-mutIFNα2 and anti-CD138-IFNα2 in inducing apoptosis in U266 and H929 cells. Cell lines were treated with 500 pM of the indicated proteins for 3 days and the percentage of annexin V apoptotic cells was determined.

Apoptosis is one mechanism for inhibiting tumor growth. The anti-CD138-mutIFNα construct was shown to be more effective than the anti-CD138-IFNα construct in inducing apoptosis in U266 and H929 myeloma cells (see FIG. 12).

An important readout is which protein is most effective against primary myeloma cells. Anti-CD138-mutIFNα was shown to be more effective than anti-CD138-IFNα against primary myeloma cells from patients (see FIG. 5).

Figure 6A:
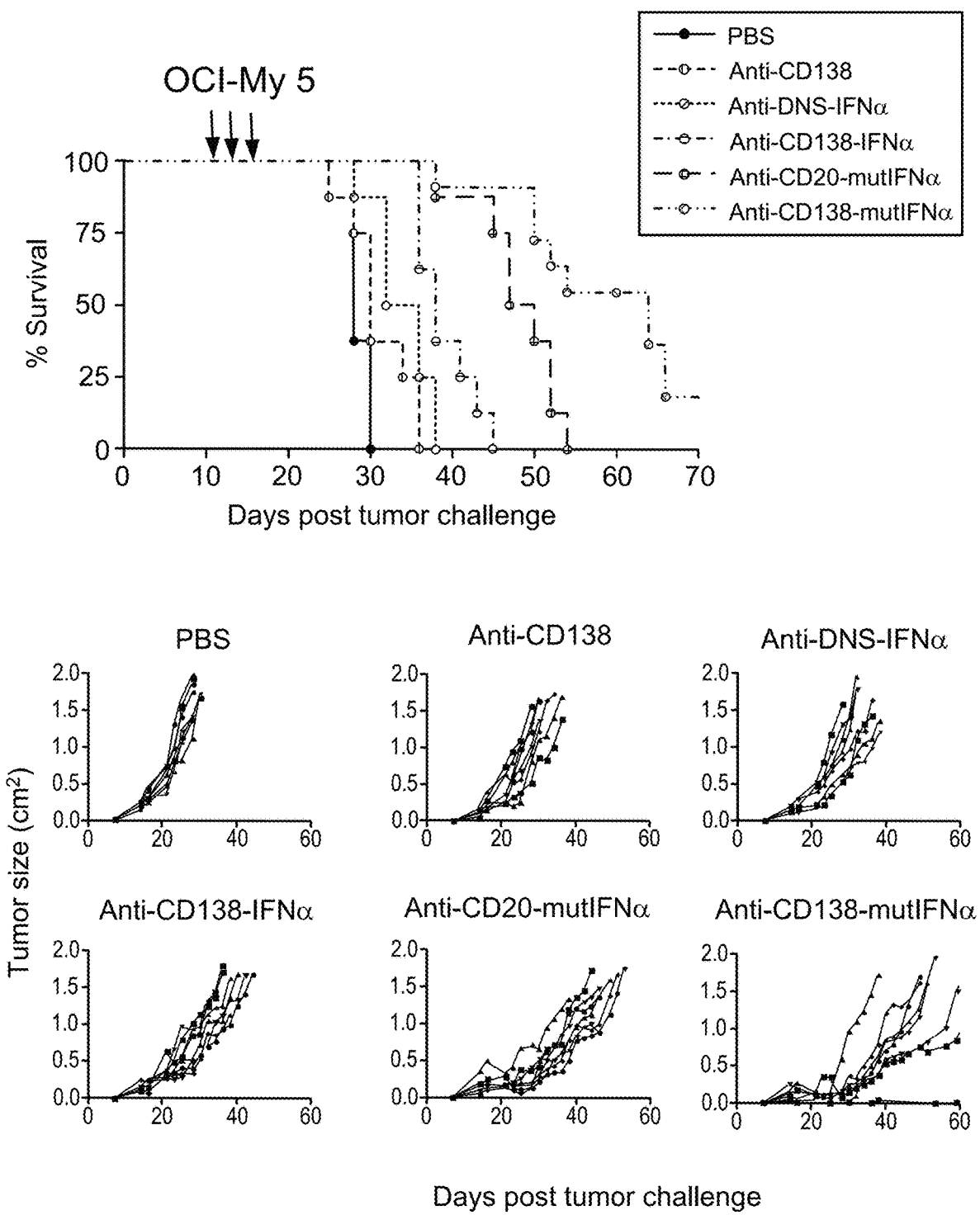
FIGS. 6A and 6B, show activity of anti-CD138, anti-CD138-IFNα anti-CD138-mutIFNα in a xenograft model of MM.
Figure 6B:
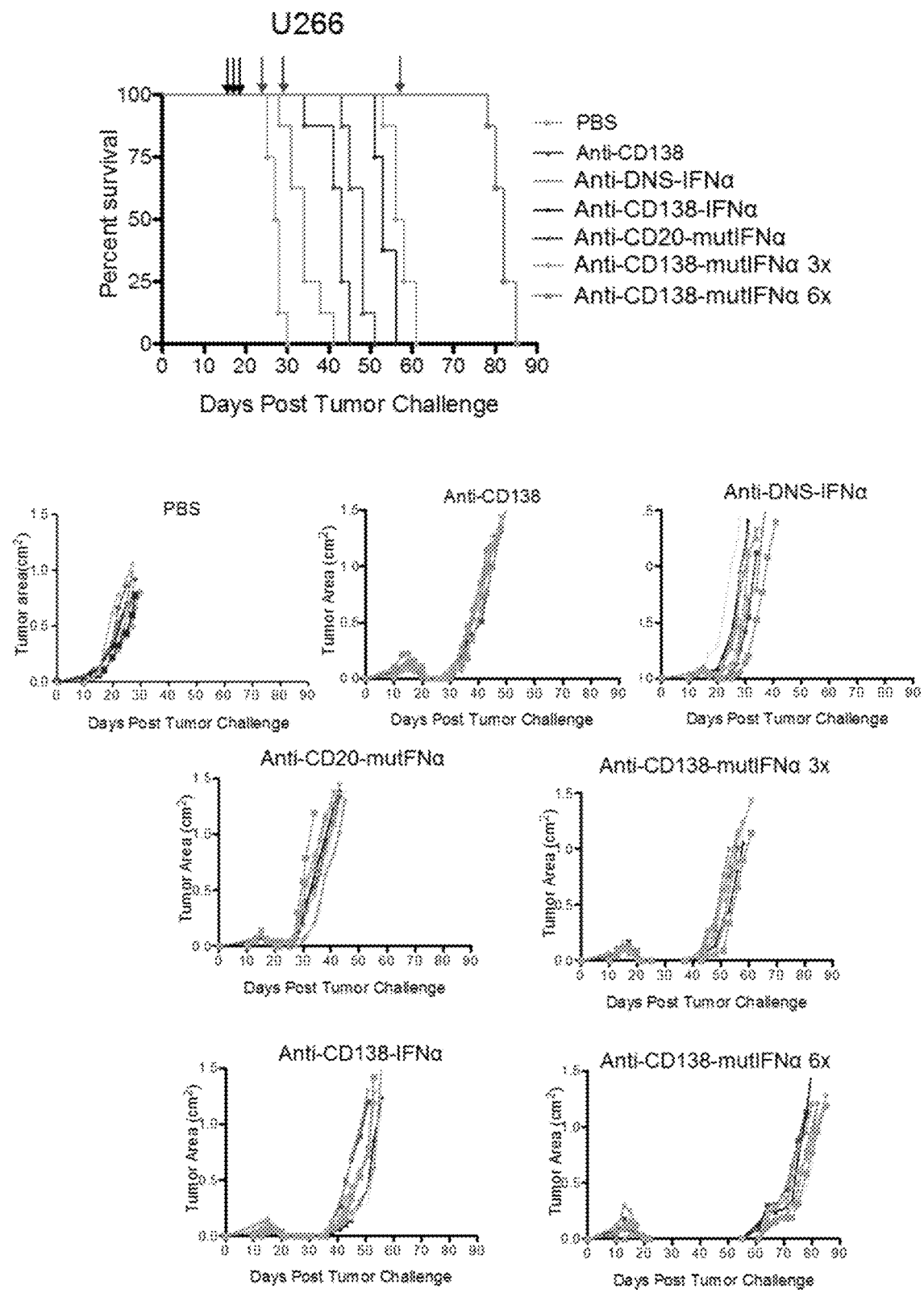

In vivo efficacy in a treatment model is very important. Anti-CD138-mutIFNα was shown to be more effective than anti-CD138-IFNα in treating tumors in mice bearing xenografts of either OCI-MY5 or U266 cells (see FIG. 6).

In view of these findings it is believed that anti-CD138-interferon constructs, and in particular anti-CD138-mutant interferon constructs show surprising and unexpected efficacy against cells expressing or over expressing CD138.

Thus, in certain embodiments, the constructs (e.g., chimeric moieties) comprising an interferon (e.g., IFN-α, IFNβ, mutant IFNα, mutant IFNβ, truncated IFNα, truncated IFNβ, etc.) attached to a targeting moiety (e.g., to an antibody that specifically binds CD138). The constructs include chemical conjugates as well as fusion proteins. Also provided are nucleic acids encoding the fusion proteins as well as cells transfected with the nucleic acids to express the fusion proteins. Also provided are methods of inhibiting growth and proliferation of cells that express or overexpress CD138 using the constructs described herein. In certain embodiments, the cells that express or over express CD138 are cancer cells. Accordingly in various embodiments, methods are provided for inhibiting, delaying and/or preventing the growth of a tumor and/or spread of malignant tumor cell using the constructs described herein. In addition, kits comprising the constructs are provided, e.g., for the treatment of various cancers.

I. Constructs comprising a targeting moiety attached to an interferon.

It was a surprising discovery that constructs (chimeric constructs) comprising a targeting moiety that binds (e.g., that preferentially or specifically binds) to CD138 attached to a native (wildtype) or modified IFN (e.g., mutant IFN-α) can be effectively used to inhibit the growth and/or proliferation of target cells (e.g., cancer cells) that express or overexpress CD138. In certain embodiments the CD138 targeting moieties are chemically conjugated to the interferon, while in other embodiments, the CD138 targeting moiety (or a component thereof) is expressed as a fusion protein with the interferon. When produced as a fusion protein the CD138 targeting moiety (e.g., antibody) (or a component thereof) can be directly fused to the interferon or attached by means of a peptide linker (e.g., a (Gly$_4$Ser)$_3$ (SEQ ID NO:1) linker, a Gly$_4$Ser (SEQ ID NO:2) linker, a SerGly$_4$Ser linker (SEQ ID NO:8), an AEAAAKEAAAKA (SEQ ID NO:15) linker, and the like.

A) CD138 Targeting moieties.

In various embodiments, the targeting moiety is a molecule that specifically or preferentially binds CD138 expressed, or overexpressed, by (e.g., on the surface of) or associated with the target cell(s) (e.g., cancer cells such as multiple myeloma cells). While essentially any cell that expresses or overexpresses CD138 can be targeted, certain preferred cells include those associated with a pathology characterized by hyperproliferation of a cell (i.e., a hyperproliferative disorder).

Hyperproliferative disorders characterized as cancer include but are not limited to solid tumors, proliferation of metastatic cells, and the like.

While the examples focus on the use of the constructs to inhibit/kill multiple myeloma cells, it has been recognized that CD138 is expressed/overexpressed in a number of other cancers. Thus for example, CD138 has been shown to be expressed/overexpressed on the following cancers: ovarian carcinoma, cervical cancer (Numa et al. (2002) *Int. J. Oncol.*, 20(1): 39-43.), endometrial cancer (Choi et al. (2007) *Int. J. Cancer,* 121(4): 741-750), kidney carcinoma, gall bladder, transitional cell bladder carcinoma, gastric cancer (Wiksten et al. (2008) *Gastric: Anticancer Res.* 28(4C): 2279-2287), prostate adenocarcinoma (Zellweger et al. (2003) *Prostate* 55(1): 20-29), mammary carcinoma (Loussouarn et al. (2008) *Br. J. Cancer,* 28: 1993-1998), non-small cell lung carcinoma (Shah et al. (2004) *Cancer* 101(7): 1632-1638), squamous cell lung carcinoma (Toyoshima et al. (2001) *Lung Cancer,* 31(2-3): 193-202), colon carcinoma cells and cells of Hodgkin's and non-Hodgkin's lymphomas, colorectal carcinoma (Hashimoto et al. (2008) *BMC Cancer* 8: 185), hepato-carcinoma (Li et al. (2005) *World J. Gastroenterol.* 11(10): 1445-1451), chronic lymphocytic leukemia (CLL), pancreatic (Conejo et al. (2000) Int. J. Cancer, 88(1): 12-20), and head and neck carcinoma (Anttonen et al. (1999) *Br. J. Cancer,* 79(3/4): 558-564) to name just a few. It is believed the methods described herein will be effective in these various cancers and others.

These disorders have been well characterized in humans, but also exist with a similar etiology in other mammals, and can be treated by administering the constructs described herein (alone or in the context of a combined treatment plan (e.g., in combination with radiation therapy and/or the use of other anti-cancer compounds).

Anti-CD138 Antibodies.

In certain embodiments, the targeting moieties can comprise antibodies, unibodies, or affybodies that specifically or preferentially bind CD138. Antibodies that specifically or preferentially bind CD138 are well known to those of skill in the art and many are commercially available. For example Wijdenes et al. (1996) *British Journal of Haematology,* 94, 318-323 describe an antibody that is specific for CD138 (syndecan-1) and this antibody is commercially available from Abcam, Miltenyi Biotec, and the like. Other illustrative and non-limiting anti-CD138 antibodies include, but are not limited to the polyclonal rabbit anti-human CD138 antibody LS-B3341 and the monoclonal mouse anti-Human CD138 Antibody LS-B4051 available from LifeSpan Biosciences, Inc., monoclonal antibody (MI15) available from Pierce Antibodies, Biotest BT-062 anti-CD138, and the like. Other anti-CD138 antibodies include, but are not limited to B-B2, 1D4, MI15 and 104-9 (see, e.g., Gattei et al. (1999) *British J. Haematol.,* 104(1): 152-162).

In addition, anti-CD138 antibodies can be made using methods well known to those of skill in the art. For example, antibodies can be produced by immunizing an animal with CD138 or an immunogenic fragment thereof and raising the antibodies in that animal. Polyclonal antibodies can be recovered and used or converted to monoclonal antibodies according to methods well known to those of skill in the art.

In certain embodiments, single chain anti-CD138 antibodies can be created using a phage display library. One such method is described by Fernandez et al. (2005) *Journal of Clinical Oncology*, 2005 ASCO Annual Meeting Proceedings. 23(16S), Part I of II (June 1 Supplement), 2005: 2550. The authors used combinatorial immunoglobulin (Ig) libraries with phage display to generate in vitro human Ig Fab fragments without the need to maintain on-going hybridoma culture. A library of $10^{10}$ clones from the cDNA of peripheral blood mononuclear cells of patients with adenocarcinoma were used to identify anti-CD138 specific Ig. Generally following removal of non-specific Fabs by exposing the Ig library to the epithelial cell line HEK, specific anti-CD138 Fabs were selected by exposing the Fab library to HEK transduced with human CD138. Six rounds of selection resulted in a panel of anti-CD138-bearing phage. The anti-CD138-bearing phages bound multiple myeloma CD138+ cell lines (U266, SBN) by ELISA analysis while phage alone did not. Sequencing the Fab VH and VL genes confirmed the heterogeneity of the panel of anti-CD138 Fabs.

The constructs described herein need not be limited to the use of the antibodies described above, and other such antibodies as they are known to those of skill in the art can be used in the constructs, formulations, and methods described herein.

In certain embodiments, the antibody has an affinity ($K_D$) for CD138 of at least $1 \times 10^{-6}$ M, or at least $1 \times 10^{-7}$ M, or at least $1 \times 10^{-8}$ M, or at least $1 \times 10^{-9}$ M, or at least $1 \times 10^{-10}$ M, or at least $1 \times 10^{-11}$ M.

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the construct is to be used. In other words, for use in a human, it is desirable to use a human, humanized, or chimeric human antibody.

While the above discussion pertains to antibodies, it will be recognized that affybodies and/or unibodies can be used instead of antibodies.

Unibodies.

UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule left only one area on the UniBody that can bind to a target. Methods of producing unibodies are described in detail in PCT Publication WO2007/059782, (see, also, Kolfschoten et al. (2007) *Science* 317: 1554-1557) and can be used to create unibodies based on any known anti-CD138 antibody.

Affibodies.

Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (see, e.g., Nord et al. (1997) *Nat. Biotechnol.* 15: 772-777; Ronmark et al. (2002) *Eur. J. Biochem.*, 269: 2647-2655.). Details of Affibodies and methods of production are known to those of skill (see, e.g., U.S. Pat. No. 5,831,).

B) Interferons

In various embodiments chimeric moieties of this invention comprise an interferon (e.g., IFN-α, IFNβ, etc.) joined to the targeting moiety (e.g., anti-CD138 antibody). The interferon can be a full length wild-type interferon (e.g. IFN-α, IFNβ, IFN-γ, etc.) an interferon fragment (e.g., an IFN-α fragment), and/or a mutated interferon. Typically the interferon fragment is one that possesses the endogenous binding affinity and/or activity of the native interferon, preferably at a level of at least 60%, or of at least 80%, more preferably at least 90% or 95%, most preferably at least 98%, 99%, 100%, or a level greater than the wild-type interferon (in its isolated form).

Means of identifying such modified interferon molecules are routine to those of skill in the art. In one illustrative approach, a library of truncated and/or mutated IFN-α is produced and screened for IFN-α activity. Methods of producing libraries of polypeptide variants are well known to those of skill in the art. Thus, for example error-prone PCR can be used to create a library of mutant and/or truncated IFN-α (see, e.g., U.S. Pat. No. 6,365,408).

The resulting library members can then be screened according to standard methods known to those of skill in the art. Thus, for example, IFN-α activity can be assayed by measuring antiviral activity against a particular test virus. Kits for assaying for IFN-α activity are commercially available (see, e.g., ILITE™ alphabeta kit by Neutekbio, Ireland).

In various embodiments use of a mutated interferon alpha 2 (IFNα2) is contemplated. Certain mutants include a mutation of the His at position 57, and/or the E at position 58, and/or the Q at position 61. In certain embodiments the mutants include the mutation H57Y, and/or E58N, and/or Q61S. In certain embodiments the mutants include a mutated IFNα2 having the mutations H57Y, E58N, and Q61S (YNS) (see, e.g., Kalie et al. (2007) *J. Biol. Chem.*, 282: 11602-11611).

In other embodiments mutants include a mutation of the His at position 57, and/or the E at position 58, and/or the Q at position 61 to A (alanine). In certain embodiments the mutants include a mutated IFNα2 having the mutations H57A, E58A, and Q61A (HEQ) (see, e.g., Jaitin et al. (2006) *Mol. Cellular Biol.*, 26(5): 1888-1897). In certain embodiments the mutant interferon comprises a mutation of His at position 57 to A, Y, or M, and/or a mutation of E at position 58 to A, or N, or D, or L, and/or a mutation of Q at position 61 to A, or S, or L, or D.

A mutated IFNβ comprising a serine substituted for the naturally occurring cysteine at amino acid 17 has also been demonstrated to show efficacy (see, e.g., Hawkins et al. (1985) *Cancer Res.*, 45, 5914-5920.

In various embodiments use of truncated interferons is also contemplated. Human INFα, for example, with deletions of the first 15 amino-terminal amino acid residues and/or the last 10-13 carboxyl-terminal amino acid residues, have been shown to exhibit virtually the same activity as the parent molecules (see, e.g., Ackerman (1984) *Proc. Natl. Acad. Sci., USA*, 81: 1045-1047). Accordingly the use of IFN-αs having 1, 2, 3, up to 13 carboxyl terminal amino acid residues deleted and/or 1, 2, 3, up to 15 amino terminal amino acid residues deleted are contemplated.

It has also been demonstrated that activity resides in huIFN-α fragment HuIFN-α (1-110) (Id.). Accordingly carboxyl truncated IFNs with truncations after residue 110 and/or with 1, 2, 3, up to 15 amino terminal amino acid residues deleted are contemplated.

Certain C-terminally truncated interferon betas (IFNβ) have been shown to have increased activity (see, e.g., U.S. Patent Publication 2009/0025106 A1). Accordingly, in certain embodiments the interferon used in the constructs described herein includes the C-terminally truncated IFNβ described as IFN-Δ1, IFN-Δ2, IFN-Δ3, IFN-Δ4, IFN-Δ5, IFN-Δ6, IFN-Δ7, IFN-Δ8, IFN-Δ9, or IFN-Δ10 as described in U.S. Patent Publication NO: 2009/0025106 A1. In certain embodiments the interferon is IFN-Δ7, IFN-Δ8, or IFN-Δ9 (SEQ ID NOs: 57, 59, and 61 in US 2009/0025106 A1 (see, Table 1).

example, N-terminal modifications including, but not limited to the addition of PEG, protecting groups, and the like. U.S. Pat. No. 5,824,784, for example, described N-terminally chemically modified interferon.

The foregoing interferons are intended to be illustrative and not limiting. Using the teaching provided herein, other suitable modified interferons (e.g., modified IFN-α, IFNβ, IFN-γ, etc.) can readily be identified and produced.

C. Attachment of the targeting moiety (e.g., anti-CD138 antibody) to the Interferon.

In various embodiments, the targeting moiety (e.g., an anti-CD138 antibody) and the interferon can be joined together in any order. Thus, for example, the antibody can be joined to either the amino or carboxy terminal of the interferon. The antibody can also be joined to an internal region of the interferon, or conversely, the interferon can be joined to an internal location or to any terminus of the

TABLE 1

Truncated IFnβ showing enhanced activity (see U.S. Patent Publication 2009/0025106 A1).

| Truncated IFN | Amino Acid Sequence | SEQ ID NO |
|---|---|---|
| IFN-Δ7 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn Leu Gln | 3 |
| IFN-Δ8 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn Leu | 4 |
| IFN-Δ9 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn | 5 |

In certain embodiments the use of chemically modified interferon is also contemplated. For example, in certain embodiments, the interferon is chemically modified to increase serum half-life. Thus, for example, (2-sulfo-9-fluorenylmethoxycarbonyl)$_7$-interferon-α2 undergoes time-dependent spontaneous hydrolysis, generating active interferon (see, e.g., Shechter et al. (2001) *Proc. Natl. Acad. Sci., USA,* 98(3): 1212-1217). Other modifications, include for antibody, as long as the attachment does not interfere with binding of the antibody to that target marker (e.g., CD138).

The antibody and the interferon (e.g., IFN-α, IFNβ, etc.) can be attached by any of a number of means well known to those of skill in the art. In certain embodiments, the interferon is conjugated, either directly or through a linker (spacer), to the antibody. In certain embodiments, however, it is preferable to recombinantly express the construct as a fusion protein (e.g., with a single chain antibody, or with one chain of a multi-chain antibody).

i) Chemical conjugation of the targeting moiety to the interferon.

In certain embodiments, the targeting moiety (e.g., an anti-CD138 antibody) is chemically conjugated to the interferon (e.g., IFN-α, IFNβ, mutIFNα, etc.) molecule. Means of chemically conjugating molecules are well known to those of skill.

The procedure for conjugating two molecules varies according to the chemical structure of the agent. Polypeptides typically contain a variety of functional groups; e.g., carboxylic acid (COOH) or free amine (—$NH_2$) groups that are available for reaction with a suitable functional group on the other peptide, or on a linker to join the molecules thereto.

Alternatively, the antibody and/or the IFN-α can be derivatized to expose or attach additional reactive functional groups. The derivatization can involve attachment of any of a number of linker molecules such as those available from Pierce Chemical Company, Rockford Ill.

A "linker", as used herein, typically refers to a molecule that is used to join the antibody to the interferon. In various embodiments, the linker is capable of forming covalent bonds to both the antibody and to the interferon. Suitable linkers are well known to those of skill in the art and include, but are not limited to, straight or branched-chain carbon linkers, heterocyclic carbon linkers, or peptide linkers. In certain embodiments, the linker(s) can be joined to the constituent amino acids of the antibody and/or the interferon through their side groups (e.g., through a disulfide linkage to cysteine). In certain preferred embodiments, the linkers are joined to the alpha carbon amino and/or carboxyl groups of the terminal amino acids of the antibody and/or the interferon.

A bifunctional linker having one functional group reactive with a group on the antibody and another group reactive on the interferon, can be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No.: 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine,* Academic Press, pp. 168-190 (1982); Waldmann (1991) *Science,* 252: 1657; U.S. Pat. Nos. 4,545,985 and 4,894,443, and the like.

ii) Production of fusion proteins.

In certain embodiments, a chimeric targeting moiety-interferon fusion protein is synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins or encoding one chain of the antibody attached to an interferon can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862); the solid support method of U.S. Pat. No. 4,458,066, and the like.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins can be cloned using DNA amplification methods such as polymerase chain reaction (PCR). Thus, for example, the gene for IFN-α is PCR amplified, using a sense primer containing the restriction site for, e.g., NdeI and an antisense primer containing the restriction site for HindIII. This can produce a nucleic acid encoding the mature IFN-α sequence and having terminal restriction sites. An antibody having "complementary" restriction sites can similarly be cloned and then ligated to the IFN-α and/or to a linker attached to the IFN-α. Ligation of the nucleic acid sequences and insertion into a vector produces a vector encoding IFN-α joined to the anti-CD138 antibody.

While the two molecules can be directly joined together, one of skill will appreciate that the molecules can be separated by a peptide spacer consisting of one or more amino acids. Generally the spacer will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity.

It was a surprising discovery, however, that certain linkers are unsuitable for preparation of fusion proteins of the present invention. Thus, for example, the $(Gly_4Ser)_3$ (SEQ ID NO:1) linker was not well suited for the production of an anti-CD20-IFN-α construct. Without being bound to a particular theory, it is believed the interferon was being removed from the fusion protein by proteolysis. Western blot analysis using anti-Fc and anti-interferon, confirmed that both of the upper bands were heavy chains, but only the largest contained interferon.

Accordingly, in certain preferred embodiments, it is desirable to use a linker that is resistant to proteolysis. Certain preferred linkers are linkers that are not the $(Gly_4Ser)_3$ (SEQ ID NO:6) linker. Certain preferred linkers are linkers shorter than 15 amino acids, or linkers shorter than 14, 13, 12, 11, 10, 9, 8, 7, 6, 5, 4, 3, or 2 amino acids in length. In certain embodiments the linker is an alpha helical linker ranging in length up to about 12 or 13 or 14 amino acids in length.

Certain illustrative proteolysis-resistant linkers well suited for use in the constructs of this invention are shown in Table 2.

TABLE 2

Illustrative proteolysis-resistant linkers.

| Linker Seq | SEQ ID NO |
|---|---|
| GGG | |
| GGS | |
| GGGGS | 7 |
| SGGGGS | 8 |
| GGGGSGGGGS | 9 |
| A EAAAK A | 10 |
| A EAAAK EAAAK A | 11 |
| A EAAK EAAAK EAAAK A | 12 |
| A EAAAK EAAAK EAAAK EAAAK A | 13 |
| A EAAAK EAAAK EAAAK EAAAK EAAAK A | 14 |
| AEAAAKEAAAKAG | 15 |
| AEAAAKEAAAKAGS | 16 |
| GGGGG | 17 |
| GGAGG | 18 |
| GGGGGGG | 19 |
| GAGAGAGAGA | 20 |
| RPLSYRPPFPFGFPSVRP | 21 |
| YPRSIYIRRRHPSPSLTT | 22 |
| TPSHLSHILPSFGLPTFN | 23 |
| RPVSPFTFPRLSNSWLPA | 24 |
| SPAAHFPRSIPRPGPIRT | 25 |
| APGPSAPSHRSLPSRAFG | 26 |
| PRNSIHFLHPLLVAPLGA | 27 |
| MPSLSGVLQVRYLSPPDL | 28 |
| SPQYPSPLTLTLPPHPSL | 29 |
| NPSLNPPSYLHRAPSRIS | 30 |
| LPWRTSLLPSLPLRRRP | 31 |
| PPLFAKGPVGLLSRSFPP | 32 |
| VPPAPVVSLRSAHARPPY | 33 |
| LRPTPPRVRSYTCCPTP | 34 |
| PNVAHVLPLLTVPWDNLR | 35 |
| CNPLLPLCARSPAVRTFP | 36 |
| LGTPTPTPTPTGEF | 37 |
| EDFTRGKL | 38 |
| L EAAAR EAAAR EAAAR EAAAR | 39 |
| L EAAAR EAAAR EAAAR | 40 |
| L EAAAR EAAAR | 41 |
| L EAAAR | 42 |
| EAAAR EAAAR EAAAR EAAAR | 43 |
| EAAAR EAAAR EAAAR | 44 |
| EAAAR EAAAR | 45 |
| EAAAR | 46 |

The nucleic acid sequences encoding the fusion proteins can be expressed in a variety of host cells, including E. coli, other bacterial hosts, yeast, and various higher eukaryotic cells such as the COS, CHO and HeLa cells lines and myeloma cell lines. The recombinant protein gene is typically operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification,* Springer-Verlag, N.Y.: Deutscher (1990) *Methods in Enzymology Vol. 182: Guide to Protein Purification.*, Academic Press, Inc. N.Y., and the like). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein (e.g., anti-CD138-IFN-α, anti-CD138-mutIFN-α, etc.) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.,* 268: 14065-14070; Kreitman and Pastan (1993) *Bioconjug. Chem.,* 4: 581-585; and Buchner, et al. (1992) *Anal. Biochem.,* 205: 263-270). Debinski et al., for example, describe the denaturation and reduction of inclusion body proteins in guanidine-DTE. The protein is then refolded in a redox buffer containing oxidized glutathione and L-arginine.

In certain embodiments a transient expression system can be used to express the chimeric constructs described herein. Although many cell lines potentially can be used, one cell line that works well for transient expression is 293T. For transient expression of 293T on Day 0, 9 million cells in 25 ml are seeded for each 150 mm tissue culture plate. A 1 mg/ml of PEI (Polyethylenimine) is made using sterile water. For the expression of a complete antibody or antibody fusion protein, 25 μg each of H and L (50 ug total) is used per plate. A volume of 5 ml is used for transfection of each 150 mm plate. The DNA is mixed with DMEM, the PEI is then added and the mixture is incubated at room temperature for 10 mins. 1.75 μg PEI is used for each ug of DNA. For transfection, the old medium is removed, discarded and replaced with 20 ml of fresh medium (Iscoves+5% calf serum). The transfection mix is added and the plate is swirled. On Day 2, the medium is replaced with 30 ml of Iscoves medium containing 1% FBS (fetal bovine serum) to minimize the amount of bovine Ig present. Supernatants are collected from the cells on Days 4,6 and 13 by removing the medium and replacing it with 30 ml of fresh Iscoves containing 1% FBS.

The cloning and expression of an anti-CD138-IFN-α fusion protein is illustrated herein in Example 1.

One of skill would recognize these expression methods are illustrative and not limiting. Modifications can be made to the fusion proteins described herein without diminishing their activity/efficacy. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Other modifications can be made to increase serum half-life and/or bioavailability. Such modifications include, but are not limited to the incorporation of D amino acids (especially in the linker), the use of non-naturally occurring amino acids, pegylation of the fusion protein, and the like.

D. Other Multi-valent targeting moieties.

In certain embodiments this invention contemplates the use of multivalent, preferably trivalent, quadravalent, pentavalent or greater targeting moieties to target the interferon to a target cell.

For example, multivalent anti-CD138 moieties can be produced by any of a number of methods. For example, linkers having three, four, or more reactive sites can be reacted with anti-CD138 antibodies to form a trimer or greater conjugate.

In certain embodiments, phage display, yeast display, bacterial display, or other display systems can be used to express and display multiple copies (e.g., at least 3, at least 4, at least 5, at least 6 copies, etc.) of a targeting antibody (e.g., anti-CD138 such as B-B4) and thereby effectively provide a multivalent targeting moiety.

In certain embodiments the use of diabodies and triabodies (e.g., comprising two domains that bind CD-138 or one domain that binds CD138 and another domain that binds, for example, a member of the EGFR receptor family (e.g., EGFR, HER3, etc.). Typically, diabodies comprise a heavy (VH) chain variable domain connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites (see, e.g., Holliger et al. (1993) *Proc. Natl. Acad. Sci.*, 90: 6444-6448). In certain embodiments to construct bispecific diabodies the V-domains of antibody A and antibody B are fused to create the two chains VHA-VLB, VHB-VLA. Each chain is inactive in binding to antigen, but recreates the functional antigen binding sites of antibodies A and B on pairing with the other chain.

II. Combined uses.

The constructs described herein are useful for inhibiting the growth and/or proliferation of target cells (e.g., cancer cells). In various embodiments the constructs can be used to inhibit disease progression, to reduce the rate of secondary tumor formation, to shrink tumor size, and/or to stabilize regression/remission.

Particularly in the treatment of cancer, the constructs, formulations, and methods described herein may also include additional therapeutic and/or pharmacologically acceptable agents. For instance, the constructs, formulations, or methods may involve other agents for the treatment of cancer. Such agents include, but are not limited to alkylating agents (e.g., mechlorethamine (Mustargen), cyclophosphamide (Cytoxan, Neosar), ifosfamide (Ifex), phenylalanine mustard; melphalen (Alkeran), chlorambucol (Leukeran), uracil mustard, estramustine (Emcyt), thiotepa (Thioplex), busulfan (Myerlan), lomustine (CeeNU), carmustine (BiCNU, BCNU), streptozocin (Zanosar), dacarbazine (DTIC-Dome), cis-platinum, cisplatin (PLATINOL® (cisplatin), PLATINOL® (cisplatin) AQ), carboplatin (Paraplatin), altretamine (Hexalen), etc.), antimetabolites (e.g. methotrexate (Amethopterin, Folex, Mexate, Rheumatrex), 5-fluoruracil (Adrucil, Efudex, Fluoroplex), floxuridine, 5-fluorodeoxyuridine (FUDR), capecitabine (Xeloda), fludarabine: (Fludara), cytosine arabinoside (Cytaribine, Cytosar, ARA-C), 6-mercaptopurine (Purinethol), 6-thioguanine (Thioguanine), gemcitabine (Gemzar), cladribine (Leustatin), deoxycoformycin; pentostatin (Nipent), etc.), antibiotics (e.g. doxorubicin (Adriamycin, Rubex, Doxil, Daunoxome-liposomal preparation), daunorubicin (Daunomycin, Cerubidine), idarubicin (Idamycin), valrubicin (Valstar), mitoxantrone (Novantrone), dactinomycin (Actinomycin D, Cosmegen), mithramycin, plicamycin (Mithracin), mitomycin C (Mutamycin), bleomycin (Blenoxane), procarbazine (Matulane), etc.), mitotic inhibitors (e.g. paclitaxel (Taxol), docetaxel (Taxotere), vinblatine sulfate (Velban, Velsar, VLB), vincristine sulfate (Oncovin, Vincasar PFS, Vincrex), vinorelbine sulfate (Navelbine), etc.), chromatin function inhibitors (e.g., topotecan (Camptosar), irinotecan (Hycamtin), etoposide (VP-16, VePesid, Toposar), teniposide (VM-26, Vumon), etc.), hormones and hormone inhibitors (e.g. diethylstilbesterol (Stilbesterol, Stilphostrol), estradiol, estrogen, esterified estrogens (Estratab, Menest), estramustine (Emcyt), tamoxifen (Nolvadex), toremifene (Fareston) anastrozole (Arimidex), letrozole (Femara), 17-OH-progesterone, medroxyprogesterone, megestrol acetate (Megace), goserelin (Zoladex), leuprolide (Leupron), testosteraone, methyltestosterone, fluoxmesterone (Android-F, Halotestin), flutamide (Eulexin), bicalutamide (Casodex), nilutamide (Nilandron), etc.), inhibitors of synthesis (e.g., aminoglutethimide (Cytadren), ketoconazole (Nizoral), etc.), immunomodulators (e.g., RITUXIMAB® (Rituxan), trastuzumab (HERCEPTIN®), denileukin diftitox (Ontak), levamisole (Ergamisol), bacillus Calmette-Guerin, BCG (TheraCys, TICE BCG), interferon alpha-2a, alpha 2b (Roferon-A, Intron A), interleukin-2, aldesleukin (ProLeukin), etc.) and other agents such as 1-aspariginase (Elspar, Kidrolase), pegaspasgase (Oncaspar), hydroxyurea (Hydrea, Doxia), leucovorin (Wellcovorin), mitotane (Lysodren), porfimer (Photofrin), tretinoin (Veasnoid), and the like.

III. Pharmaceutical Compositions.

In certain embodiments, in order to carry out the methods described herein, one or more active agents (constructs described herein) are administered, e.g. to an individual diagnosed as having (or at risk for) a cancer. The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents (e.g., constructs) described herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., atherosclerosis and/or symptoms thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

In various embodiments the active agents (e.g., constructs) described herein are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the constructs described herein or formulations comprising such constructs are administered to a subject, e.g., to patient suffering e.g. from a cancer, or at risk of cancer (e.g. after surgical removal of a primary tumor) in an amount sufficient to prevent and/or cure and/or or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of active agent(s) can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects.

In certain embodiments, the active agents (e.g., constructs described herein) are administered orally (e.g. via a tablet) or as an injectable in accordance with standard methods well known to those of skill in the art. In other preferred embodiments, the constructs may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

In certain embodiments elevated serum half-life can be maintained by the use of sustained-release protein "packaging" systems. Such sustained release systems are well known to those of skill in the art. In one preferred embodiment, the ProLease™ biodegradable microsphere delivery system for proteins and peptides (see, e.g., Tracy (1998) Biotechnol. Prog. 14: 108; Johnson et al. (1996), Nature Med. 2: 795; Herbert et al. (1998), Pharmaceut. Res. 15, 357) a dry powder composed of biodegradable polymeric microspheres containing the active agent in a polymer matrix that can be compounded as a dry formulation with or without other agents.

The ProLease™ microsphere fabrication process was specifically designed to achieve a high encapsulation efficiency while maintaining integrity of the active agent. The process consists of (i) preparation of freeze-dried drug particles from bulk by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the active agents, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

IV. Kits.

In certain embodiments, kits for the treatment of a primary cancer and/or in an adjunct therapy are provided. In various embodiments the kits typically comprise a container containing a construct described herein (e.g., anti-CD138-IFNα, anti-138-mutIFNα, anti-CD138-IFNβ, etc.). In various embodiments the construct can be present in a pharmacologically acceptable excipient.

In addition the kits can optionally include instructional materials disclosing means of use of the chimeric moiety (e.g. to treat a cancer and/or as an adjunct therapeutic). The instructional materials may also, optionally, teach preferred dosages, counter-indications, and the like.

The kits can also include additional components to facilitate the particular application for which the kit is designed. Thus, for example, in certain embodiments, the kit can additionally contain one or more additional anti-cancer drugs (e.g., doxirubicin, vinblastine, etc.), and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Anti-CD138-IFNα and Anti-CD138-mutIFNα Constructs Demonstrate Potent Apoptotic and Anti-Tumor Activities Against Multiple Myeloma Materials and Methods Cell Lines HMCL cell lines were cultured in RPMI 1640 (Invitrogen, Carlsbad, Calif.) supplemented with 5% fetal calf serum (FCS; Atlanta Biologics, Lawrenceville, Ga.). ANBL-6 cells were cultured as described with the addition of 2 ng/mL of IL-6. Chinese Hamster Ovary (CHO) cells were cultured in IMDM supplemented with 5% FCS. Daudi cells were purchased from ATCC and grown in RPMI 1640 supplemented with 2 mM L-glutamine, 500 μM β-mercaptoethanol, and 10% FCS.

Construction of Expression Vectors

The heavy and light chain variable region amino acid sequences of an anti-CD138 antibody were obtained from US Patent Publication No: 2009/0175,863, which is incorporated herein by reference for the antibodies, and amino acid sequences (e.g., VH and VL sequences) described herein. A signal peptide with the amino acids MGWSYIIL-FLVATATGVHS (SEQ ID NO:47) was added 5' of the heavy chain variable region. Similarly, a signal peptide with the amino acids MKSQTQVFIFLLLCVSGAHG (SEQ ID NO:48) was added 5' of the light chain variable region. The amino acid sequences were sent to DNA 2.0 for custom DNA synthesis using codons optimized for CHO expression. The nucleotide sequence 5' GGATATCCACC 3' (SEQ ID NO:49), containing a Kozak ribosomal recognition site, was also added 5' of each sequence to facilitate downstream cloning. To further facilitate downstream cloning, the sequence 5' GCTAGCC 3' (SEQ ID NO:50) was added 3' of the heavy chain variable region, and the sequence 5' CGTAAGTCGACG 5' (SEQ ID NO:51) was added 3' of the light chain variable region.

The heavy chain variable region flanked by EcoRV and NheI restriction sites was sequence verified and cloned into an expression vector containing IgG1 alone, or IgG1 fused to human interferon alpha (hIFNα). The light chain variable region flanked by EcoRV and SalI restriction sites was also sequence verified before cloning into an expression vector containing a human kappa constant region.

```
VH sequence:
                              (SEQ ID NO: 52)
M G W S Y I I L F L V A T A T G V H S Q V Q L Q Q

S G S E L M M P G A S V K I S C K A T G Y T F S

N Y W I E W V K Q R P G H G L E W I G E I L P G T

G R T I Y N E K F K G K A T F T A D I S S N T V Q

M Q L S S L T S E D S A V Y Y C A R R D Y Y G N

F Y Y A M D Y W G Q G T S V T V S S

VL sequence:
                              (SEQ ID NO: 53)
M K S Q T Q V F I F L L L C V S G A H G D I Q M T

Q S T S S L S A S L G D R V T I S C S A S Q G I N

N Y L N W Y Q Q K P D G T V E L L I Y Y T S T L Q

S G V P S R F S G S G S G T D Y S L T I S N L E P

E D I G T Y Y C Q Q Y S K L P R T F G G G T K L E

I K
```

To construct anti-CD138-mutIFNα, nested polymerase chain reaction (PCR) was used to introduce three amino acid mutations—H57Y, E58N, and Q61S. The first round of PCR was done using the forward primer 5'-CGC GGA TCC TGT GAT CTG CCT CAA ACC CAC-3' (SEQ ID NO:54) and reverse primer 5'-CCT CTA GAA TCA TTC CTT ACT TCT TAA ACT-3' (SEQ ID NO:55). The nested PCR was done using forward primer 5'-CCTGTCCTCTACAATATGATCT-CACAGATCTTC-3' (SEQ ID NO:56) and reverse primer 5'-GAAGATCTGTGAGATCATATTGTAGAGGACAGG-3' (SEQ ID NO:57), which contain the mutations to IFNα. The insert was cloned into pCR2.1-TOPO vector (Invitrogen) and DNA sequence was verified. The XbaI/BamHI fragment containing the mutIFNα sequence was cloned into an anti-CD20 human γ1 H chain-IFNβ fusion vector pAH6747, yielding pAH11015. The BamHI/AvrII fragment from pAH11015 was then used to replace the wild-type IFNα sequence from expression vector pAH6905, which contains the anti-CD138 $V_H$ yielding vector pAH11016.

Protein Production and Purification

Fusion proteins were produced in CHO cells by transfection of H and L chain expression vectors. Stably transfected cells were isolated by selection on histidinol. For IgG and IgG fusion protein production, cells were seeded into roller bottles. At confluency, cells were expanded to 100 mL with IMDM+1% Fetal Clone (Thermo Fisher, Waltham, Mass.). The supernatant was removed every 2-3 days and replaced with fresh medium. Cell free culture supernatants were then passed through a protein A-Sepharose 4B fast flow column (Sigma-Aldrich, St. Louis, Mo.) and the bound protein eluted with 0.1 M citric acid, pH 3.5. Eluted fractions were neutralized immediately with 2 M Tris-HCl pH 8.0. Fractions were run on SDS-PAGE gels and stained with Coomassie blue to verify protein purity and integrity. Concentrations of proteins were determined using the BCA assay (Pierce, Rockford, Ill.). Anti-CD20-IFNα used as untargeted control protein was produced as described previously (Xuan et al. (2010) *Blood*, 115: 2864-2871).

Cell Viability Assay

HMCLs were seeded in 96-well plates and incubated with 0.00002 pM-25 nM of anti-CD20-IFNα, IFNα, anti-CD138-IFNα or anti-CD138-mutIFNα or anti-CD138-IFNα at 37° C. in a 5% $CO_2$ atmosphere for 3, 4 or 7 days. Percent cell viability was determined using MTS solution (Promega, Madison, WI) by measuring absorbance at 490 nm using a Synergy HT Multi-Detection Microplate Reader (BioTek Instruments, Inc., Winooski, Vt.) with untreated cells being 100%. GraphPad Prism (GraphPad Software Inc., La Jolla, Calif.) was used to analyze data by non-linear regression with the log (inhibitor) vs. the response with a variable slope with the $IC_{50}$ calculated. Data are expressed as a percentage of maximum metabolic activity. The experiments were performed in triplicate.

Apoptosis Assay

Cells were incubated with 500 pM of IFNα, anti-CD138-IFNα or anti-CD138-mutIFNα for 3 days and stained with Alexa Fluor 488 labeled Annexin V and propidium iodide (PI) using the Vybrant Apoptosis Kit #2 (Molecular Probes, Carlsbad, Calif.) as per manufacturer's instructions. Cells were analyzed by flow cytometry using FlowJo software.

Cell Cycle Analysis

Cells were treated with 500 pM of IFNα, anti-CD138-IFNα, or anti-CD138-mutIFNα for 4 days. Cells were incubated with 1 ml of hypotonic DNA staining buffer (1 mg/ml sodium citrate, 100 μg/ml PI, 20 μg/ml RNase A, and 0.3% Triton X-100 in $dH_2O$) for 30-60 min at 4° C. in the dark. Cells were analyzed by flow cytometry and cell cycle analysis performed using FlowJo software with the Watson Model.

Cell Proliferation Assay

Cells were treated for 3 days with 0.3 pM-25 nM IFNα, anti-CD138-IFNα, or anti-CD138-mutIFNα. The proliferative status of the cells was determined by measuring $^3[H]$-thymidine incorporation.

β-gal Activity as a Marker for Senescent Cells

Senescence induced β-galactosidase (β-gal) activity was detected as described previously (Debacq-Chainiaux et al.

(2009) *Nature Protocols,* 4: 1798-1806). Briefly, cells were treated with 1 nM of anti-CD138 IgG, anti-CD138-IFNα or anti-CD138-mutIFNα for 3, 4, 6 or 7 days. To induce lysosomal alkalinization, cells were incubated in 100 nM bafilomycin A1 (Sigma) for 1 h. Then cells were incubated for 30 min with the β-gal substrate dodecanoylaminofluorescein di-β-D-galactopyranoside ($C_{12}FDG$; Invitrogen), which becomes fluorescent after cleavage by β-gal. After washing twice with cold PBS, cells were resuspended in cold PBS containing 1 mM phenylethyl thiogalactoside (PETG), a β-gal inhibitor, and analyzed by flow cytometry for $C_{12}$-fluorescein.

Treatment of Primary MM Cells from Patients

Patients with active myeloma were biopsied while off therapy and myeloma cells isolated by negative antibody selection to >95% purity. Cells were incubated with 25 or 100 nM of anti-CD138 IgG, anti-CD138-IFNα or anti-CD138-mutIFNα for 24, 48 or 72 h. Trypan blue and MTT assays were used to determine the number of viable cells. The percentage of viable recovered cells was calculated based upon the number of viable cells recovered from DMSO-treated control cells, which was arbitrarily designated as 100%.

Western Blots

Cells were treated for 48 h with anti-CD138, IFNα, IFNβ, anti-CD138-IFNα, or anti-CD138-mutIFNα. Cells were lysed using RIPA buffer (50 mM Tris HCl pH 8, 150 mM NaCl, 1% NP-40, 0.5% sodium deoxycholate, 0.1% SDS) containing a protease inhibitor cocktail (Roche Applied Science, Indianapolis, Ind.). The cytosolic fractions were reduced with β-mercaptoethanol and separated by SDS-PAGE. Following transfer to nitrocellulose membrane (Whatman, Piscataway, N.J.) and blocking, samples were incubated with the following primary rabbit antibodies: anti-IRF4 (Epitomics, Berlingham, Calif.), anti-glyceraldehyde-3-phosphate dehydrogenase (GAPDH; Sigma), anti-ppRb Ser807/811 (Santa Cruz Biotechnology, Santa Cruz, Calif.), anti-cyclin D (Millipore, Billerica, Mass.), or anti-β tubulin (Abcam, Cambridge, Mass.). Secondary anti-rabbit IgG-HRP (GE Healthcare, Billerica, Mass.) was used and the blots were developed using enhanced chemiluminescence (ECL; Thermo Scientific, Waltham, Mass.).

In Vivo Anti-Tumor Activity Against OCI-My 5 and U266 Cells

Six- to eight-week old female SCID white mice were used to establish OCI-My 5 tumors. After washing in cold HBSS (Invitrogen), mice were inoculated subcutaneously with $1 \times 10^7$ cells in 200 µl of HBSS at the base of the tail. Mice were treated intravenously with PBS, 100 µg of anti-CD138, anti-dansyl (DNS)-IFNα, anti-CD138-IFNα, anti-CD20-mutIFNα, or anti-CD138-mutIFNα on days 14, 16, 18 post tumor challenge. Eight mice were included in each group. Bidirectional tumor growth measurements were obtained throughout the experiment, and mice were sacrificed when tumors reached 1.5 cm in diameter as per institutional guidelines. All studies were performed in compliance with the U.S. Department of Health and Human Services Guide for the Care and Use of Laboratory Animals and were approved by the UCLA Animal Research Committee.

For U266 tumors, NOD scid IL-2 receptor gamma chain knock out (NSG) mice were injected subcutaneously with $1 \times 10^7$ U226 cells and treated on days 14, 16 and 18 with 100 µg of the indicated proteins. One group was treated two additional times with anti-CD138-mutIFNα on days 25, 32 and 63. Eight mice were treated for each group except 6 mice for the group that received six treatments with anti-CD138-mutIFNα. Survival was monitored as well as the size of the tumors.

Results

Production and Characterization of Anti-CD138-IFNα Fusion Proteins

Figure 1B:
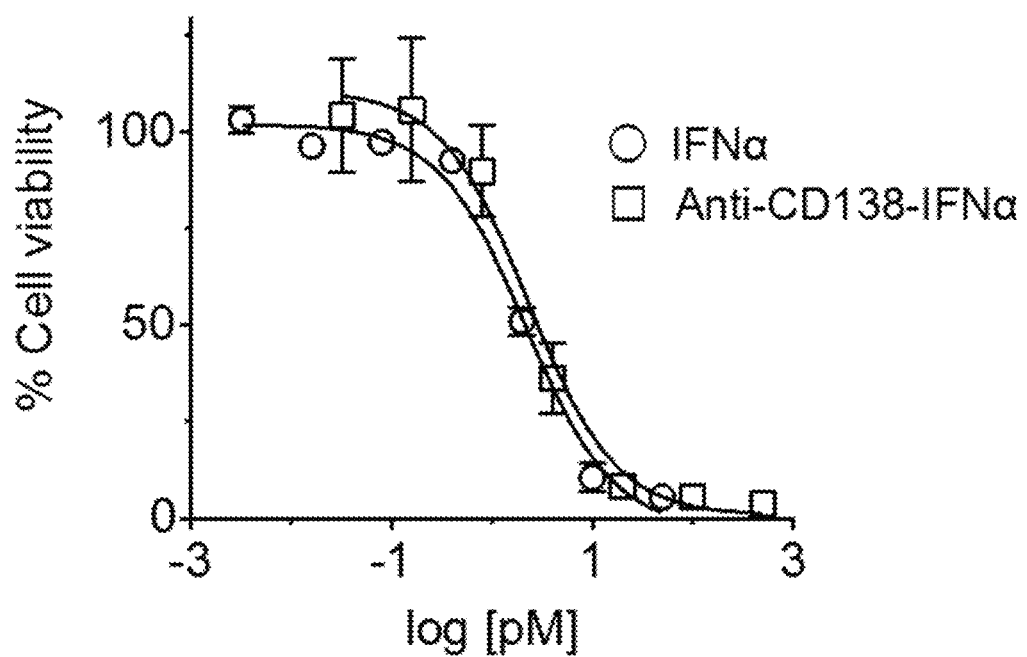

The $V_H$ and $V_L$ of the anti-CD138 antibody B-B4 were cloned into vectors for the expression of human anti-CD138 IgG1 either unfused or fused to IFNα (FIG. 1A). The vectors were expressed in stable transfectants of CHO cells, and the purified Igs were characterized with respect to their size, and assembly status, and ability to bind antigen (data not shown). To test for IFNα activity, the proteins were tested against the Daudi human lymphoma cell line, which is highly sensitive to the effects of IFNα. Cells were treated for 72 h and cell viability was measured using the MTS assay. The anti-CD138-IFNα was just as effective as recombinant IFNα in its cytotoxic effects on Daudi cells (FIG. 1B), confirming that IFN activity was not affected by IFNα's fusion to IgG.

Anti-CD138-IFNα Fusion Protein is Effective Against Some MM Cell Lines

MM cell lines have been shown to differ in their responses to various drugs and treatment. They also show biological and genetic heterogeneity and have been classified using various methods (Carrasco et al. (2006) *Cancer Cell* 9: 313-325; Drexler et al. (2000) *Leukemia,* 14: 777-782; Lombardi et al. (2006) *Genes Chromosomes Cancer,* 46: 226-238; Moreaux et al. (2011) *Haematologica,* 96: 574-582). Therefore, we assembled a panel of thirteen MM cell lines (XG-1, XG-2, OPM-1, OPM-2, S6B45, Delta 47, 8266/Dox40, 8266/S, H929, ANBL-6, MM144, U266, and OCI-My 5) to investigate their response to IFNα and the fusion protein. The panel includes both hyperdiploid and nonhyperdiploid cells with various chromosomal translocations (Table 3). Anti-CD138 IgG was found to bind all of the MM cell lines but did not bind to Daudi cells (data not shown), indicating that they express CD138 antigen.

TABLE 3

Panel of MM cell lines.

| Cell Line | | | | Ras | TP53 | RB | MYC | Mode of Action of anti-CD138-IFNα fusion |
|---|---|---|---|---|---|---|---|---|
| XG-1 | Hypodiploid Monosomy 13 | 11q13::14q32 | CCND1 | mut | abnormal | | 8q24::14q32 | |
| XG-2 | Hyperdiploid | 12q24.31::14q32 (unknown target) | Unknown target MAFB | mut | abnormal | | | |

TABLE 3-continued

Panel of MM cell lines.

| Cell Line | | | Ras | TP53 | RB | MYC | Mode of Action of anti-CD138-IFNα fusion |
|---|---|---|---|---|---|---|---|
| OPM-1 | Hyperdiploid 74 | insCλ@20q11 on 20t(11; 14:?) (q13; q32; ?) der(4), der(14) ins(Cq; 14) i(ins(Cq; 14)) | | | | CH insertion of t(1; 8)(q12?; 1 24):der(8) | |
| OPM-2 | Hyperdiploid 67 | 4; 14 der(4), der (14) ins(Cq; 14) | FGFR3 and MMSET | wt | abnormal | 8; 14 CH insertion on t(1; 8)(q12?; 1 wr):der(8) | |
| S6B45 | | | | Wt and mutated | | | |
| Delta 47 | Hyperdiploid 45 | 11?p | | | | insCλ@8q24 on der(19)t(8; 19) (q13; q13) | |
| 8226/D ox 40 | | | | | | | |
| 8226/S Aka RPMI8266*** | Hyperdiploid 60 | 14; 16 t(1; 14)(p13; q32) | c-maf | mut | abnormal | one allelic loss | c-myc insertion on t(16; 22)(q23; 111):der(16) | Apoptosis |
| H929 | Hyperdiploid 45 | 14p16::14q32 | Overexp FGFR3 and MMSET | mut | Wt | one allelic loss | 8q24::20q11 T(8; 20)q24; ?): der(8) | Apoptosis Block in cell cycle |
| ANBL-6 | Hyperdiploid 82 | 14q32::16q23 | Overexp c-maf | Wt | abnormal | ? | | Apoptosis |
| MM144 | | 14; 16 | Overexp c-maf | ? | ? | ? | | Apoptosis Block in cell cycle |
| U266* | Hyperdiploid 39 | Insertion at* | Overexp Cyclin D1 | Wt | abnormal | biallelic loss | LMYC (not c-myc) tp13::1p34 | Apoptosis |
| OCI-My 5 | Hyperdiploid 46 | 14q32::16q23 | Overexp c-maf | ? | ? | ? | 8q24::14q32 & dup(14)(q32q?22) | Block in cell cycle senescence† |

†Apoptosis and senescence was observed only with anti-CD138-mutIFNα treatment and not with IFNα alone or anti-CD138-IFNα treatment
*U266-Lombardi and Moreaux says t(11; 14) while Gabrea says 11q13 on der(11)t(11; ?)(q14; ?)
***This cell line may be the same as RPMI-8226. There is conflicting data as Lombardi says that RPMI-8226 has complex rearrangement involving "c-MYC insertion on t(16; 22)(q32; q11):der(16)" but Moreaux says 14; 16
$Zhang (1994)
The designation t(A; B)(p1; q2) is used to denote a translocation between chromosome A and chromosome B. The information in the second set of parentheses, when given, gives the precise location within the chromosome for chromosomes A and B respectively - with p indicating the short arm of the chromosome, q indicating the long arm, and the numbers after p or q refer to regions, bands and subbands seen when staining the chromosome with a staining dye. See also the definition of a "genetic locus".

Figure 2:
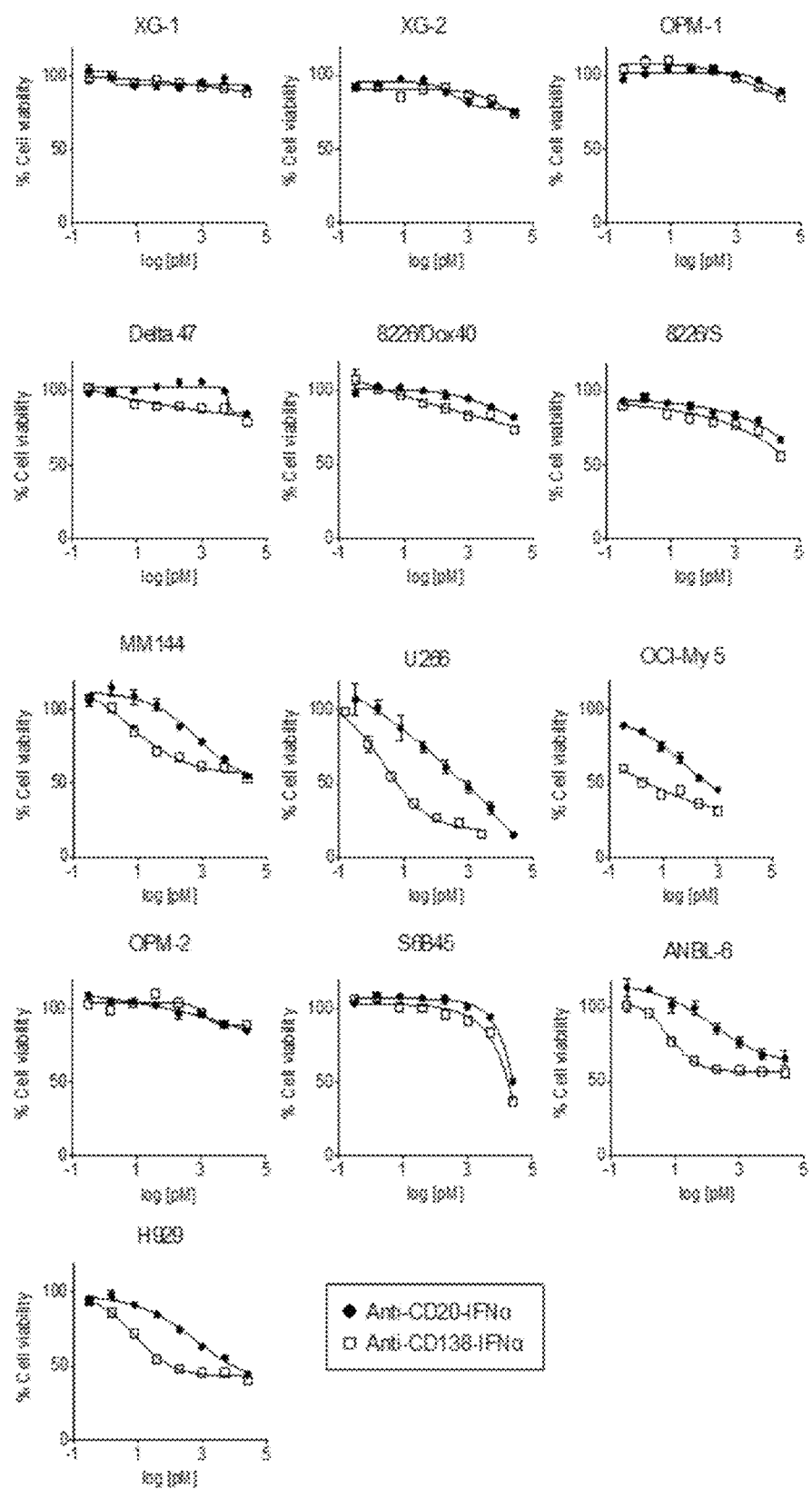
FIG. 2 shows the cytoreductive effects of anti-CD138-IFNα against HMCLs. The indicated cell lines were incubated with varying concentrations (0.3 pM-25 nM) of anti- CD20-IFNα or anti-CD138-IFNα for 3 days. Cell viability was measured using the MTS assay. The experiment was performed in triplicate for each concentration.

To determine if the HMCLs were sensitive to treatment with IFNα fusion protein, HMCLs were incubated with varying concentrations of anti-CD138-IFNα, and cell viability was assessed. Anti-CD138-IFNα was used to target IFNα to the MM cell lines while anti-CD20-IFNα was used as an untargeted control. After 3 days of treatment, cell viability was measured by MTS activity. The MM cell lines differed in their response to treatment with the fusion proteins. The targeted anti-CD138-IFNα was found to be more effective than untargeted anti-CD20-IFNα for H929, ANBL-6, U266, MM144 and OCI-My 5 cell lines. The fusion protein had little or no effect on the XG-1, XG-2, OPM-1, OPM-2, Delta 47 cell lines while an intermediate effect was observed for S6B45, 8226/Dox40, and 8226S (FIG. 2). However, when treatment with anti-CD138-IFNα was increased to 4 days, a decrease in viability was observed in OPM-1, OPM-2 and Delta 47 cells (data not shown). Similar results have been published for OPM-1, OPM-2, XG-1, Delta 47, ANBL-6, MM144, and H929 when these cell lines were treated with IFNα, but in contrast to our data, XG-2 was found to be responsive to IFNα (Crowder et al. (2005) Blood, 105: 1280-1287). Our data demonstrate that addition of anti-CD138 IgG to IFNα results in a fusion protein effective against a number of HMCLs representing MM with different molecular abnormalities.

The Effects of IFNα, Anti-CD138-IFNα and Anti-CD138-mutIFNα Fusion Proteins on HMCLs IFNα and IFNβ share a common receptor comprised of two transmembrane proteins, IFNAR1 and IFNAR2, and have many overlapping activities. However, differential activities of the various type I IFNs have also been reported. IFNβ has been reported to have a ~20- to 50-fold greater affinity for IFNAR1 than IFNα2 and this greater affinity has been shown to correlate with a significantly higher anti-proliferative activity (Jaitin et al. (2006) *Mol Cell Biol* 26: 1888-1897; Kalie et al. (2007) *J. Biol. Chem.,* 282: 11602-11611). In an initial attempt to determine if IFNβ fusion proteins would be an effective anti-cancer therapeutic, we fused mouse or human IFNβ to the C-terminal end of an anti-tumor IgG. Although the mouse IFNβ fusion protein retained its activity, the human IFNβ fusion protein had a >100-fold decrease in activity (unpublished results). As an alternative approach, we chose to make an anti-CD138 fusion protein using a mutant IFNα2 designed to mimic IFNβ with greater affinity for IFNAR1 and enhanced anti-proliferative activity (Kalie et al. (2007) *J. Biol. Chem.,* 282: 11602-11611). This mutant IFNα2 (mutIFNα) contains mutations at three positions (H57Y, E58N, Q61S), which confer upon it a 60-fold increased affinity for IFNAR1 than wild-type IFNα2 and a 3-fold higher affinity than IFNβ. In addition, mutIFNα was shown to exhibit an increase in anti-proliferative activity (80- and 150-fold increase, depending on the cell line used) when compared to wild-type IFNα, and a slight increase in activity when compared to IFNβ. Surprisingly, targeted anti-CD20-mutIFNα was found to be less effective in inhibiting the proliferation of CD20 expressing Daudi cells than targeted wild type IFNα (anti-Cd20-IFNα). The anti-viral activity of wild-type IFNα, mutIFNα and IFNβ were found to be very similar (Id.).

Figure 3A:
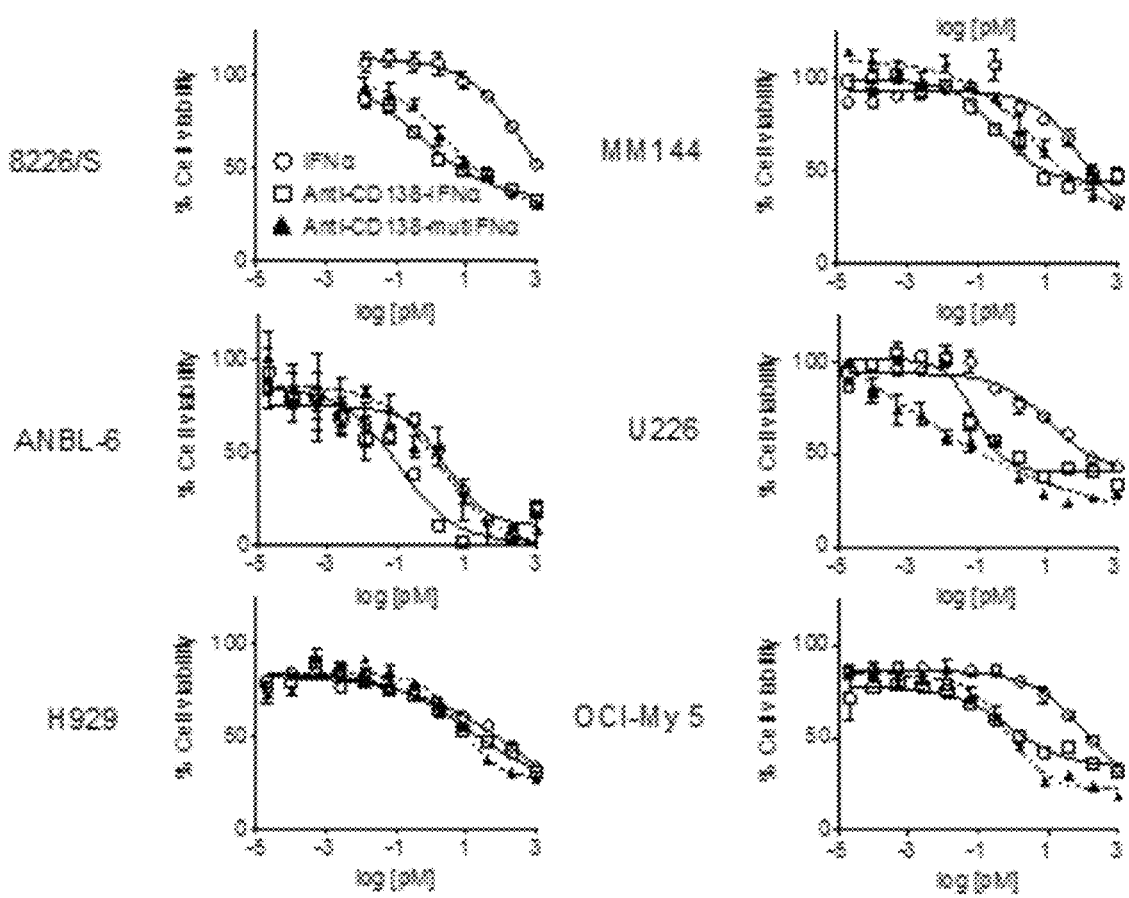
FIGS. 3A-3C show the effects of IFNα, anti-CD138-IFNα and anti-CD138-mutIFNα on six sensitive HMCLs.

The anti-tumor activities of IFNα, anti-CD138-IFNα and anti-CD138-mutIFNα against six sensitive cell lines were examined. More specifically, we examined their ability to inhibit cell proliferation, influence cell cycle progression, and cause apoptosis. The cytoreductive activity of anti-CD138-IFNα and anti-CD138-mutIFNα was compared to untargeted IFNα by MTS assay. The targeted fusion proteins were more effective at decreasing cell viability than IFNα alone for all HMCLs except H929, in which IFNα and the fusion proteins had very similar activity. When compared to one another, anti-CD138-IFNα and anti-CD138-mutIFNα showed similar effects in 8226/S, MM144 and H929. Anti-CD138-IFNα was more effective than anti-CD138-mutIFNα for the ANBL-6 cell line. In contrast, anti-CD138-mutIFNα was more effective than anti-CD138-IFNα in U266 and OCI-My5 cells (FIG. 3A).

Figure 3B:
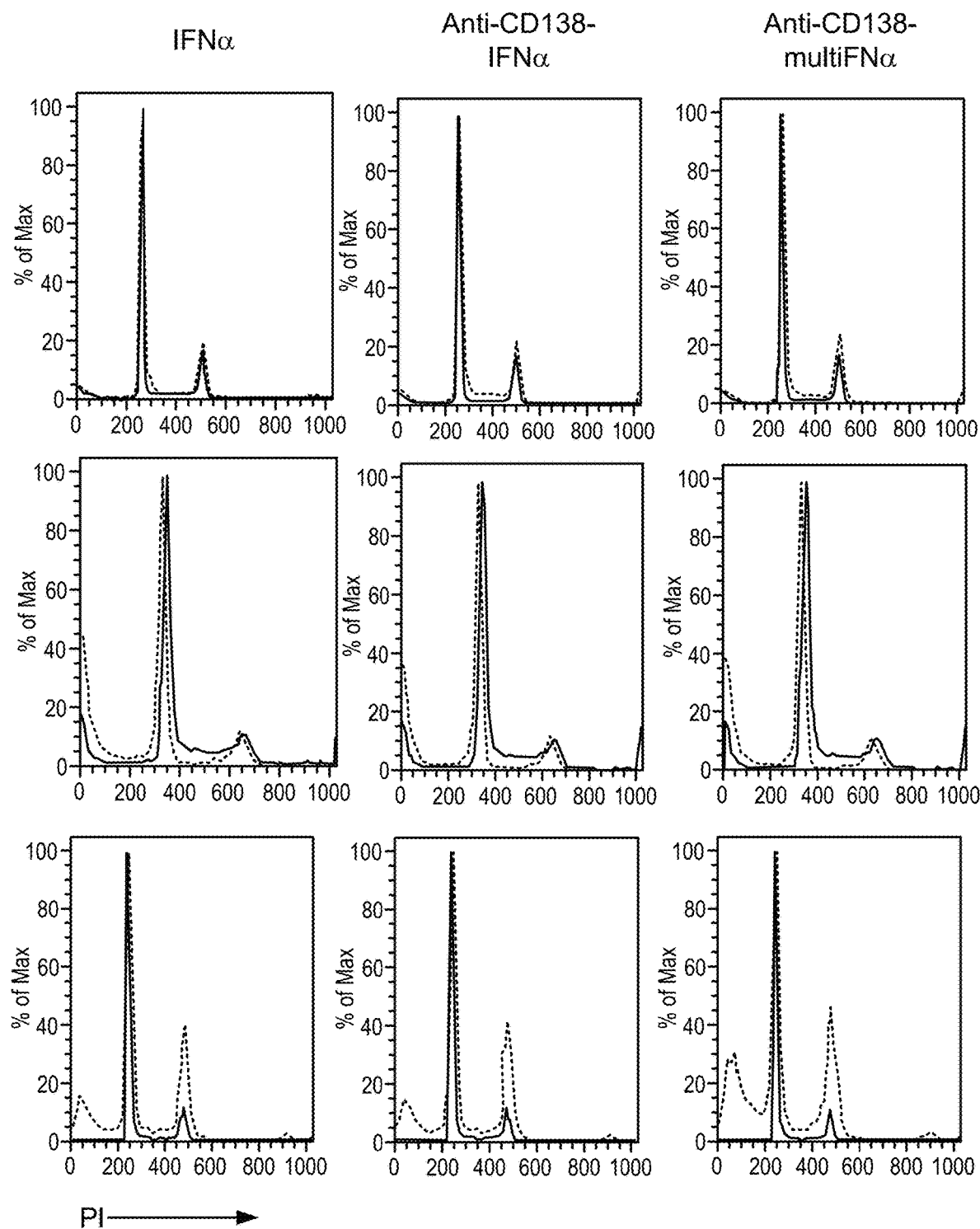

The cytoreductive effects of the IFNα fusion proteins were further investigated by determining if HMCLs were blocked in cell cycle progression or were undergoing apoptosis. To determine if there were changes to the cell cycle, HMCLs were analyzed for DNA content by flow cytometry following permeabilization and staining with PI after 4 days of treatment (FIG. 3B). 8226/S, ANBL-6 and U266 cells did not exhibit any changes in cell cycle or DNA content in response to IFNα or fusion proteins. A slight increase in OCI-My5 cells in the sub-$G_0$ and $G_2$/M phase was observed when treated with anti-CD138-mutIFNα.

Figure 3C:
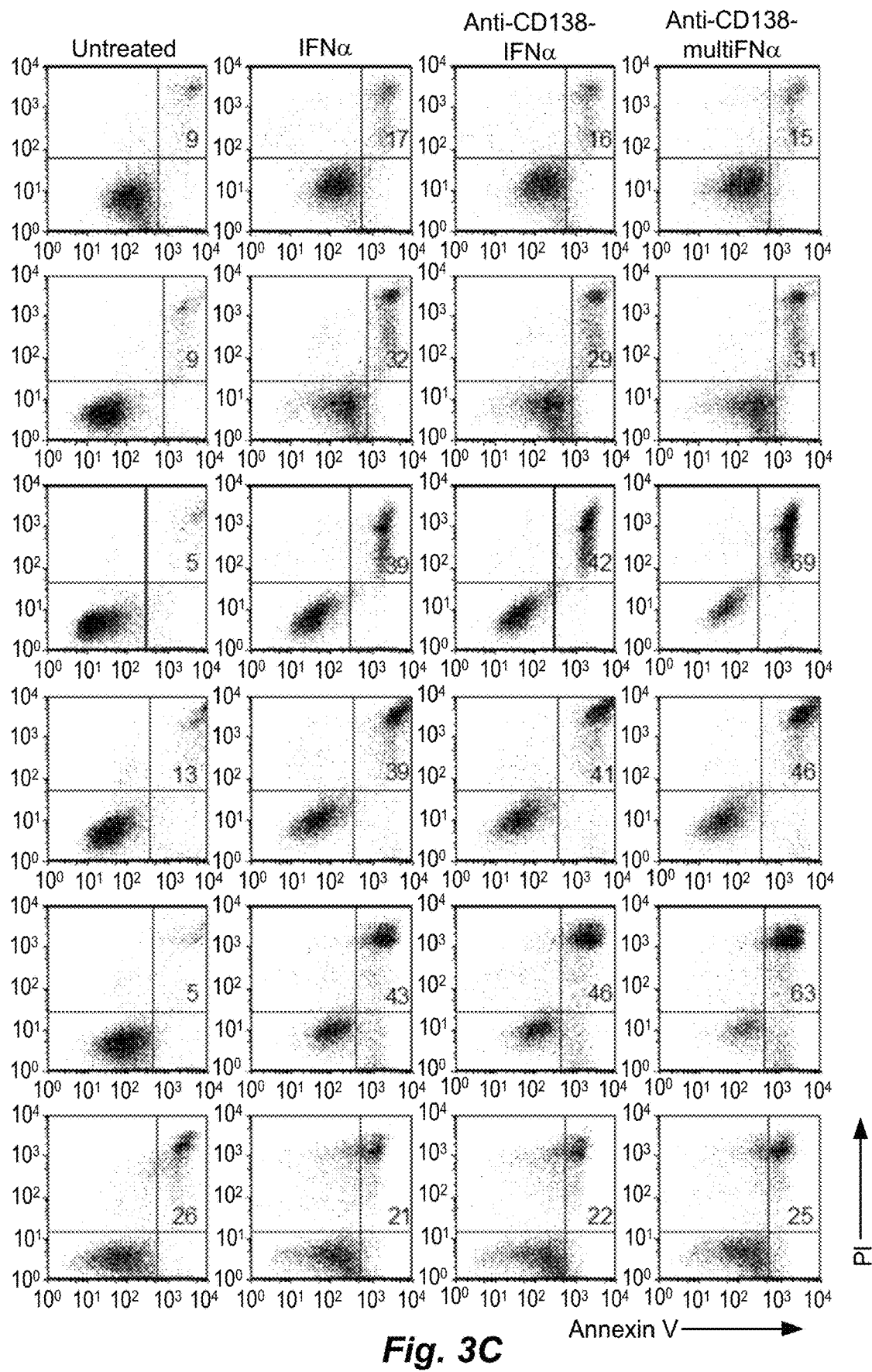

In contrast MM144 and H929 showed a marked accumulation of cells in $G_2$/M, with H929 also having an accumulation of cells with sub-$G_0$ content of DNA (apoptotic cells). To test if HMCLs were undergoing apoptosis as a result of treatment, cells were stained with Alexa Fluor 488 labeled Annexin V and PI and analyzed by flow cytometry (FIG. 3C). An induction of apoptosis was observed after treatment for all of the cell lines except OCI-My 5; IFNα or the fusion proteins did not induce apoptosis in this cell line at even higher concentration of 1 nM (data not shown). In addition, a relatively high level of basal apoptosis was observed for OCI-My 5 in multiple experiments. In contrast, apoptosis was induced in all of the other HMCLs. 8226/S and ANBL-6 showed a similar level of apoptosis in response to all three treatments. On the other hand, U266 and H929 had similar levels of apoptosis in response to IFNα and anti-CD138-IFNα but showed a significantly greater level of apoptosis in response to anti-CD138-mutIFNα; MM144 also showed some improvement with anti-CD138-mutIFNα. These data are summarized in Table 4. Interestingly, the cytoreductive effects of IFNα appear to involve various mechanisms such as cell cycle arrest, apoptosis and senescence, and for some cell lines, more than one pathway appears to be at work.

TABLE 4

The differential effects of IFNα and fusion proteins against MM cell lines.

| Construct | 8226/S | ANBL-6 | H-929 | MM144 | U266 | OCI-My 5 |
|---|---|---|---|---|---|---|
| Cell cycle arrest | | | | | | |
| IFNα | − | − | + | ++ | − | − |
| Anti-CD138-IFNα | − | − | + | ++ | − | − |
| Anti-CD138-mutIFNα | − | − | ++ | + | − | + |
| Apoptosis | | | | | | |
| IFNα | +/− | + | + | + | + | − |
| Anti-CD138-IFNα | +/− | + | + | + | + | − |
| Anti-CD138-mutIFNα | +/− | + | ++ | + | ++ | − |
| Senescence | | | | | | |
| IFNα | + | − | + | +/− | − | − |
| Anti-CD138-IFNα | + | − | + | +/− | − | − |
| Anti-CD138-mutIFNα | + | − | + | +/− | − | + |

Figure 4A:
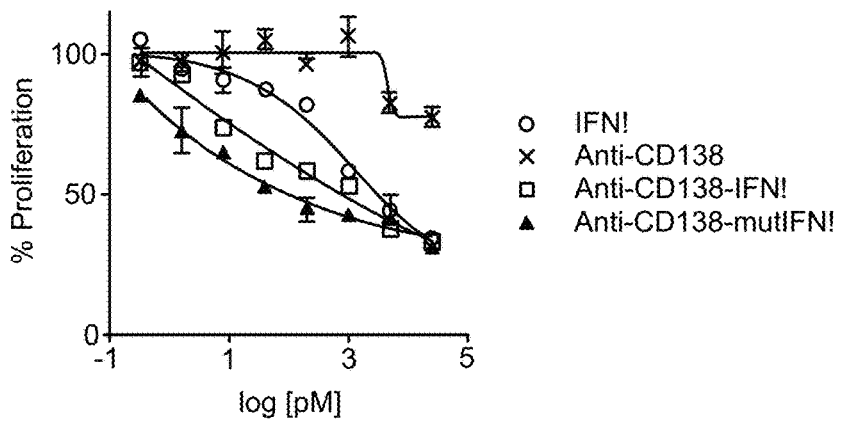
FIGS. 4A and 4B show the effect of IFNα, anti-CD138 IgG, anti-CD138-IFNα and anti-CD138-mutIFNα on proliferation and induction of senescence in OCI-My 5 cells.

Although there was some change to the cell cycle when OCI-My 5 cells were treated with anti-CD138-mutIFNα, apoptosis was not observed. In addition, treatment with IFNα and anti-CD138-IFNα did not cause apoptosis or blocks to cell cycle progression in OCI-My 5 cells. To confirm that IFNα and the fusion proteins have a cytoreductive effect, we tested the proliferative status of the cells after treatment. $^3$[H]-thymidine incorporation was measured after 3 days of treatment with varying concentrations of IFNα, anti-CD138, anti-CD138-IFNα, or anti-CD138-mutIFNα (FIG. 4A). A decrease in proliferation was observed in OCI-My 5 cells, with the fusion proteins having a greater effect than IFNα alone. Furthermore, the higher affinity anti-CD138-mutIFNα caused a greater effect than the wild type anti-CD138-IFNα. Anti-CD138 IgG did not decrease the ability of the cells to proliferate although some decrease was seen at the highest concentrations.

Figure 4B:
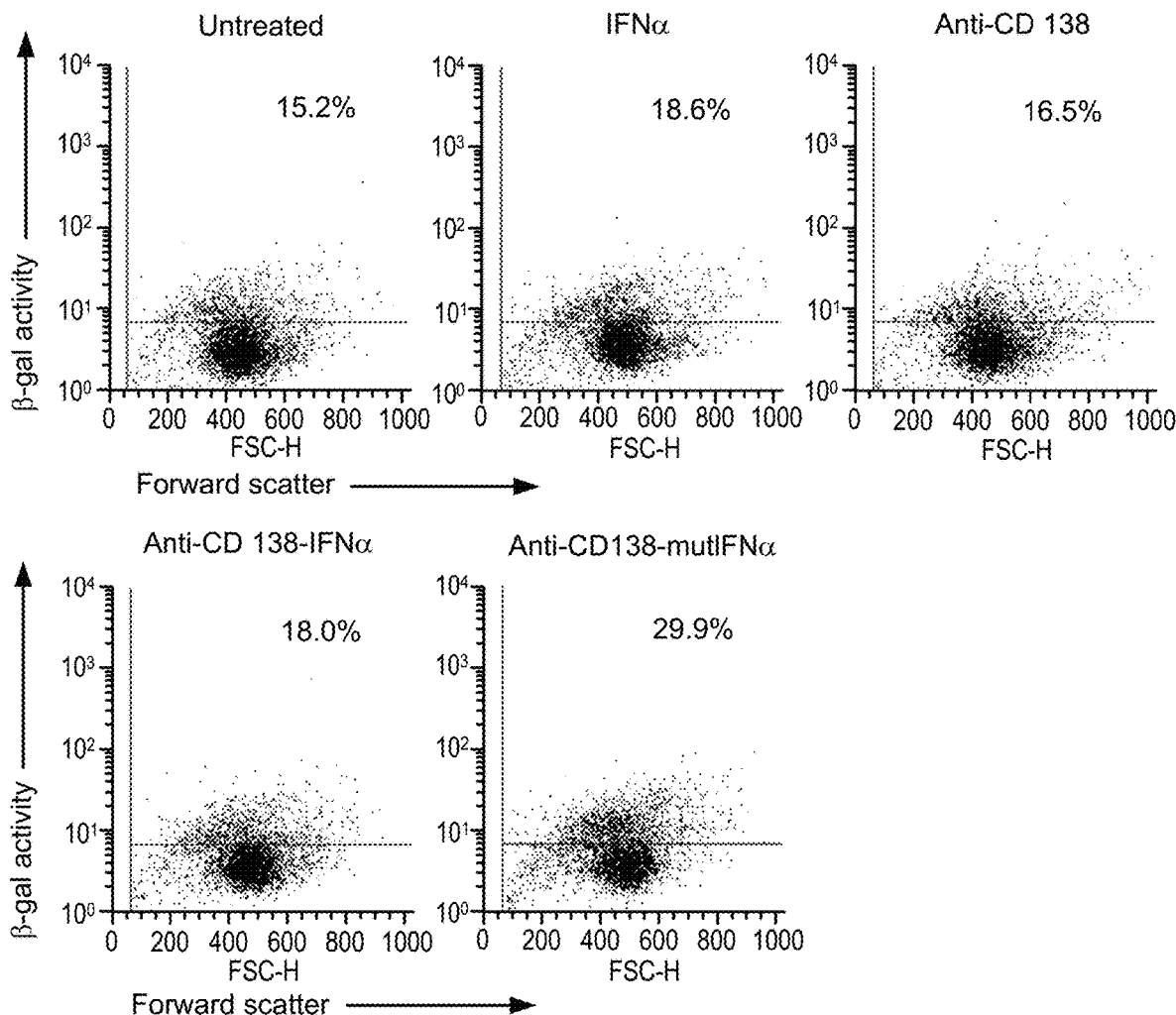

Another possibility for the decrease in cell viability and proliferation is oncogene-induced senescence (OIS). OIS is thought to be part of a safeguard mechanism to prevent abnormal cells from further expansion. Cells in senescence have been shown to be metabolically active in vitro but do not divide. We examined if IFNα and/or the fusion proteins could induce senescence in OCI-My 5 cells. One common marker for the detection of senescence is β-gal activity at pH 6, which is a barometer for increased lysosomal content of senescent cells. OCI-My 5 cells were treated for 3, 4, 6 or 7 days with 1 nM of IFNα, anti-CD138, anti-CD138-IFNα, or anti-CD138-mutIFNα and β-gal activity detected by flow cytometry. At all time points, there was little or no increase in β-gal activity following treatment with IFNα, anti-CD138 IgG, or anti-CD138-IFNα. However, there was a large increase in β-gal activity in cells treated with anti-CD138-mutIFNα. A representative experiment at 3 days is shown in FIG. 4B. Thus induction of senescence appears to account at least in part for the reduced proliferation observed following treatment with anti-CD138-mutIFNα. These data suggest that the induction of senescence in this HMCL requires the higher affinity mutIFNα and senescence does not seem to explain the inhibition of proliferation seen with IFNα, or anti-CD138-IFNα.

Taken together, these data indicate that although IFNα and the fusion proteins have cytoreductive activity against many HMCLs, the cell lines have differential responses against this cytokine. These differences underscore the fact that HMCLs and MM cells in vivo are heterogeneous in nature.

Fusion Proteins are Effective Against Primary MM Cells from Patients

To determine if the fusion proteins are effective against primary tumors, cells were isolated from multiple myeloma patients. Cells were treated with 25 nM of unfused anti-CD138, fused anti-CD138-IFNα or anti-CD138-mut IFNα for 3 days and the percentage of viable cells compared to DMSO-treated control (arbitrarily designated as 100%) was determined. The assays used were trypan blue exclusion or MTT assay.

Figure 5:
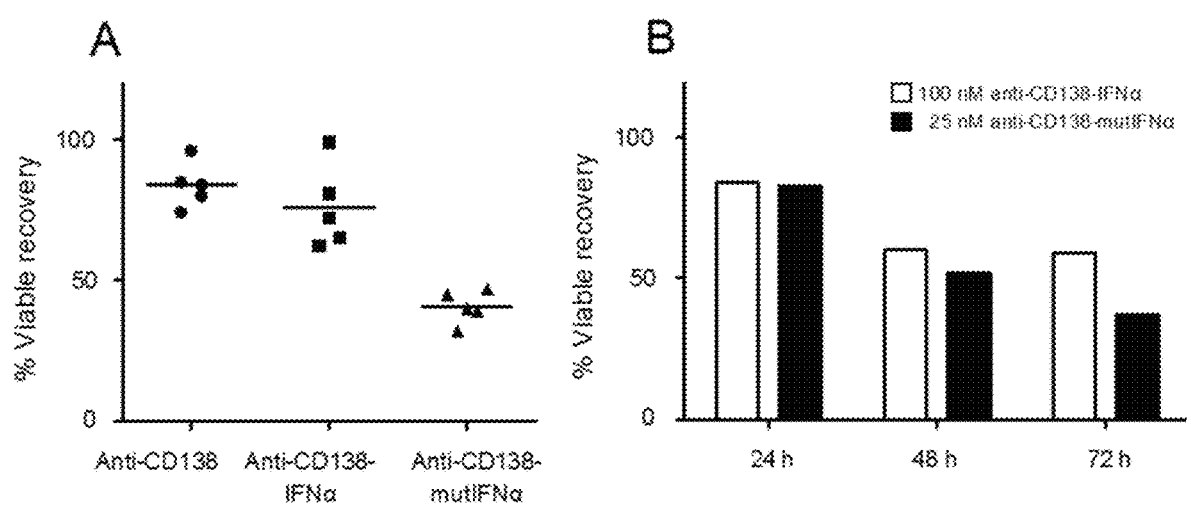
FIG. 5, panels A and B show activity of anti-CD138, anti-CD138-IFNα anti-CD138-mutIFNα against primary myeloma cells. (A) Purified MM cells from 5 different patients were incubated with 25 nM of the indicated proteins for 72 h and cell viability determined by trypan blue exclusion and an MTT assay. (B) Patient samples were treated with the indicated proteins for 24, 48 or 72 h and the percentage of viable cells recovered determined by trypan blue exclusion and an MTT assay. Data represent the average of 6 patients. Both experiments were performed once.

There was some variability in the response of the cells from five patients. Generally, the unfused IgG had little effect, while treatment with IFNα fusion proteins, especially the mutant, caused significant decreases in cell viability (FIG. 5, panel A). To determine the time course for the effects of the fusion proteins, cells from six patients were treated for 24, 48 and 72 h and the percentage of viable cells was determined. Although not much difference was apparent after 24 h of treatment, 25 nM of anti-CD138-mutIFNα was more potent in cytoreductive effects than 100 nM of anti-CD138-mutIFNα (FIG. 5, panel B).

Fusion Proteins are Effective in a Murine Xenograft Model of MM

To determine if the fusion proteins would be able to provide protection against MM in vivo, we used a murine xenograft models of MM using OCI-My 5 cells or U266 cells. SCID mice were injected subcutaneously with $1 \times 10^7$ OCI-My 5 cells and treated on days 14, 16 and 18 with 100 µg of anti-CD138-IFNα or anti-CD138-mutIFNα. Treatment with PBS, anti-CD138, and untargeted anti-DNS-IFNα and anti-CD20-mutIFNα served as controls. Survival was monitored as well as the size of the tumors. Unfused anti-CD138 and untargeted anti-DNS-IFN increased survival slightly as compared to PBS control. Treatment with the targeted anti-CD138-IFNα resulted in a significant increase in survival (p≤0.001 compared to PBS), but an even greater effect was observed with anti-CD138-mutIFNα (p=0.0004 compared to anti-CD138-IFNα).

To determine the in vivo efficacy of fusion protein treatment against the U266 tumor, NSG mice were injected subcutaneously with $1 \times 10^7$ U226 cells and treated on days 14, 16 and 18 as indicated by the black arrows with 100 µg of the indicated proteins. One group was treated two additional times with anti-CD138-mutIFNα on days 25, 32 and 63 as indicated by the grey arrows. Eight mice were treated for each group except 6 mice for the group that received six treatments with anti-CD138-mutIFNα. Survival was monitored as well as the size of the tumors. Targeted anti-CD138-IFNα was much more effective than untargeted anti-DNS-IFNα in protecting against tumor growth. Moreover, targeted anti-CD138-mutIFNα was even more effective than anti-CD138-IFNα. When mice were treated with two additional doses of 100 µg of anti-CD138-mutIFNα on days 25 and 32, tumor growth was delayed with palpable tumors not observed until day 60. At day 63 mice were treated with an additional 100 µg of anti-CD138-mutIFNα which served to delay but not completely prevent tumor growth. However, it can be speculated that treatment with additional quantities of fusion protein may have succeeded in completely inhibiting tumor growth.

Discussion

IFNα therapy has been used for treatment of MM, but disagreement exists as to its efficacy. However, meta-analysis of 17 trials among 2333 patients who received IFN-chemotherapy induction treatment or chemotherapy alone showed significantly superior outcomes in IFN treated patients for relapse-free and overall survival; similarly, meta-analyses of maintenance treatments also showed outcomes significantly better in the IFN treatment arms than in untreated controls (Fritz and Ludwig (2000) *Ann. Oncol.*, 11: 1427-1436), underscoring the fact that IFNα can be an effective therapeutic against MM. However the systemic toxicity associated with IFNα treatment as well as its short in vivo half-life have limited the clinical efficacy of IFN treatment. Our approach to circumventing these problems is to fuse IFNα to anti-CD138 IgG in order to increase its half-life and by targeting, deliver an effective dose of IFNα to the tumor site without systemic toxicity.

MM is characterized by significant heterogeneity. Our studies as well as others (Gomez-Benito et al. (2005) *FEBS Lett.*, 579: 6217-6122; Gomez-Benito et al. (2007) *Cell Signal* 19: 844-854) showed that not all MMs are responsive to treatment with IFNα. However, for those HMCLs that are sensitive, targeting via the anti-CD138 antibody portion improved the efficacy of IFNα against MM, and in some cases, anti-CD138-mutIFNα, which has a higher affinity for IFNAR, was more effective than anti-CD138-IFNα. However, the responsiveness of MM cell lines to IFNα does not appear to always correlate with the level of expression of IFNAR (Gomez-Benito et al. (2005) *FEBS Lett.*, 579: 6217-6122). Our analysis of HMCLs revealed that different cell lines exhibit different responses. Consistent with previous studies (Arora and Jelinek (1998) *J. Biol. Chem.*, 273: 11799-11805; Minami et al. (2000) *Exp. Hemat.*, 28: 244-255; Chen et al. (2001) *Blood*, 98: 2183-2192; Crowder et al. (2005) *Blood*, 105: 1280-1287; Gomez-Benito et al. (2005) *FEBS Lett.*, 579: 6217-6122; Arulampalam et al. (2011) *Exp. Cell Res.*, 317: 9-19), the mechanism of action of IFNα against MM was found to include apoptosis, blockage in cell cycle progression and senescence.

Following treatment H929 and MM144 cell lines both showed dramatic changes to cell cycle progression and were blocked at G2/M, with H929 also having a significant number of cells in the sub-G0 phase. Both also underwent apoptosis. Our results were consistent with previous studies that showed that MM144 is blocked in G2 when treated with IFNα. H929 contains a 4p16::14q32 translocation (overexpresses FGFR3 and MMSET) while MM144 contains a 14q32::16q23 translocation (overexpresses c-maf). Thus, although the two cell lines have a similar response to treatment, they contain different genetic abnormalities. The stop in cell cycle progression is different from what has been reported for Daudi cells treated with IFNα, which show a stop at G1 (Subramanian et al. (1997) *J. Biol. Chem.*, 272: 14713-14720).

In contrast, 8226/S, ANBL-6 and U266 did not display changes in the cell cycle, but did undergo apoptosis in response to IFNα alone and to IFNα fusion treatment; ANBL-6 is IL-6 dependent. Both 8226/S and ANBL-6 are hyperdiploid with a 14q32::16q23 translocation. On the other hand, U266 is hypodiploid with a 11q13 insertion and overexpresses cyclin D1. U266 has previously been shown to have biallelic deletion of RB gene and does not express pRB (Dao et al. (1994) *Leukemia, UK* 8: 1280; Corradini et al. (1994) *Leukemia*, 8: 758).

Unlike the other HMCLs analyzed, the OCI-My 5 cell line did not undergo apoptosis, become blocked in cell cycle progression or undergo senescence when treated with IFNα or anti-CD138-IFNα. However, changes to the cell cycle and induction of senescence were observed when cells were treated with anti-CD138-mutIFNα, suggesting that the higher affinity of mutIFNα for IFNAR is necessary to affect this cell line. The reason for the cytoreductive effects of anti-CD138-IFNα against OCI-My 5 cells as detected by MTS assays (FIG. 3) is not clear.

The two main pathways of oncogene-induced senescence are p16INK4a-RB and ARF-p53, which are involved in the execution of proliferative arrest. IFNα has been shown to induce senescence in endothelial cells (Pammer et al. (2006) *Lab. Invest.*, 86: 997-1007); however, no studies have yet reported IFNα-induced senescence in MM.

There did not appear to be a correlation between the type of genetic abnormality and their responsiveness to IFNα fusion treatment. For example, the four cell lines with the 14q32::16q23 translocation and overexpression of c-maf (OCI-My 5, 8226/S, H929 and ANBL-6) showed apoptosis, cell cycle, or senescence in response to IFNα fusion protein treatment.

These findings suggest that the variable responses of the different HMCLs may be attributed to the heterogeneity, some of which is outlined in Table 4, in the molecular pathogenesis of MM.

In addition to in vitro data using HMCLs, we show that the targeted IFNα fusion proteins are effective against primary cells from MM patients and in a murine xenograft model. These data suggest that targeting of IFNα via the anti-CD138 moiety may be an effective strategy in the treatment of MM. In primary cells (and in the mouse model?), the higher affinity anti-CD138-mutIFNα fusion protein was more effective than being more effective than wildtype anti-CD138-IFNα. Although the treatments were effective in prolonging survival in mice, the fusion proteins may prove to be even more effective in the treatment of human MM patients because of immunomodulatory activities of IFNα as well as the IgG Fc region. It is conceivable that in addition to the direct effects of IFNα, the fusion proteins may also activate ADCC and CDC, further contributing to cancer cell killing in patients.

Signaling pRb protein is involved in regulating progression through G1 into S phase; however, the HMCLs with blocks in cell cycle progression were arrested at G2/M and some at sub-G0.

Example 2

Anti-CD138-Interferon α2 Fusion Proteins are Effective In Vitro and In Vivo Against Multiple Myeloma Translational Relevance It is estimated that in the United States 22,350 individuals will be diagnosed with and 10,700 will die of myeloma in 2013. Although much progress has been made in the treatment of myeloma, most treated individuals relapse, and myeloma remains an incurable disease. Therefore, innovative therapeutic approaches are desperately needed. IFN treatment has shown some efficacy for the treatment of myeloma, but the associated toxicities have limited its efficacy. We propose a novel approach in which IFN is targeted to myeloma cells expressing CD138 using anti-CD138-IFN fusion proteins. We believe that the targeted IFN is effective in killing myeloma cells and in eliciting a tumor specific immune response.

Purpose:

Multiple myeloma, a plasma cell malignancy characterized by a high degree of heterogeneity, is the second most prevalent hematologic malignancy in the US. Although much effort has been made trying to understand the etiology and the complexities of this disease with the hope of developing effective therapies, multiple myeloma remains incurable at this time. Because of their anti-proliferative and pro-apoptotic activities, IFNs have been used to treat various malignancies including multiple myeloma. Although some success has been observed, the inherent toxicities of IFNs limit their efficacy.

Experimental Design:

To address this problem, we produced anti-CD138 antibody fusion proteins containing either IFNα2 or a mutant IFNα2 (IFNα2$^{YNS}$) with the goal of targeting IFN to CD138 expressing cells, thereby achieving effective IFN concentrations at the site of the tumor in the absence of toxicity.

Results:

The fusion proteins inhibited the proliferation of a variety of cell lines that represent different molecular and biological multiple myeloma subtypes. Depending on the cell line, the interference with growth following treatment with the fusion proteins included the induction of apoptosis, blocks in cell cycle progression and/or senescence. In addition, the fusion proteins were effective against primary cells from multiple myeloma patients, and treatment with fusion proteins prolonged survival in two different xenograft models. These studies suggest that IFNα antibody fusion proteins may be effective novel therapeutics for the treatment of multiple myeloma.

Introduction

Multiple myeloma is a disease characterized by an excess of malignant plasma cells in the bone marrow. Accumulation and proliferation of malignant myeloma cells result in disruption of normal hematopoiesis and changes to bone marrow vascularization and bone physiology. Analyses of patient myeloma cells and human myeloma cell lines (HMCLs) have revealed the extensive molecular heterogeneity of this disease (Carrasco et al. (2006) *Cancer Cell* 9: 313-325; Drexler et al. (2000) *Leukemia*, 14: 777-782; Lombardi et al. (2006) *Genes Chromosomes Cancer*, 46:

226-238; Moreaux et al. (2011) *Haematologica,* 96: 574-582). The survival rate for multiple myeloma is 7-8 years when patients are treated with drugs such as proteasome inhibitor bortezomib, or thalidomide and lenalidomide, which target myeloma cells in the bone marrow microenvironment (Kumar et al. (2008) *Blood,* 111: 2516-2520). Currently there is no cure for multiple myeloma.

Besides their anti-viral and immunostimulatory activities, IFNs have anti-proliferative activity and can induce apoptosis in hematological malignancies and solid tumors (Borden et al. (2000) *Semin. Cancer Biol.,* 10: 125-144; Borden et al. (2007) *Nat. Rev. Drug Discov.,* 6: 975-990). Many studies have shown that type I IFNs, which were the first recombinant proteins used in the treatment of cancer, may be highly effective against a variety of tumor cell targets (reviewed in Borden et al. (2007) *Nat. Rev. Drug Discov.,* 6: 975-990). Both IFNα and IFNβ bind to the same receptor composed of two transmembrane proteins, IFNAR1 and IFNAR2. However, IFNβ has a 20- to 50-fold greater affinity for IFNAR1 than IFNα2, and this greater affinity has been shown to correlate with a significantly higher anti-proliferative activity against some malignancies (Jaitin et al. (2006) *Mol. Cell Biol.,* 26: 1888-1897; Kalie et al. (2007) *J. Biol. Chem.,* 282: 11602-11611). However, the effectiveness of type I IFNs for cancer therapy has been overshadowed by their associated side effects when used at high doses (Weiss (1998) *Semin. Oncol.,* 25: 9-13) and a short half-life of only 1 hour (Peleg-Shulman et al. (2004) *J. Med. Chem.,* 47: 4897-4904). Previously, we produced an anti-CD20-IFNα2 fusion protein and showed that targeting to CD20 expressed on tumor cells resulted in potent anti-proliferative and pro-apoptotic effects on human B cell lymphoma cell lines in vitro and in a murine lymphoma model (Xuan et al. (2010) *Blood,* 115: 2864-2871). We have also shown that fusion of IFNα or IFNβ to IgG increased the half-life to 8 hours (Huang et al. (2007) *J. Immunol.,* 179: 6881-6888; Trinh et al. (2013) *J. Immunother.,* 36: 305-318).

To determine if this approach would also be effective against multiple myeloma, we constructed fusions of anti-CD138 with IFNα2 and IFNα2$^{YNS}$, a high affinity IFNα2 mutant (Jaitin et al. (2006) *Mol. Cell Biol.,* 26: 1888-1897; Kalie et al. (2007) *J. Biol. Chem.,* 282: 11602-11611). CD138, also known as syndecan-1, is a heparan sulfate proteoglycan that is highly expressed on HMCLs and malignant plasma cells in peripheral blood and in the bone marrow in patients (Chilosi et al. (1999) Mod. Pathol., 12: 1101; Ridley et al. (1993) *Blood* 81: 767-774; Wijdenes et al. (1996) *Br. J. Haematol.,* 94: 318-323). Treatment with IFNα fusion proteins resulted in the induction of apoptosis, blockage in cell cycle and/or senescence in different HMCLs. In addition, the fusion proteins were effective against primary patient cells and in vivo against multiple myeloma tumors in murine models.

Materials and Methods

Cells

HMCLs were obtained through the generous gift of Dr. W. Michael Kuehl and Dr. Diane Jelinek. Their authenticity was confirmed by anti-CD138 staining. Primary cells were obtained after informed consent and approved by the institutional medical ethical committee. HMCLs were cultured in RPMI 1640 (Invitrogen) supplemented with 5% fetal calf serum (FCS; Atlanta Biologics). ANBL-6 cells were cultured as described with the addition of 2 ng/mL of IL-6. Chinese Hamster Ovary (CHO) cells were cultured in Iscove's Modified Dulbecco's Medium (IMDM; Invitrogen) supplemented with 5% FCS.

Construction of Expression Vectors, Protein Production and Purification

The anti-CD138 heavy and light chain variable (V) region amino acid sequences were obtained from US Patent Application No: 2009/0175863. The sequences were used to construct expression vectors as described in Supplemental methods. To construct the DNA vector for the expression of anti-CD138-IFNα2$^{YNS}$, nested PCR was used to introduce three amino acid mutations (H57Y, E58N, and Q61S) as described in Supplemental methods.

Expression vectors were stably transfected into CHO cells to produce fusion proteins and purified using protein A affinity chromatography as described in Supplemental methods.

MTS and Apoptosis Assays

HMCLs were treated with IFNα2, IFNβ, anti-CD138, anti-CD20-IFNα2, anti-CD20-IFNα2$^{YNS}$, anti-CD138-IFNα2 or anti-CD138-IFNα2$^{YNS}$. Metabolic activity was determined using MTS assay as described in Supplemental methods. Apoptosis was measured by staining cells with Alexa Fluor 488-labeled Annexin V and propidium iodide (PI) as described in Supplemental methods.

Cell Cycle Analysis

Cells were treated with 500 pM of IFNα2, IFNβ, anti-CD138-IFNα2, or anti-CD138-IFNα2$^{YNS}$ for 4 days at 37° C. Cells were incubated with 1 ml of hypotonic DNA staining buffer (1 mg/ml sodium citrate, 100 µg/ml PI, 20 µg/ml RNase A, and 0.3% Triton X-100) for 30-60 minutes at 4° C. in the dark. Cells were analyzed by flow cytometry and cell cycle analysis performed using FlowJo software with the Watson Model.

Detection of ppRb and IRF-4

Cells were treated for 48 hours with 1 nM IFNα2, IFNβ, anti-CD138-IFNα2, or anti-CD138-IFNα2$^{YNS}$ and analyzed by Western blotting using anti-IRF-4 or anti-ppRb Ser807/811 as described in Supplemental methods.

Assays for Replicative Senescence

Cells were treated with IFNα2, anti-CD138, anti-CD138-IFNα2, or anti-CD138-IFNα2$^{YNS}$ for 3 days. Senescence induced β-galactosidase (β-gal) activity was detected as described previously (Debacq-Chainiaux et al. (2009) *Nat. Protoc.,* 4: 1798-1806) and in Supplemental methods. To detect Ki-67 protein, cells were stained and analyzed by flow cytometry as described in Supplemental methods.

In Vivo Anti-Tumor Activity Against OCI-My5 and U266 Cells

Six-to-eight week old female scid mice were used to establish OCI-My5 tumors. Mice were inoculated subcutaneously with 1×10$^7$ cells at the base of the tail. Mice were treated intravenously with PBS or 100 µg of anti-CD138, anti-dansyl (DNS)-IFNα2, anti-CD138-IFNα2, anti-CD20-IFNα2$^{YNS}$, anti-CD138-IFNα2$^{YNS}$ on days 14, 16, 18 post tumor challenge. Each group consisted of eight mice. Bidirectional tumor growth was measured throughout the experiment, and mice were sacrificed when tumors reached 1.5 cm as per institutional guidelines. For U266 tumors, experiments were carried out as described above except that NOD-scid IL2rγ$^{null}$ (NSG) mice were used. All animal studies were performed in compliance with the U.S. Department of Health and Human Services Guide for the Care and Use of Laboratory Animals and were approved by the UCLA Animal Research Committee.

Treatment of Primary Myeloma Cells from Patients

Patients with active myeloma were biopsied while off therapy and myeloma cells isolated by negative antibody selection to >95% purity. Cells were incubated with 25 or 100 nM of anti-CD138, anti-CD138-IFNα2 or anti-CD138-

IFNα2$^{YNS}$ for 72 hours. Percent viable cell recovery was determined by trypan blue staining, with untreated control cells designated as 100%.

Results

Figure 13A:
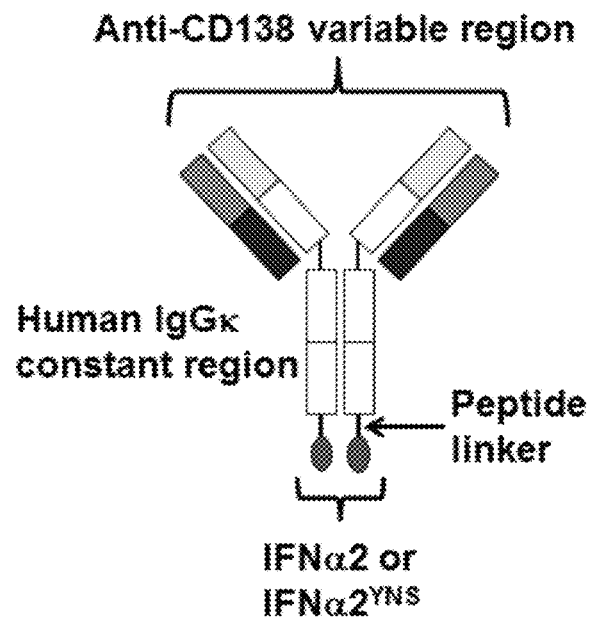
FIGS. 13A and 13B illustrate production of IFNα2 fusion proteins.
Figure 13B:
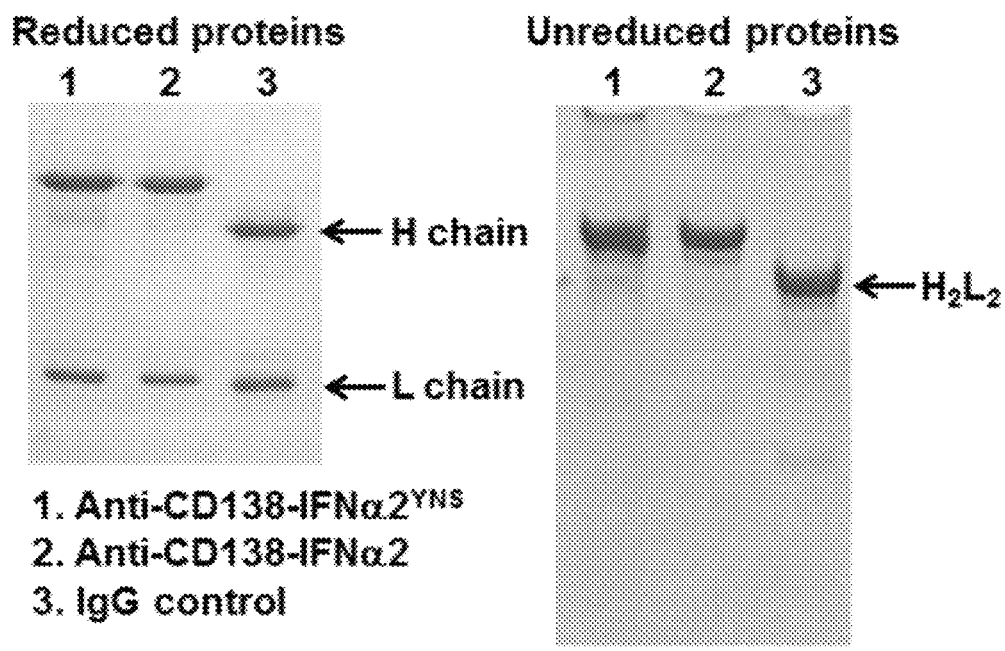

Production and Characterization of Anti-CD138-IFNα2 and Anti-CD138-IFNα2$^{YNS}$ Fusion Proteins The aim of this study was to test the effectiveness of using antibodies specific for CD138 to target IFN to multiple myeloma cells. The approach was to genetically fuse IFN to the end of the $C_H3$ domain of human IgG1 containing the V regions from the anti-CD138 antibody B-B4 (Wijdenes et al. (1996) *Br. J. Haematol.*, 94: 318-323). We elected to target IFNα2, which has been used successfully in the treatment of multiple myeloma in the clinic. IFNβ binds to the same receptor as IFNα but has a greater affinity and activity than IFNα2. However, we found that fusion of human IFNβ to IgG resulted in a >100-fold decrease in activity (data not shown). As an alternative approach, we also elected to target IFNα2 containing mutations at three positions, H57Y/E58N/Q61S (anti-CD138-IFNα2$^{YNS}$). These mutations result in a 60-fold increased affinity for IFNAR1 and a large increase in anti-proliferative activity compared to wildtype IFNα2 (Kalie et al. (2007) *J. Biol. Chem.*, 282: 11602-11611). Anti-CD138 IgG1 either unfused or fused to human IFNα2 or IFNα2$^{YNS}$ (FIG. 13A) was expressed in stable CHO transfectants. Purified proteins were characterized with respect to their size and assembly status and were found to possess heavy (H) and light (L) chains of the appropriate molecular weight and assemble into complete $H_2L_2$ molecules (FIG. 13B) that bound antigen (data not shown).

IFNα2 Fusion Proteins Inhibit the Growth of HMCLs

Multiple myeloma is characterized by biological and genetic heterogeneity (Carrasco et al. (2006) *Cancer Cell* 9: 313-325; Drexler et al. (2000) *Leukemia*, 14: 777-782; Lombardi et al. (2006) *Genes Chromosomes Cancer*, 46: 226-238; Moreaux et al. (2011) *Haematologica*, 96: 574-582) and often differ in their responses to various drugs and treatments. Therefore, we assembled a panel of thirteen HMCLs (XG-1, XG-2, OPM-1, OPM-2, S6B45, delta 47, RPMI 8226, 8226/Dox40, U266, OCI-My5, ANBL-6, NCI-H929 and MM1-144) to investigate their response to IFNα and the fusion proteins. The panel includes both hyperdiploid and nonhyperdiploid cells with various chromosomal translocations (Drexler et al. (2000) *Leukemia*, 14: 777-782; Moreaux et al. (2011) *Haematologica*, 96: 574-582; Gabrea et al. (2008) *Genes Chromosomes Cancer*, 47: 573-590). All of the HMCLs were bound by anti-CD138 IgG, indicating that they express CD138 (data not shown).

Figure 14:
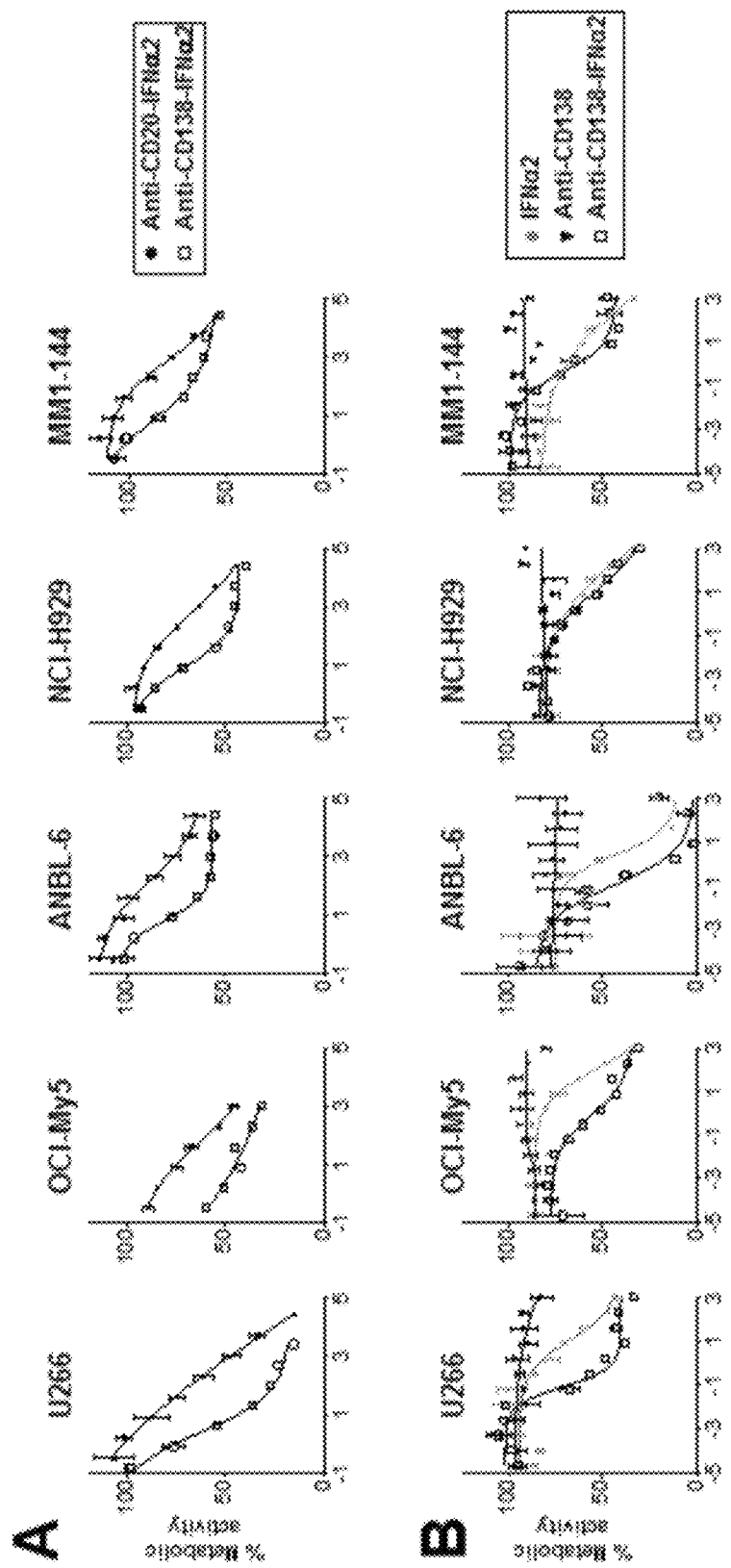
FIG. 14, panels A-C, illustrates growth inhibition of HMCLs by IFNα2 fusion proteins. Panel A) The indicated cell lines were incubated with varying concentrations (0.3 pM-25 nM for all cell lines except OCI-My5 which was tested at 0.3 pM-1 nM) of anti-CD20-IFNα2 or anti-CD138-IFNα2 for 3 days. Cellular metabolic activity was measured using the MTS assay. The experiment was performed in triplicate for each concentration. Panels B and C) HMCLs were treated with 0.00002 pM-1 nM of IFNα2, anti-CD138, anti-CD138-IFNα2, IFNβ, anti-CD20-IFNα2$^{YNS}$ and anti-CD138-IFNα2$^{YNS}$ for 3 days (U266, OCI-My5, NCI-H929, and MM1-144), or 7 days (ANBL-6) and analyzed for metabolic activity by MTS assay. The experiment was performed in triplicate for each concentration. For all experiments, error bars indicate the standard deviation of the measurements. The experiment shown in panel A is different from that shown in panels B and C. The date shown in Panel A were shown previously in FIG. 2.

To determine if the HMCLs were sensitive to treatment and if targeted IFNα2 was more effective, cells were incubated with varying concentrations of fusion proteins for 3 days and metabolic activity assessed by MTS assay. Anti-CD138-IFNα2 was used to target IFNα while anti-CD20-IFNα2 was used as an untargeted control since HMCLs do not express CD20. HMCLs showed different responses to treatment. Under these conditions both fusion proteins had little or no effect on XG-1, XG-2, OPM-1, OPM-2, and delta 47 while some effect was observed only at high concentrations for S6B45, RPMI 8226, and 8226/Dox40 (data not shown). However, the targeted anti-CD138-IFNα2 was >10-fold more effective than untargeted anti-CD20-IFNα2 for U266, OCI-My5, ANBL-6, NCI-H929 and MM1-144 (FIG. 14, panel A). Therefore, the IFNα2 fusion protein that is targeted to an antigen present on myeloma cells appeared to be more effective than an untargeted fusion protein against a number of HMCLs representing multiple myeloma with various molecular abnormalities.

In a different experiment, anti-CD138-IFNα2 fusion protein was compared to equimolar concentrations of anti-CD138 alone and recombinant IFNα2 alone. Anti-CD138-IFNα2 was more effective than recombinant IFNα2 in inhibiting the growth of OCI-My5, ANBL-6, and MM1-144, but not NCI-H929. Comparison of $IC_{50}$ between anti-CD138-IFNα2 and IFNα2 calculated from the data shown in FIG. 14, panel B using Prism software confirmed that CD138-IFNα2 was more effective than IFNα2 in inhibiting the growth of U266 ($8.3 \times 10^{-5}$ versus $1.2 \times 10^{-2}$ pM), OCI-My5 ($8.4 \times 10^{-4}$ versus 0.14 pM), ANBL-6 ($1.1 \times 10^{-4}$ versus $2.6 \times 10^{-3}$ pM), and MM1-144 ($4.2 \times 10^{-4}$ versus $8.0 \times 10^{-2}$ pM). The mutant fusion proteins were compared to recombinant IFNβ. We found that IFNβ, anti-CD20-IFNα2$^{YNS}$ and anti-CD138-IFNα2$^{YNS}$ showed similar ability to inhibit the growth of OCI-My5, ANBL-6, NCI-H929 and MM1-144 (FIG. 14, panel C). However, for U266 anti-CD138-IFNα2$^{YNS}$ was more effective in growth inhibition ($IC_{50}=2.1 \times 10^{-7}$ pM) than IFNβ ($2.8 \times 10^{-4}$ pM) or anti-CD20-IFNα2$^{YNS}$ ($2.4 \times 10^{-4}$ pM). Unfused anti-CD138 had no effect against any of the five cell lines (FIG. 14, panel B).

Figure 15A:
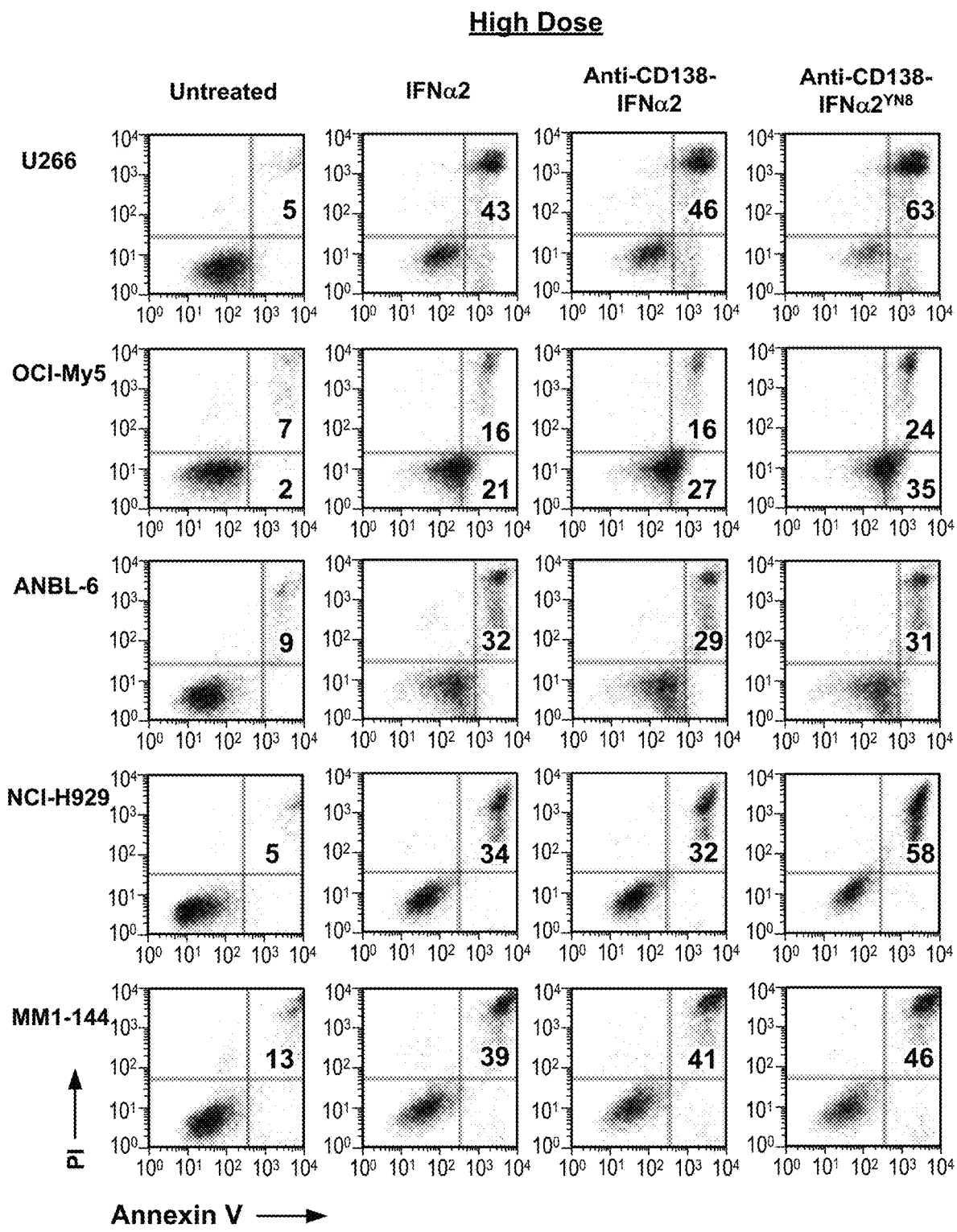
FIGS. 15A and 15B show that treatment with IFNα2 and fusion proteins induces apoptosis.
Figure 15B:
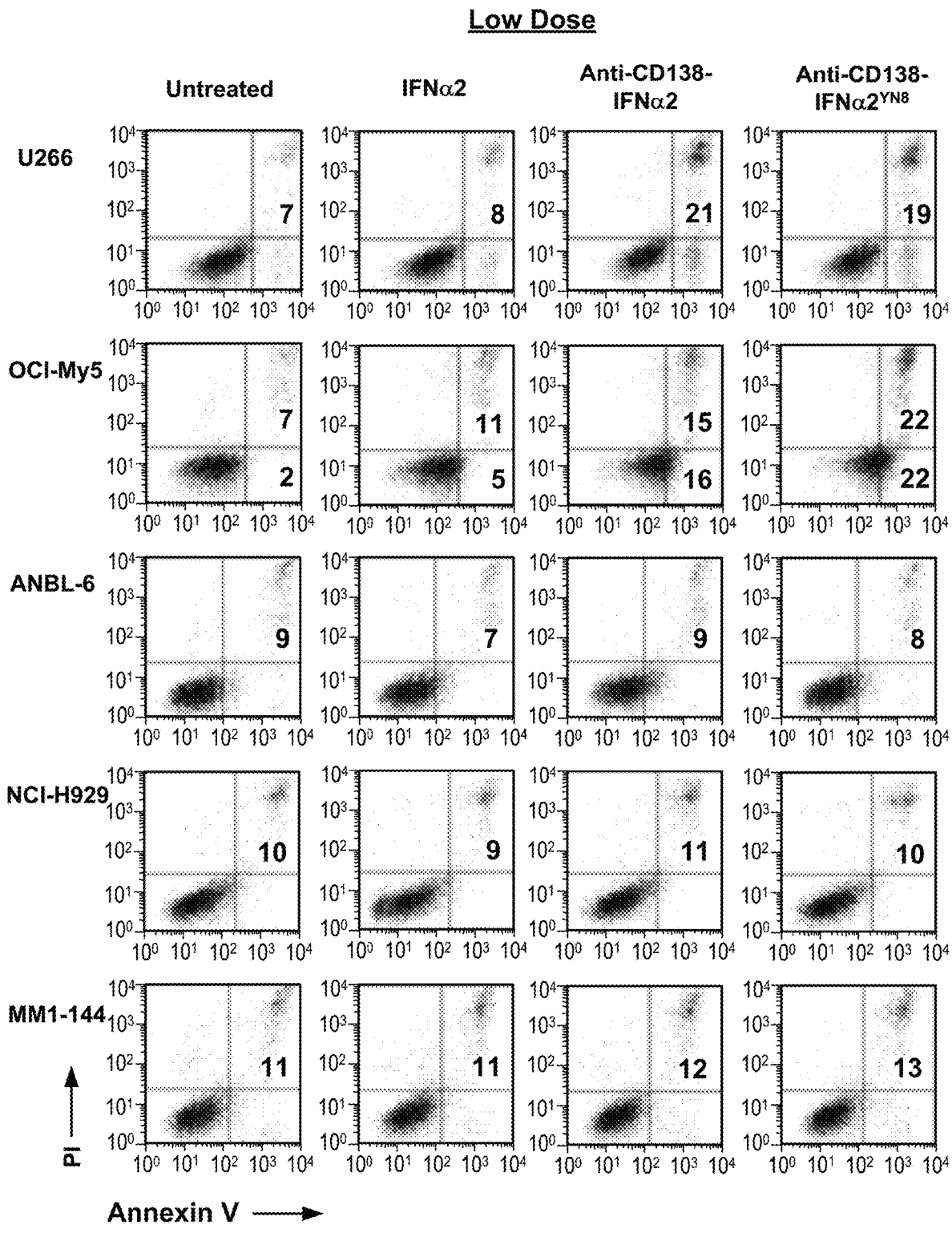

To determine if apoptosis was being induced in the HMCLs, cells were treated for 3 days at high (500 pM) or low (1 pM or 5 pM for OCI-My5) concentrations of IFNα2 and fusion proteins, stained using Alexa Fluor 488-labeled Annexin V and PI and examined by flow cytometry. When treated at 500 pM, IFNα2 and the fusion proteins caused apoptosis in all HMCLs (FIG. 15A). For U266 and NCI-H929, hgher levels of apoptosis were observed with anti-CD138-IFNα2$^{YNS}$ than with IFNα2 or anti-CD138-IFNα2. In contrast, different results were observed at low concentrations. At low concentrations, IFNα2 and the fusion proteins did not cause apoptosis in ANBL-6, NCI-H929, and MM1-144 (FIG. 15B). However at low concentrations, anti-CD138-IFNα2 and anti-CD138-IFNα2$^{YNS}$ were able to induce apoptosis in U266 and OCI-My5 while IFNα2 had no effect. These data suggest that although the efficacy appeared to be similar at high doses, at low doses, targeted fusion protein can have a greater effect than IFNα2 alone as in the case of U266 and OCI-My5. IFNβ and anti-CD138-IFNα2$^{YNS}$ induced similar levels of apoptosis in U266, NCI-H929 and MM1-144 at both 500 pM and 1 pM concentrations (data not shown).

Figure 16A:
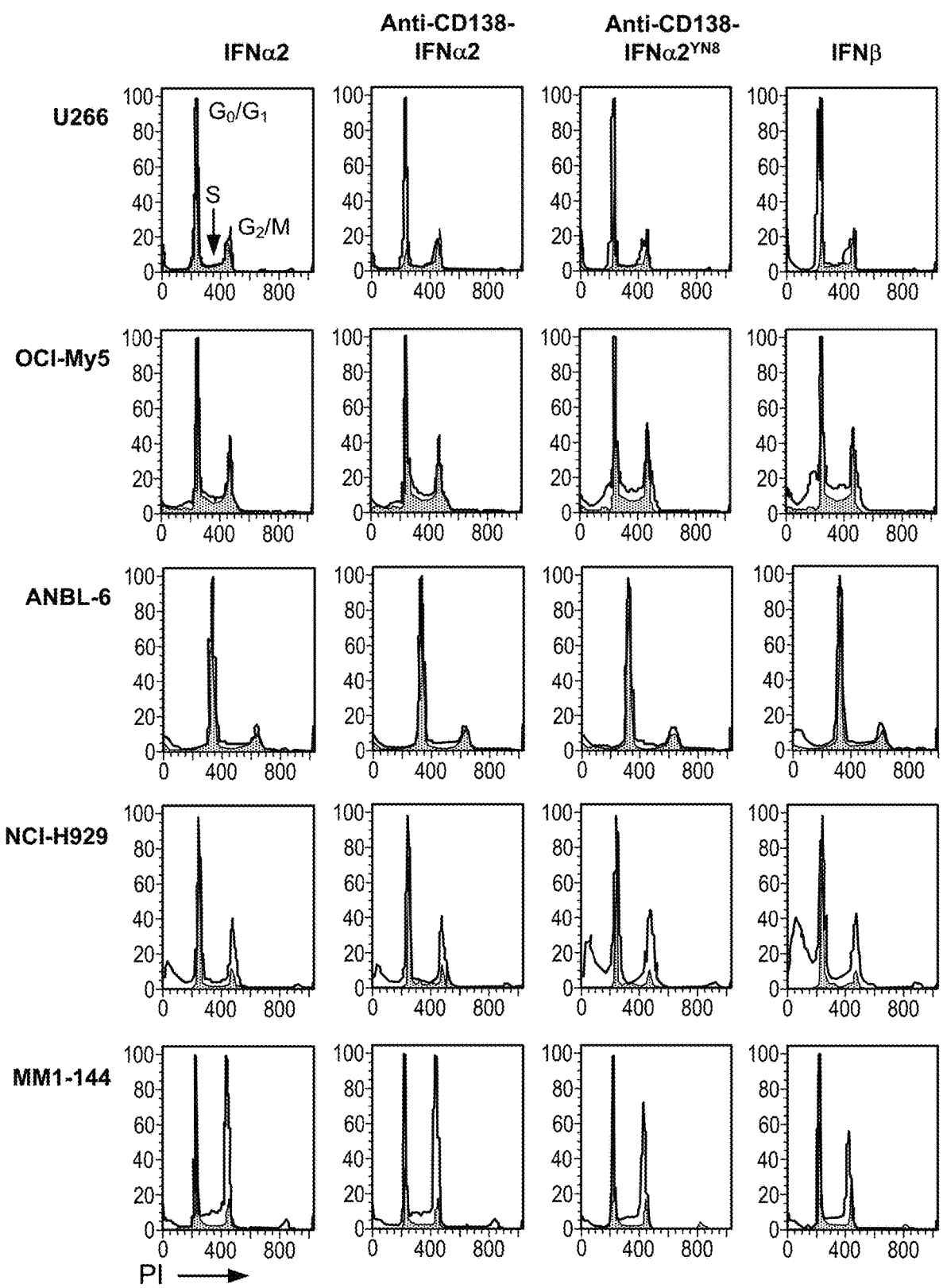

IFNα2 and Fusion Proteins Can Induce Alterations in Cell Cycle Progression and Senescence in Some HMCLs HMCLs were also analyzed for changes in cell cycle progression following treatment with IFNα, IFNβ or fusion proteins for 4 days. All treatments resulted in increases in the percentage of dead cells with sub-$G_0/G_1$ DNA content (FIG. 16A and Table 5). The most profound cell cycle changes were observed for NCI-H929 and MM1-144, which showed large increases in the percentage of cells in $G_2/M$ with concomitant decreases in cells in $G_1$. For the other HMCLs, the changes were more subtle. ANBL-6 showed a decrease in cells in S phase while U266 and OCI-My5 showed only small cell cycle changes following treatment. In all cases, comparable changes were seen following treatment with IFNα2, IFNβ, anti-CD138-IFNα2 and anti-CD138-IFNα2$^{YNS}$.

TABLE 5

The percentages of live cells in different phases of the cell cycle after treatment with the indicated proteins are shown.

| | % $G_1$ | % S | % $G_2$/M | >$G_2$ | Sub $G_0$/$G_1$ |
|---|---|---|---|---|---|
| U266 | | | | | |
| Untreated | 42.6 | 28.5 | 17.4 | 10.3 | 5.2 |
| IFNα2 | 52.5 | 23.6 | 14.3 | 5.7 | 14.0 |
| Anti-CD138-IFNα2 | 53.9 | 21.4 | 15.1 | 5.5 | 13.2 |
| Anti-CD138-IFNα2$^{YNS}$ | 58.5 | 13.1 | 20.2 | 6.4 | 15.9 |
| IFNβ | 58.7 | 12.4 | 20.1 | 7.1 | 17.0 |
| OCI-My5 | | | | | |
| Untreated | 37.4 | 41.7 | 19.0 | 0.1 | 9.4 |
| IFNα2 | 30.1 | 45.6 | 19.2 | 1.2 | 19.0 |
| Anti-CD138-IFNα2 | 25.6 | 49.0 | 20.5 | 1.5 | 17.9 |
| Anti-CD138-IFNα2$^{YNS}$ | 23.8 | 50.3 | 20.5 | 0.0 | 24.2 |
| IFNβ | 21.8 | 54.2 | 19.0 | 0.0 | 29.5 |
| ANBL-6 | | | | | |
| Untreated | 51.8 | 25.3 | 10.1 | 4.6 | 11.3 |
| IFNα2 | 64.8 | 14.3 | 17.0 | 0.0 | 19.8 |
| Anti-CD138-IFNα2 | 63.6 | 14.0 | 18.0 | 0.0 | 19.6 |
| Anti-CD138-IFNα2$^{YNS}$ | 64.1 | 14.7 | 17.7 | 0.0 | 10.8 |
| IFNβ | 60.5 | 15.4 | 18.8 | 0.0 | 26.1 |
| NCI-H929 | | | | | |
| Untreated | 62.1 | 21.4 | 11.9 | 2.7 | 1.8 |
| IFNα2 | 41.5 | 21.7 | 25.4 | 7.6 | 21.2 |
| Anti-CD138-IFNα2 | 41.9 | 21.0 | 24.3 | 8.2 | 18.9 |
| Anti-CD138-IFNα2$^{YNS}$ | 43.0 | 18.0 | 26.6 | 8.0 | 30.4 |
| IFNβ | 41.2 | 22.1 | 23.4 | 7.8 | 37.4 |
| MM1-144 | | | | | |
| Untreated | 48.5 | 29.4 | 13.9 | 7.0 | 5.1 |
| IFNα2 | 21.0 | 31.5 | 34.2 | 11.6 | 10.3 |
| Anti-CD138-IFNα2 | 22.6 | 29.9 | 34.3 | 11.2 | 11.3 |
| Anti-CD138-IFNα2$^{YNS}$ | 27.7 | 30.0 | 30.7 | 9.4 | 11.9 |
| IFNβ | 29.0 | 33.7 | 26.7 | 8.6 | 11.7 |

Phosphorylated retinoblastoma protein (ppRB), which is regulated by interactions between cyclin D and cyclin-dependent kinases, is an indicator of cell cycle progression. Since cell cycle progression was blocked in some HMCLs, we determined the levels of ppRB by Western blotting (FIG. 16B). We did not detect any ppRB in U266, which has a biallelic deletion of the RB gene (Corradini et al. (1994) Leukemia, 8: 758; Dao et al. (1994) Leukemia, 8: 1280; Juge-Morineau et al. (1995) Br. J. Haematol., 91: 664-667). For NCI-H929, MM1-144 and OCI-My5, ppRb levels were decreased following treatment with IFNα2, anti-CD138-IFNα2 and anti-CD138-IFNα2$^{YNS}$, consistent with these proteins having a negative effect on cell division. Similar results were obtained with ANBL-6 (data not shown).

Cell cycle arrest may be an indicator of replicative senescence. Although this arrest has been described to occur in $G_0$/$G_1$ (reviewed in Kong et al. (2011) J. Aging Res., 2011: 963172), $G_2$ arrest has also been reported (Mao et al. (2012) Aging, 4: 431; Olsen et al. (2002) Oncogene, 21: 6328; Wada et al. (2004) Nat. Cell Biol., 6: 215-226; Zhu et al. (1998) Genes Dev., 12: 2997-3007). IFNα2 has been reported to induce senescence in endothelial cells (Pammer et al. (2006) Lab. Invest. 86: 997-1007), but no such activity has yet been reported in myeloma. One marker for senescence is β-gal activity at pH 6, which is a barometer of increased lysosomal content in the cells undergoing senescence. To assay for senescence, HMCLs were treated for 3 days with IFNα2, anti-CD138, anti-CD138-IFNα2, or anti-CD138-IFNα2$^{YNS}$ and β-gal activity detected by flow cytometry (FIG. 16C). NCI-H929 and MM1-144 showed increases in β-gal activity following treatment with IFNα2, anti-CD138-IFNα2 and CD138-IFNα2$^{YNS}$ but not with anti-CD138. In the case of NCI-H929, targeting with anti-CD138-IFNα2 and CD138-IFNα2$^{YNS}$ had a greater effect than with IFNα2 alone. Interestingly, OCI-My5 showed an increase only following treatment with anti-CD138-IFNα2$^{YNS}$. U226 showed no increase under any conditions; similarly, ANBL-6 also showed no increases (data not shown).

Figure 16D:
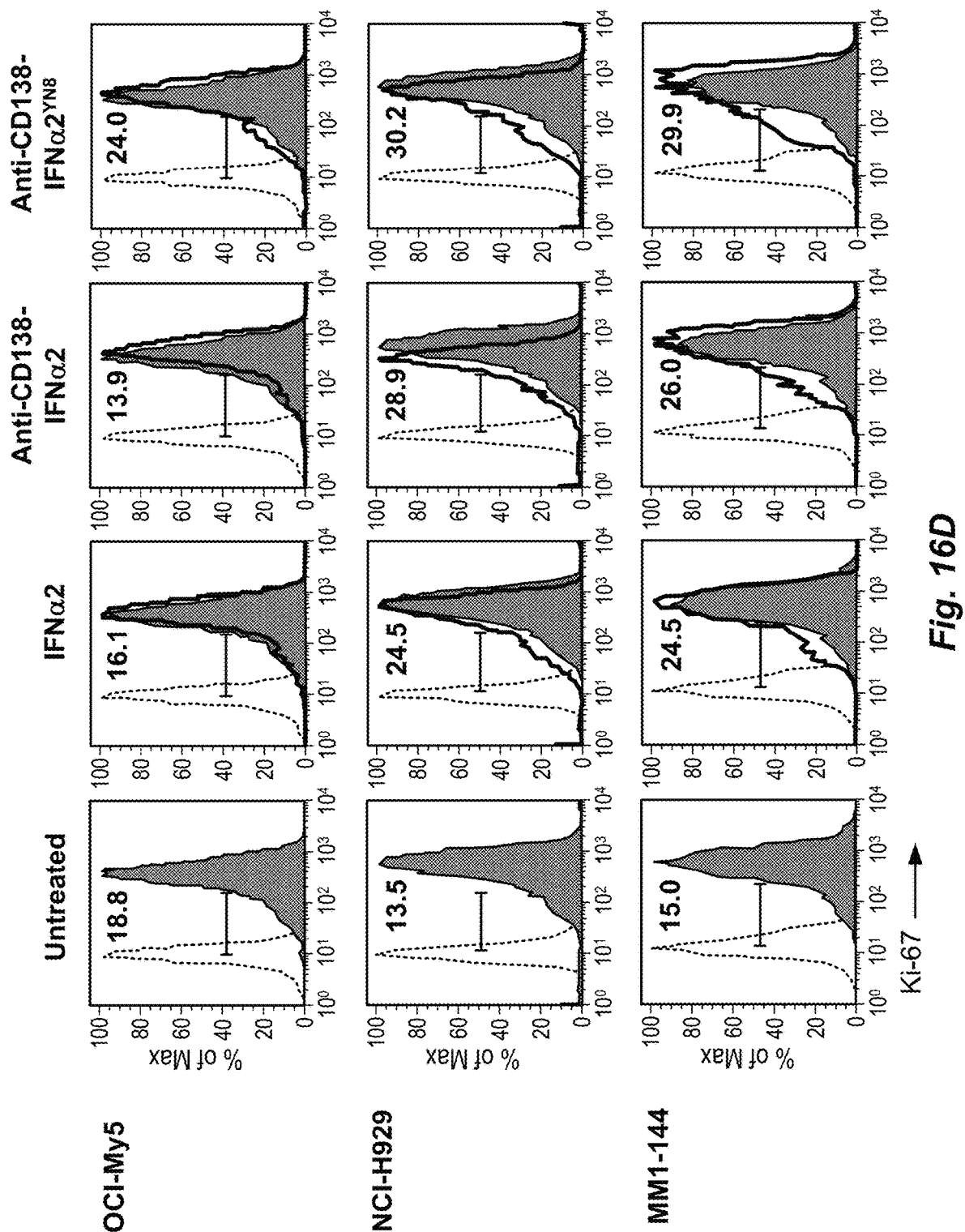

Ki-67 protein is present during all active phases of the cell cycle but is absent from cells that have ceased dividing, including senescent cells. To quantify the number of non-dividing cells, HMCLs were treated for 3 days and Ki-67 expression was determined by flow cytometry. The percentage of Ki-67 (non-dividing) cells are shown in FIG. 16D. If cells cease dividing in response to treatment, the percentage of Ki-67 cells should increase as compared to untreated cells. Indeed, this was what we observed for NCI-H929 and MM1-144. Treatment with IFNα2, anti-CD138-IFNα2, and anti-CD138-IFNα2$^{YNS}$ resulted in more Ki-67 cells as compared to untreated control. For OCI-My5, an increase in Ki-67 cells was observed only with anti-CD138-IFNα2$^{YNS}$, which was also the only treatment that resulted in increased β-gal activity (FIG. 16C). Thus it appears that IFNα2 can induce senescence in some HMCLs. In particular for NCI-H929 and MM1-144, the accumulation of cells in $G_2$/M and increases in β-gal activity and Ki-67 cells are evidence that these cell lines are undergoing senescence in response to IFNα2 and fusion protein treatment.

Expression of the transcription factor IFN regulatory factor-4 (IRF-4) has been shown to be required for survival of multiple myeloma cells regardless of their genetic etiology, with even small changes to IRF-4 levels resulting in cell death (Shaffer et al. (2008) Nature, 454: 226-231). Therefore, we wanted to determine if treatment resulted in changes to IRF-4 levels. While IRF-4 levels were unchanged in NCI-H929, MM1-144, OCI-My5 and ANBL-6 (data not shown), there was a decrease in IRF-4 expression in U266 after treatment with IFNα2 and fusion proteins (FIG. 16B). The observed decrease was similar when U266 was treated with IFNα2, anti-CD138-IFNα2 and anti-CD138-IFNα2$^{YNS}$. Thus for U266, the fusion proteins interfere with tumor growth at least in part by causing a decrease in IRF-4 expression.

Fusion Proteins are Effective in Murine Xenograft Models of Multiple Myeloma

Figure 17A:
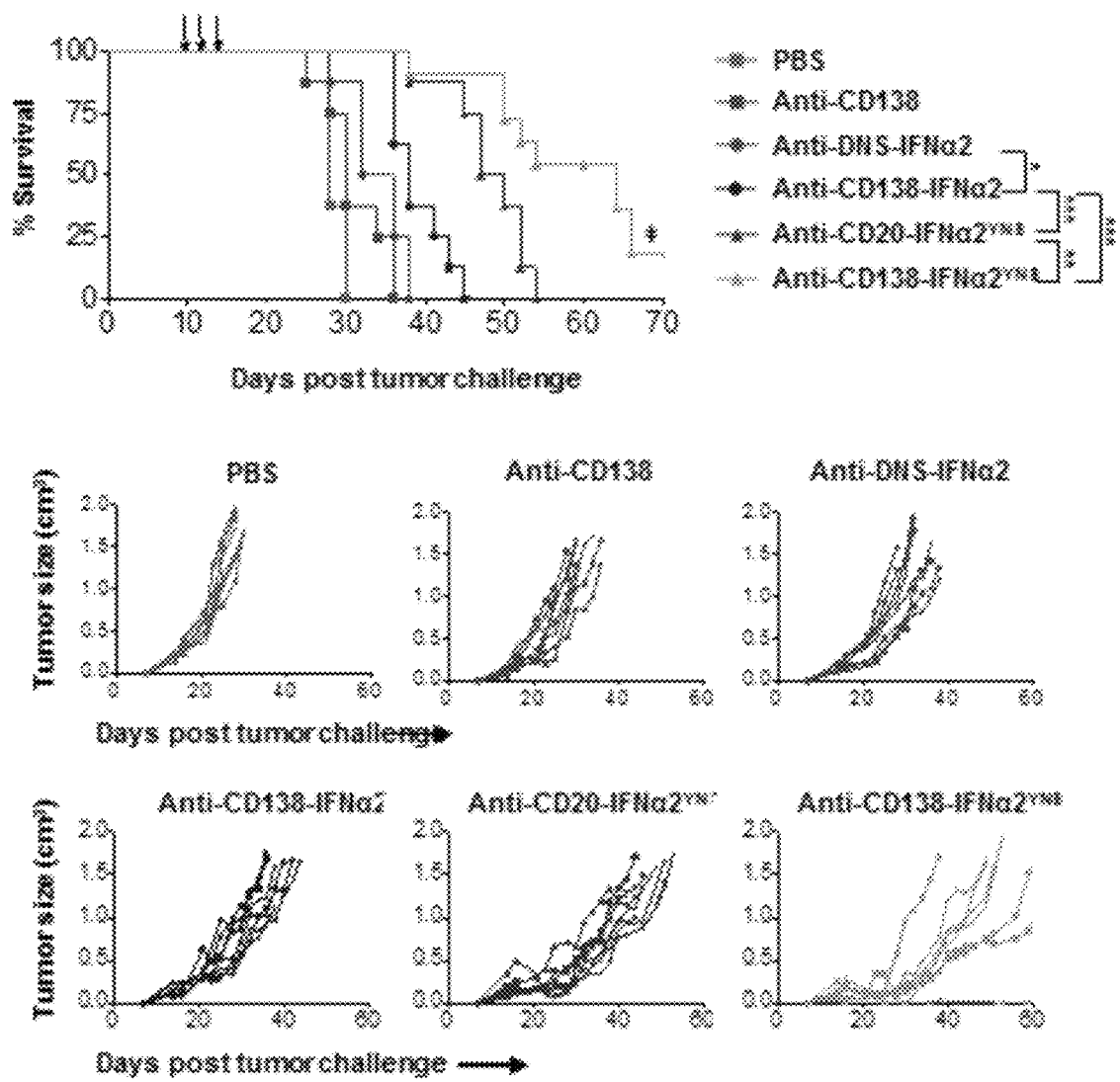
FIGS. 17A and 17B show that fusion proteins confer protection to mice in two xenograft models of multiple myeloma.

To determine if the fusion proteins are protective against multiple myeloma in vivo, we used xenograft models of OCI-My5 and U266 tumors. In the OCI-My5 model, tumors were established in scid mice, which lack mature T and B cells. Mice were treated on days 14, 16 and 18. To treat the mice, we used unfused anti-CD138, an untargeted fusion protein with an irrelevant specificity for the hapten dansyl (DNS; anti-DNS-IFNα2), untargeted anti-CD20-IFNα2$^{YNS}$, or targeted anti-CD138-IFNα2 and anti-CD138-IFNα2$^{YNS}$. We would not expect anti-CD20-IFNα2$^{YNS}$ to target to any cells in the mice since it is specific for human CD20. Survival and tumor size were monitored (FIG. 17A). The survival of anti-CD138 treated mice did not differ significantly from PBS treated mice (p=0.079), consistent with our failure to observe anti-tumor activity by anti-CD138 in vitro. All of the fusion proteins including those that were not targeted to CD138 showed some level of protection. However, targeting resulted in significant improvements to survival with greater protection observed with anti-CD138-IFNα2 than with untargeted anti-DNS-IFNα2 (p=0.021) and anti-CD138-IFNα2$^{YNS}$ than with untargeted anti-CD20-IFNα2$^{YNS}$ (p=0.0075). In addition, anti-CD138-IFNα2$^{YNS}$ was more protective than anti-CD138-IFNα2 (p<0.0001).

Surprisingly, the untargeted anti-CD20-IFNα2$^{YNS}$ was more effective than the targeted anti-CD138-IFNα2 fusion protein (p=0.0007).

Figure 17B:
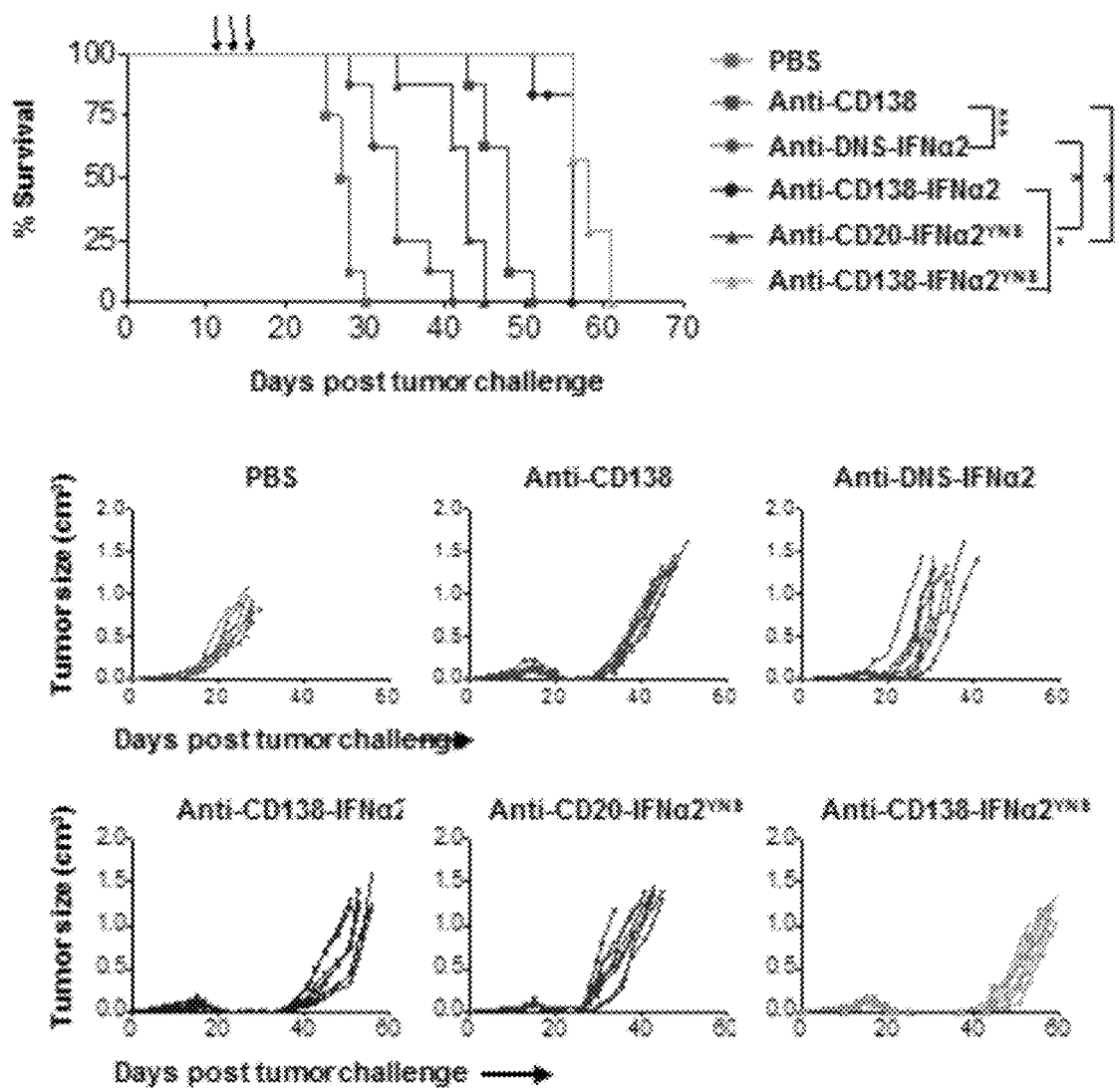

In the U266 tumor model, NSG mice were used. NSG mice are severely immunocompromised, lacking mature T and B cells, functional NK cells and are deficient in cytokine signaling. Mice were treated on days 14, 16 and 18 as described above. All treatment groups, including anti-CD138 and untargeted IFNα2 fusion proteins, showed significant improvements in survival when compared with the untreated PBS control (p≤0.0003; FIG. 17B). However, the targeted anti-CD138-IFNα2 and anti-CD138-IFNα2$^{YNS}$ displayed the highest levels of protection. Although anti-CD138-IFNα2$^{YNS}$ was more effective than anti-CD138-IFNα2 for U266 in in vitro assays, the two proteins had similar protective effects in vivo (p=0.05). Interestingly, anti-CD138 also showed significant protection when compared with the untargeted anti-DNS-IFNα2 (p<0.0001) and anti-CD20-IFNα2$^{YNS}$ (p=0.0024) in this murine model even though it showed no growth inhibition activity in vitro (FIG. 14). Untargeted anti-CD20-IFNα2$^{YNS}$ was more effective than untargeted anti-DNS-IFNα2 (p=0.001), consistent with its greater IFN activity.

Figure 18:
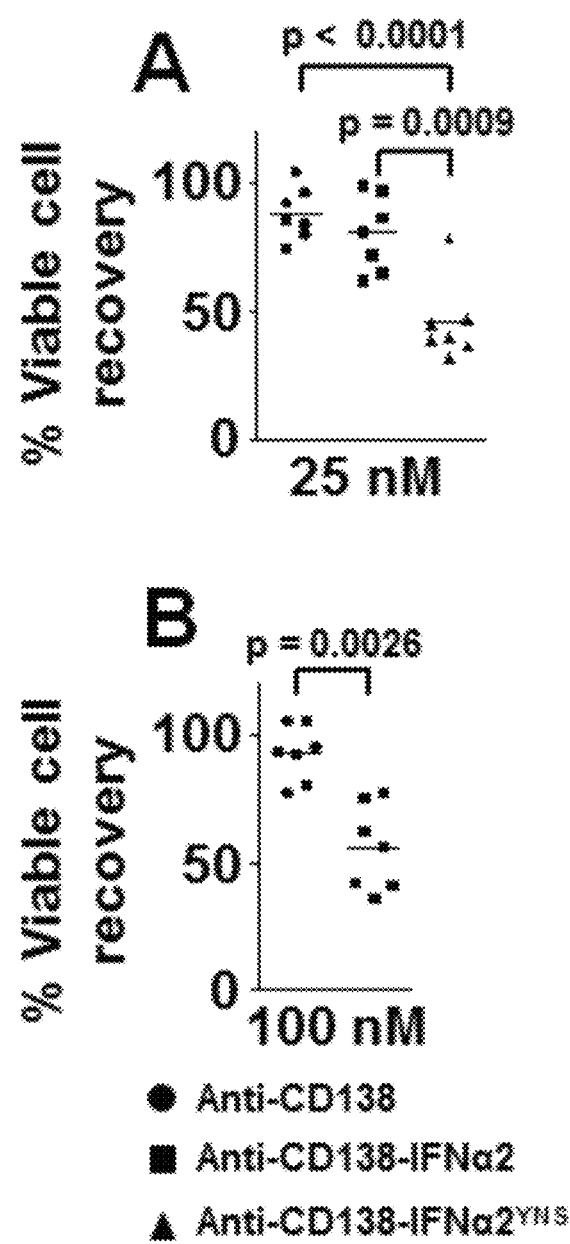
FIG. 18, panels A and B show that fusion proteins are effective against primary myeloma cells. Panel A) Purified multiple myeloma cells from seven patients were incubated with 25 nM of the indicated proteins for 72 hours. Cell viability was determined by trypan blue staining by comparing the number of recovered viable cells to that of untreated control cells. Data also shown in FIG. 5A. Panel B) Purified multiple myeloma cells from 7 patients were incubated with 100 nM of the indicated proteins for 72 hours. Cell viability was assessed as described above.

Fusion Proteins are Effective Against Primary Multiple Myeloma Cells from Patients To determine if the fusion proteins are effective against primary tumors, multiple myeloma patient cells were treated with anti-CD138, anti-CD138-IFNα2 or anti-CD138-IFNα2$^{YNS}$ for 72 hours and the percentage of viable recovered cells compared to untreated cells was determined by trypan blue exclusion. As expected, untreated primary cells demonstrated no increase in cell number during this time as freshly obtained primary multiple myeloma cells do not proliferate ex vivo. Not surprisingly, there was some variability in response among the seven patients' cells when the proteins were tested at 25 nM (FIG. 18, panel A). Anti-CD138, anti-CD138-IFNα2 and IFNα2 (data not shown) had little effect at this concentration. In contrast, anti-CD138-IFNα2$^{YNS}$ treatment resulted in significant decreases to cell viability when compared to anti-CD138 (p<0.0001) or to anti-CD138-IFNα2 (p=0.0009). Although anti-CD138-IFNα2 was not effective at 25 nM, at 100 nM anti-CD138-IFNα2 was able to significantly reduce cell viability (p=0.0026; FIG. 18, panel B). These data show that although both fusion proteins can affect cell viability, fusion with the higher affinity IFNα2$^{YNS}$ is more effective at lower concentrations against primary patient cells. In a few primary samples where sufficient cell numbers were available to perform apoptosis assays, fusion proteins appeared to induce apoptotic death (data not shown).

Discussion

IFNα therapy has been used for treatment of multiple myeloma, but disagreement exists as to its efficacy. However, meta-analysis of 17 trials including 2333 patients who received combination IFNα-chemotherapy or chemotherapy alone showed significantly superior outcomes in IFNα treated patients for relapse-free and overall survival; similarly, meta-analyses of maintenance treatments also showed significantly better outcomes in the IFNα treatment arms than in untreated controls (Fritz et al. (2000) *Ann. Oncol.,* 11: 1427-1436), underscoring the fact that IFNα can be an effective therapeutic against multiple myeloma. Some of the major problems for IFNα2 therapy are systemic toxicity and short in vivo half-life. Our approach to circumventing these problems was to fuse IFNα2 to anti-CD138 IgG1 to increase its half-life and by targeting, deliver an effective dose of IFNα2 to the tumor site without systemic toxicity. We have previously used this approach successfully in the treatment of human B cell lymphoma using an anti-CD20-IFNα2 fusion protein and have shown that it is significantly more effective than anti-CD20 antibody alone or the combination of anti-CD20 and IFNα2 in mice (Xuan et al. (2010) *Blood,* 115: 2864-2871).

Multiple myeloma is characterized by significant heterogeneity and indeed our studies have shown heterogeneity in the response of different HMCLs to treatment with IFNα and fusion proteins. Our studies as well as others (Crowder et al. (2005) *Blood.,* 105: 1280-1287; Gomez-Benito et al. (2005) *FEBS Lett.,* 579: 6217-6222) have shown that not all multiple myeloma cells are responsive to treatment with IFNa; the responsiveness of HMCLs does not always correlate with the level of IFNAR expression (Gomez-Benito et al. (2005) *FEBS Lett.,* 579: 6217-6222). For HMCLs that were sensitive, fusion proteins containing wildtype IFNα2 or mutant IFNα2$^{YNS}$ were comparable to or better than IFNa alone in all of the in vitro assays, suggesting that targeting via anti-CD138 enhances efficacy. The inhibition of proliferation observed resulted at least in part from the induction of apoptosis, alterations in cell cycle and senescence.

Replicative senescence is recognized as a potential mechanism to prevent tumorigenesis and cancer progression. In vitro, senescent cells do not divide but are viable and metabolically active. IFNα has been shown to induce senescence in endothelial cells (Pammer et al. (2006) *Lab. Invest.* 86: 997-1007), and IFNβ has been shown to induce senescence in human papilloma virus-transformed keratinocytes (Chiantore et al. (2012) *PLoS One,* 7: e36909), biliary epithelial cells (Sasaki et al. (2008) *Free Radic. Res.,* 42: 625-632), and human fibroblasts (Moiseeva et al. (2006) *Mol. Biol. Cell,* 17: 1583-1592). However, IFNα-induced senescence in multiple myeloma has not been reported to date. One novel finding from our studies is that IFNα2 and fusion proteins can induce cellular senescence in some HMCLs as indicated by increases in senescence-associated β-gal activity and decreases in Ki-67 levels. These changes were observed in NCI-H929 and MM1-144 cells when treated with IFNα2, anti-CD138-IFNα2 and anti-CD138-IFNα2$^{YNS}$, while OCI-My5 displayed such changes only when cells were treated with anti-CD138-IFNα2$^{YNS}$. Alternations in cell cycle caused by IFNα have been reported (Crowder et al. (2005) *Blood.,* 105: 1280-1287; Gomez-Benito et al. (2005) *FEBS Lett.,* 579: 6217-6222; Arora et al. (1998) *J. Biol. Chem.,* 273: 11799-11805; Arulampalam et al. (2011) *Exp. Cell Res.,* 317: 9-19; Minami et al. (2000) *Exp. Hematol.,* 28: 244-255), and in our study, NCI-H929 and MM1-144 were blocked at the $G_2$/M phase. Although most studies have found accumulation of senescent cells in $G_1$, $G_2$-arrested senescent cells have also been reported (Mao et al. (2012) *Aging,* 4: 431; Olsen et al. (2002) *Oncogene,* 21: 6328; Wada et al. (2004) *Nat. Cell Biol.,* 6: 215-226; Zhu et al. (1998) *Genes Dev.,* 12: 2997-3007). HMCLs in which senescence was detected also had populations of apoptotic cells in response to treatment. Since senescent cells are thought to be resistant to apoptosis, it may be that subpopulations of cells are responding to IFNα2 differentially. Indeed, a growing hypothesis is that low doses of chemotherapeutic drugs induce senescence while high doses trigger apoptosis (Rebbaa et al. (2003) *Oncogene,* 22: 2805-2811; Zheng et al. (2004) *Cancer Res.* 64: 1773-1780). The observation of both senescence and apoptosis in these HMCLs may also reflect heterogeneity of the uncloned cell lines.

Expression of IRF-4 is associated with many lymphoid malignancies. IRF-4 acts as a master regulator of an aberrant, malignancy-specific regulatory network which influences metabolism, membrane biogenesis, cell cycle progression, cell death and transcriptional regulation in myeloma cells (Verdelli et al. (2009) *Hematol. Oncol.* 27: 23-30). IRF-4 inhibition has been found to be toxic to myeloma cell lines regardless of the transforming oncogenic mechanism (Shaffer et al. (2008) *Nature,* 454: 226-231). We found that IFNα2, anti-CD138-IFNα2 and anti-CD138-IFNα2$^{YNS}$ treatment results in decreased expression of IRF-4 in U266 but not in the other HMCLs tested. Thus decreased expression of IRF-4 may contribute to the anti-tumor effects seen in U266.

One of the major challenges in translational research is to determine if in vitro assays are predictive of in vivo outcome. As was observed in vitro, targeting improved the efficacy of IFNα in two in vivo models with anti-CD138-IFNα2 always more effective than untargeted anti-DNS-IFNα2 and anti-CD138-IFNα2$^{YNS}$ always more effective that untargeted anti-CD20-IFNα2$^{YNS}$. However, other interesting and unexpected effects were also observed in vivo. Surprisingly, in the OCI-My5 model the untargeted anti-CD20-IFNα2$^{YNS}$ was more effective than the targeted anti-CD138-IFNα (but less effective than targeted anti-CD138-IFNα2$^{YNS}$) even though in in vitro studies, anti-CD138-IFNα2 was more effective than anti-CD20-IFNα2$^{YNS}$ with $IC_{50}$ of $8.4 \times 10^{-4}$ pM versus $2.3 \times 10^{-3}$ as calculated from the MTS assay (FIG. 14). The superior efficacy of anti-CD138-IFNα2$^{YNS}$ in vitro and in vivo and the ability of anti-CD20-IFNα2$^{YNS}$ to provide protection in mice suggest that OCI-My5 may be highly sensitive to IFNα2$^{YNS}$.

Targeting also increased the anti-tumor effects against U266 tumors in NSG mice with anti-CD138-IFNα2 more effective than anti-DNS-IFNα2 and anti-CD138-IFNα2$^{YNS}$ more effective than anti-CD20-IFNα2$^{YNS}$. However, in contrast to what was observed with OCI-My5, the effects of anti-CD138-IFNα2 and anti-CD138-IFNα2$^{YNS}$ were comparable in the U266 in vivo model. This was unexpected given that in vitro, anti-CD138-IFNα2$^{YNS}$ was more effective than anti-CD138-IFNα2 against U266 cells in the MTS assay and in the apoptosis assay at high concentration. However, at low concentrations, anti-CD138-IFNα2 and anti-CD138-IFNα2$^{YNS}$ had comparable ability to induce apoptosis (FIG. 15B), suggesting that the lower concentration may more accurately reflect the in vivo situation. Surprisingly, although anti-CD138 did not display any anti-tumor activity in vitro, anti-CD138 was more effective than the untargeted IFNα2 and untargeted IFNα2$^{YNS}$ fusion proteins in inhibiting tumor growth in vivo, suggesting that tumor cell growth inhibition is achieved at least in part through the effector functions of IgG, which would be observable in vivo but not in vitro. Although NSG mice are severely immunocompromised, they do contain functional monocytes and neutrophils (Racki et al. (2010) *Transplantation,* 89: 527), which may be involved in tumor killing via antibody-dependent cell-mediated cytotoxicity (ADCC) (Ravetch and Kinet (1991) *Annu. Rev. Immunol.,* 9: 457-492).

Taken as a whole, our data suggest that targeting of IFNα2 via the anti-CD138 moiety can be an effective strategy in the treatment of multiple myeloma. Both anti-CD138-IFNα2 and anti-CD138-IFNα2$^{YNS}$ were effective against HMCLs in vitro and were able to prolong survival in mice. The higher affinity anti-CD138-IFNα2$^{YNS}$ showed greater activity than anti-CD138-IFNα2 against some HMCLs, primary myeloma cells, and in the OCI-My5 xenograft model, suggesting that IFNs with increased affinity may be more effective. The fusion proteins may prove to be even more effective in the treatment of human patients since the immunomodulatory activities of human IFNα2 and effector functions such as complement-dependent cytotoxicity and ADCC associated with the human IgG Fc region are not fully functioning in mice. Moreover, fusion of IFNα2 to anti-CD138 should increase the half-life while decreasing the systemic cytotoxicity of IFNα2, making for a more effective therapeutic against multiple myeloma.

Supplemental Methods

Construction of Expression Vectors

The anti-CD138 heavy (H) and light (L) chain variable (V) region amino acid sequences were obtained from US Patent Publication No: 2009/0175863 (U.S. Ser. No. 12/342,285) also published as PCT Publication No: WO2009080829A1 entitled "Agents targeting CD138 and uses thereof" which is incorporated herein by reference for the antibody sequences provided hterein.

$V_H$ sequence:

(SEQ ID NO: 58)
MGWSYIILFLVATATGVHSQVQLQQSGSELMMPGASVKISCKATGYTFS

NYWIQRPGHGLEWIGEILPGTGRTIYNEKFKGKATFTADISSNTVQMLS

SLTSEDSAVYYCARRDYYGNFYYAMDYWGQGTSVTVSS.

$V_L$ sequence:

(SEQ ID NO: 59)
MKSQTQVFIFLLLCVSGAHGDIQMTQSTSSLSASLGDRVTISCSASQGI

NNYLNWYQQKPDGTVELLIYYTSTLQSGVPSRFSGSGSGTDYSLTISNLE

PEDIGTYYCQQYSKLPRTFGGGTKLEIK

The DNA sequence encoding a signal peptide was added 5' of the H chain and L chain V regions (MGWSYIILFL-VATATGVHS (SEQ ID NO:60) and MKSQTQVFI-FLLLCVSGAHG (SEQ ID NO:61), respectively) as well as the nucleotide sequence containing a Kozak ribosomal recognition site (5'-GGATATCCACC-3', SEQ ID NO:62). To facilitate downstream cloning, the sequence 5'-GCTAGCC-3' (SEQ ID NO:63) was added 3' of the H chain V region, and the sequence 5'-CGTAAGTCGACG-3'(SEQ ID NO:64) was added 3' of the L chain V region. The DNA sequence was synthesized using codons optimized for CHO expression (DNA2.0).

The L chain V region flanked by EcoR V and Sal I restriction sites was sequence-verified before cloning into an expression vector containing the human κ L chain constant region. The H chain V region flanked by EcoR V and Nhe I restriction sites was sequence-verified and cloned into an expression vector containing the human γ1 H chain constant region to produce anti-CD138 IgG1. To produce the fusion protein, the anti-CD138 $V_H$ was cloned into an expression vector containing the human γ1 H chain, a Gly-Ser linker (SGGGGS, SEQ ID NO:8), followed by human IFNα2. This expression vector was named pAH6905.

To construct the DNA vector for the expression of anti-CD138-IFNα2$^{YNS}$, nested PCR was used to introduce three amino acid mutations—H57Y, E58N, and Q61S. The first round of PCR was done using the forward primer 5'-CGC GGA TCC TGT GAT CTG CCT CAA ACC CAC-3' (SEQ ID NO:65) and reverse primer 5'-CCT CTA GAA TCA TTC CTT ACT TCT TAA ACT-3' (SEQ ID NO:66). The nested PCR was done using forward primer 5'-CTC TAC AAT ATG ATC TCA CAG ATC-3' (SEQ ID NO:67) and reverse primer 5'-GAT CTG TGA GAT CAT ATT GTA GAG-3' (SEQ ID NO:68), which contain the mutations to IFNα2. The insert was cloned into pCR2.1-TOPO vector (Invitrogen) and the DNA sequence was verified. The Xba I/BamH I fragment containing the mutant IFNα2$^{YNS}$ sequence was cloned into an intermediate human γ1 H chain vector and named pAH11015. The BamH I/Avr II fragment from pAH11015 containing the mutations to IFNα2 was then used to replace the wildtype IFNα2 sequence from expression vector pAH6905 (see above).

Protein Production and Purification

Fusion proteins were produced in CHO cells by transfection of H and L chain expression vectors. Stably transfected cells were selected with 1 mM histidinol. To produce IgG and fusion proteins, cells were seeded into roller bottles. At confluency, cells were expanded to 100 mL with IMDM+1% Fetal Clone (Thermo Fisher). The supernatant was removed every 2-3 days and replaced with fresh medium. Cell free culture supernatants were then passed through a protein A-Sepharose 4B fast flow column (Sigma) and the bound protein eluted with 0.1 M citric acid, pH 3.5. Eluted fractions were neutralized immediately with 2 M Tris-HCl pH 8.0. Fractions were run on SDS PAGE gels and stained with Coomassie blue to verify protein purity and integrity. Protein concentrations were determined using the BCA assay (Pierce). Anti-CD20-IFNα2, anti-CD20-IFNα2$^{YNS}$ and anti-dansyl (DNS)-IFNα2 used as untargeted control proteins were produced as described previously[12].

MTS Assay to Determine Metabolic Activity

HMCLs were seeded in 96-well plates and incubated with 0.00002 pM-25 nM of IFNα2, IFNβ, anti-CD138, anti-CD20-IFNα2, anti-CD20-IFNα2$^{YNS}$, anti-CD138-IFNα2 or anti-CD138-IFNα2$^{YNS}$ at 37° C. for 3, 4 or 7 days. Metabolic activity was determined using MTS solution (Promega) by measuring absorbance at 490 nm using a Synergy HT Multi-Detection Microplate Reader (BioTek Instruments Inc.) with untreated cells being 100%. GraphPad Prism (GraphPad Software Inc.) was used to analyze data by non-linear regression with the log (inhibitor) versus the response with a variable slope. Data are expressed as a percentage of maximum metabolic activity. The experiments were performed in triplicate.

Apoptosis Assay

Cells were incubated with 500 pM of IFNα2, anti-CD138-IFNα2 or anti-CD138-IFNα2$^{YNS}$ for 3 days at 37° C. Cells were stained with Alexa Fluor 488-labeled Annexin V and propidium iodide (PI) using the Vybrant Apoptosis Kit #2 (Molecular Probes) as per manufacturer's instructions and analyzed by flow cytometry.

Senescence Induced β-Galactosidase Activity

Intracellular β-galactosidase (β-gal) activity was measured as an indicator for replicative senescence. Cells were treated with 1 nM of anti-CD138, anti-CD138-IFNα2 or anti-CD138-IFNα2$^{YNS}$ for 3 days at 37° C. After treatment, cells were incubated with 100 nM bafilomycin A1 (Sigma) for 1 hour to induce lysosomal alkalinization. Then cells were incubated for 30 minutes with the 33 μM of β-gal substrate dodecanoylaminofluorescein di-β-D-galactopyranoside ($C_{12}$FDG; Invitrogen), which becomes fluorescent after cleavage to $C_{12}$-fluorescein. After washing twice with cold PBS, cells were resuspended in cold PBS containing 1 mM phenylethyl thiogalactoside (PETG), a β-gal inhibitor, and analyzed by flow cytometry for $C_{12}$-fluorescein.

Ki-67 Stain

Cells were treated with 500 pM of IFNα2, anti-CD138-IFNα2 or anti-CD138-IFNα2$^{YNS}$ for 3 days at 37° C. After treatment, cells were fixed with methanol on ice and then incubated with anti-Ki-67 rabbit IgG (Abcam). Cells were then stained with anti-rabbit IgG-FITC (Sigma) and analyzed by flow cytometry.

Western Blot Analysis of ppRb and IRF-4

Cells were treated for 48 hours with 1 nM IFNα2, anti-CD138, anti-CD138-IFNα2, or anti-CD138-IFNα2$^{YNS}$. Cells were lysed using RIPA buffer (50 mM Tris-HCl pH 8, 150 mM NaCl, 1% NP-40, 0.5% sodium deoxycholate, 0.1% SDS) containing a protease inhibitor cocktail (Roche Applied Science). The cytosolic fractions were reduced with β-mercaptoethanol and separated by SDS PAGE. Following transfer to nitrocellulose membrane (Whatman) and blocking, samples were incubated with the following primary rabbit antibodies: anti-IRF-4 (Epitomics), anti-glyceraldehyde-3-phosphate dehydrogenase (GAPDH; Sigma), or anti-ppRb Ser807/811 (Santa Cruz Biotechnology). Secondary anti-rabbit IgG-HRP (GE Healthcare) was used and the blots were developed using enhanced chemiluminescence (ECL; Thermo Scientific). Films were imaged using a MultiImage™ Light Cabinet (Alpha Innotech Corp.) and analyzed using NIH Image J. Bands were normalized to a GAPDH loading control and expressed as percentage band intensity of untreated cells.

Example 3

Additional Data

There are 12 different human IFNαs with different biologic activities (see, e.g., Lavoie et al. (2011) *Cytokine* 56: 82). We have now made an anti-CD138 fused to human IFNα14 (anti-CD138-IFNα14) and examined its activity. The anti-CD138 was fused to the INFα14 by a SGGGGS (SEQ ID NO:8) linker. The amino acid sequence of Human interferon alpha 14 (IFNα14) is given in UniProtKB/Swiss-Prot: P01570.3 as:

(SEQ ID NO: 69)
1 MALPFALMMA LVVLSCKSSC SLGCNLSQTH SLNNRRTLML MAQMRRISPF SCLKDRHDFE

61 FPQEEFDGNQ FQKAQAISVL HEMMQQTFNL FSTKNSSAAW DETLLEKFYI ELFQQMNDLE

121 ACVIQEVGVE ETPLMNEDSI LAVKKYFQRI TLYLMEKKYS PCAWEVVRAE IMRSLSFSTN

181 LQKRLRRKD

Figure 19:
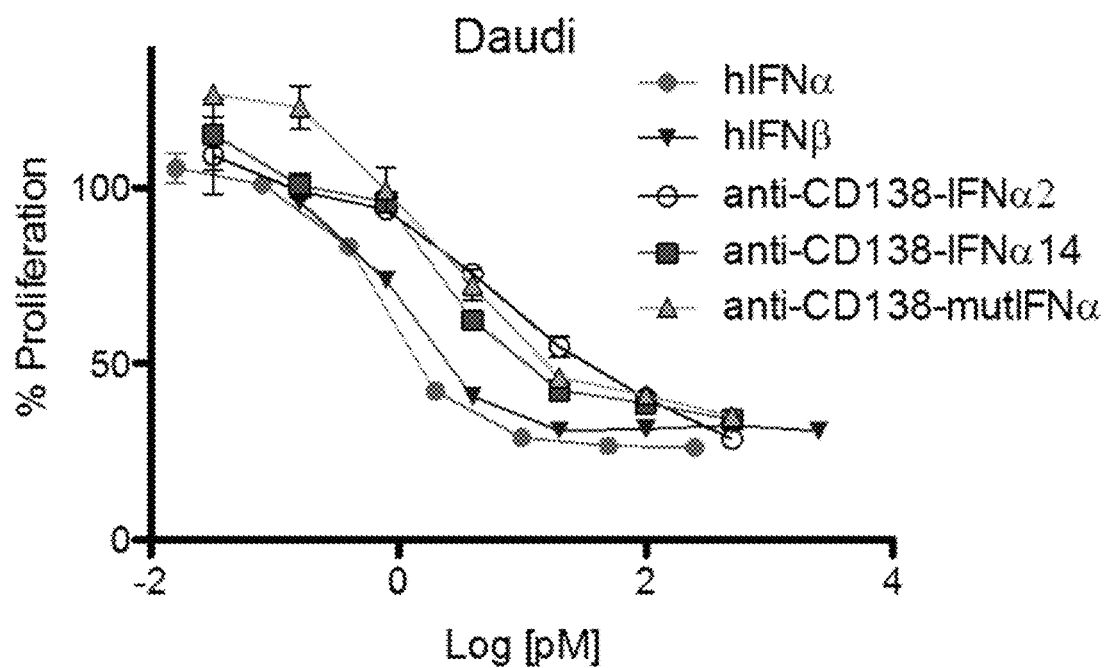
FIG. 19 shows the results of an MTS assay following 3 day incubation with the indicated proteins.

It is noted that MALPFALMMA LVVLSCKSSC SLG (SEQ ID NO:70) constitutes the hydrophobic leader sequence and was not included in the fusion protein FIG. 19 shows the results of an MTS assay following 3 day incubation with the indicated proteins. Daudi does not express CD138 and non-targeted anti-CD138-IFNα, anti-CD138-IFNα14 and anti-CD138-mutIFNα show similar activity.

Figure 20:
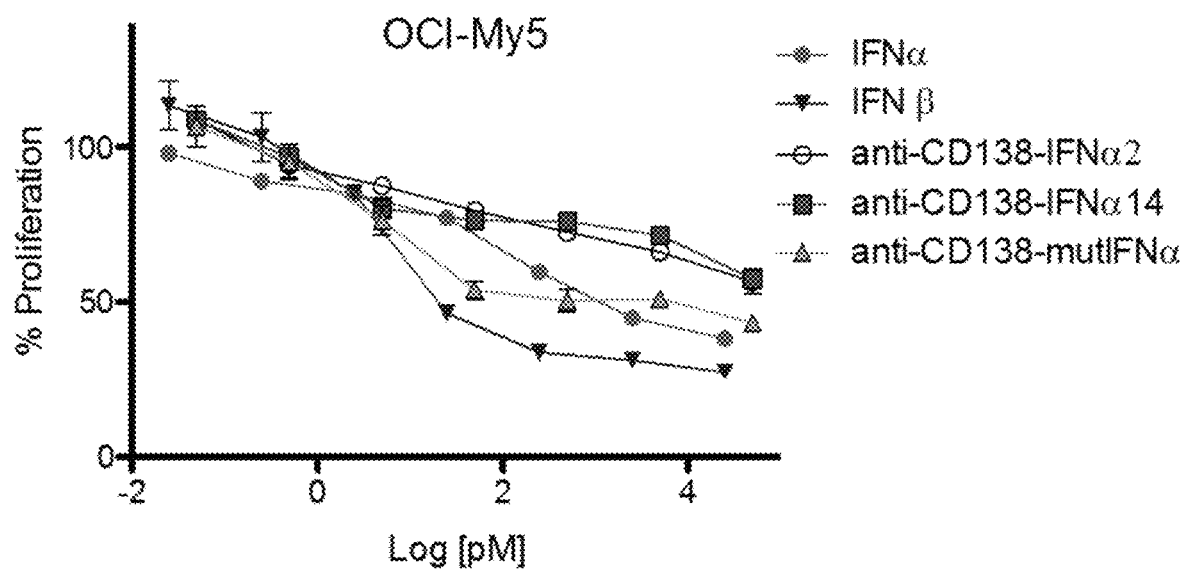
FIG. 20 shows the results of an MTS assay following 3 day incubation with the indicated proteins.

FIG. 20 shows the results of an MTS assay following 3 day incubation with the indicated proteins. Targeted anti-CD138-IFNα2 and anti-CD138-IFNα14 show similar activity against the OCI-My5 myeloma.

Figure 21:
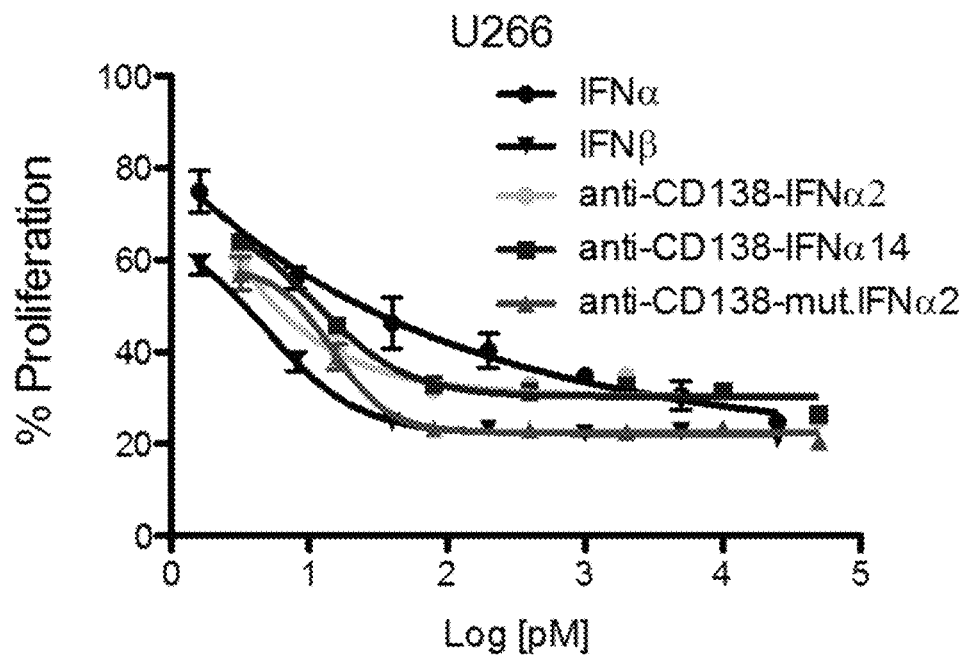
FIG. 21 shows the results of an MTS assay following 3 day incubation with the indicated proteins.

FIG. 21 shows the results of an MTS assay following 3 day incubation with the indicated proteins. Anti-CD138-IFNα2 and anti-CD138-IFNα14 show similar activity against U266.

Figure 22:
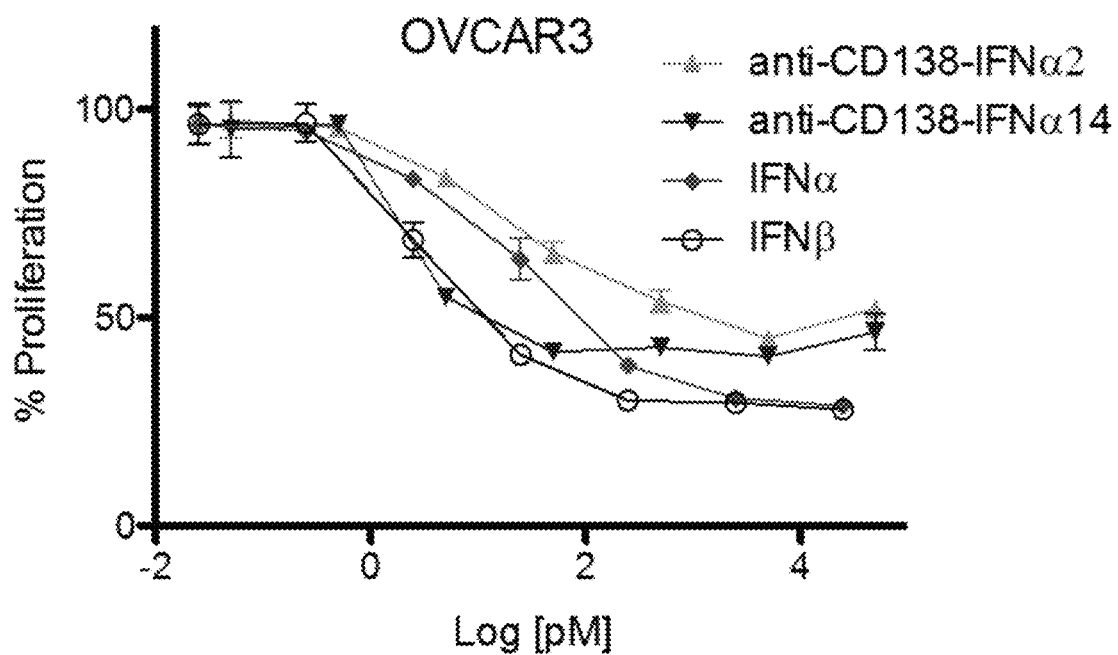
FIG. 22 shows the results of an MTS assay following 3 day incubation with the indicated proteins.

The ovarian cancer OVCAR3 expresses low levels of CD138. FIG. 22 shows that anti-CD138-IFNα14 is more effective than anti-CD138-IFNα2 against OVCAR3.

Figure 23:
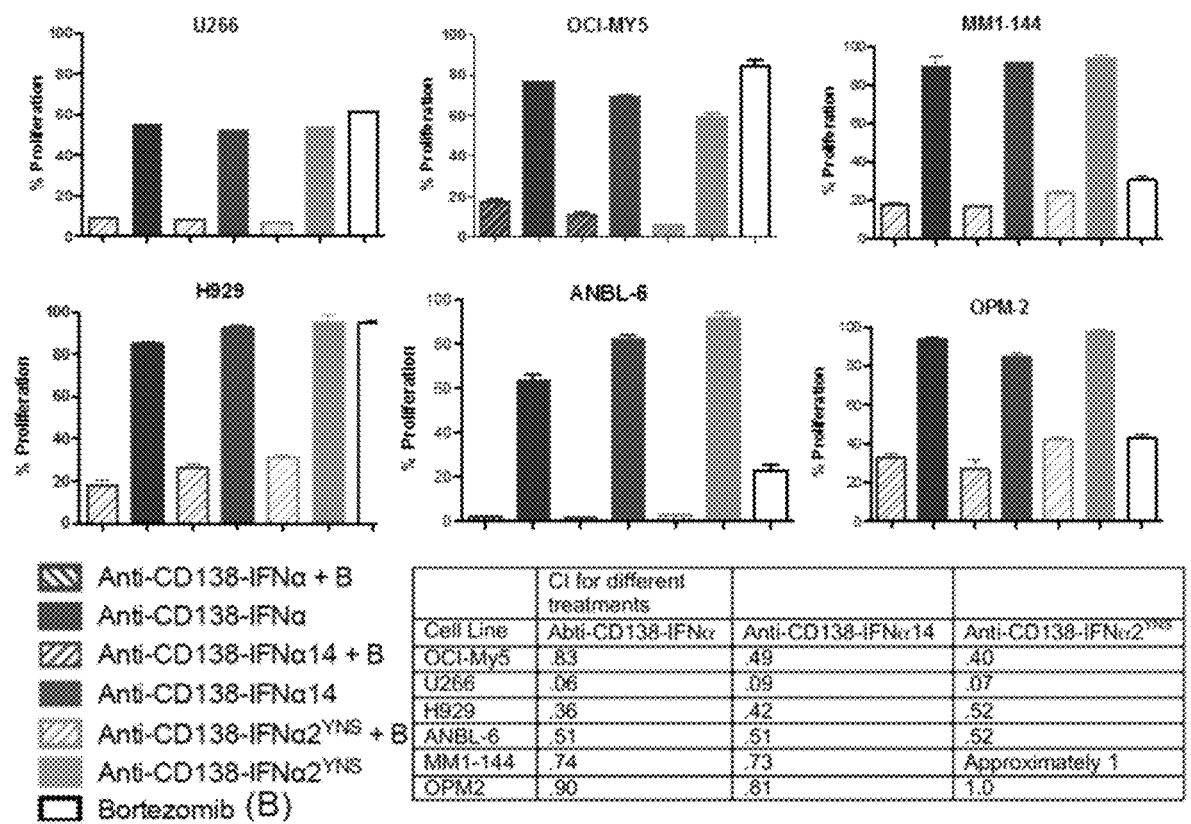
FIG. 23 shows the results of an MTS assay following various combination treatments.
Figure 24:
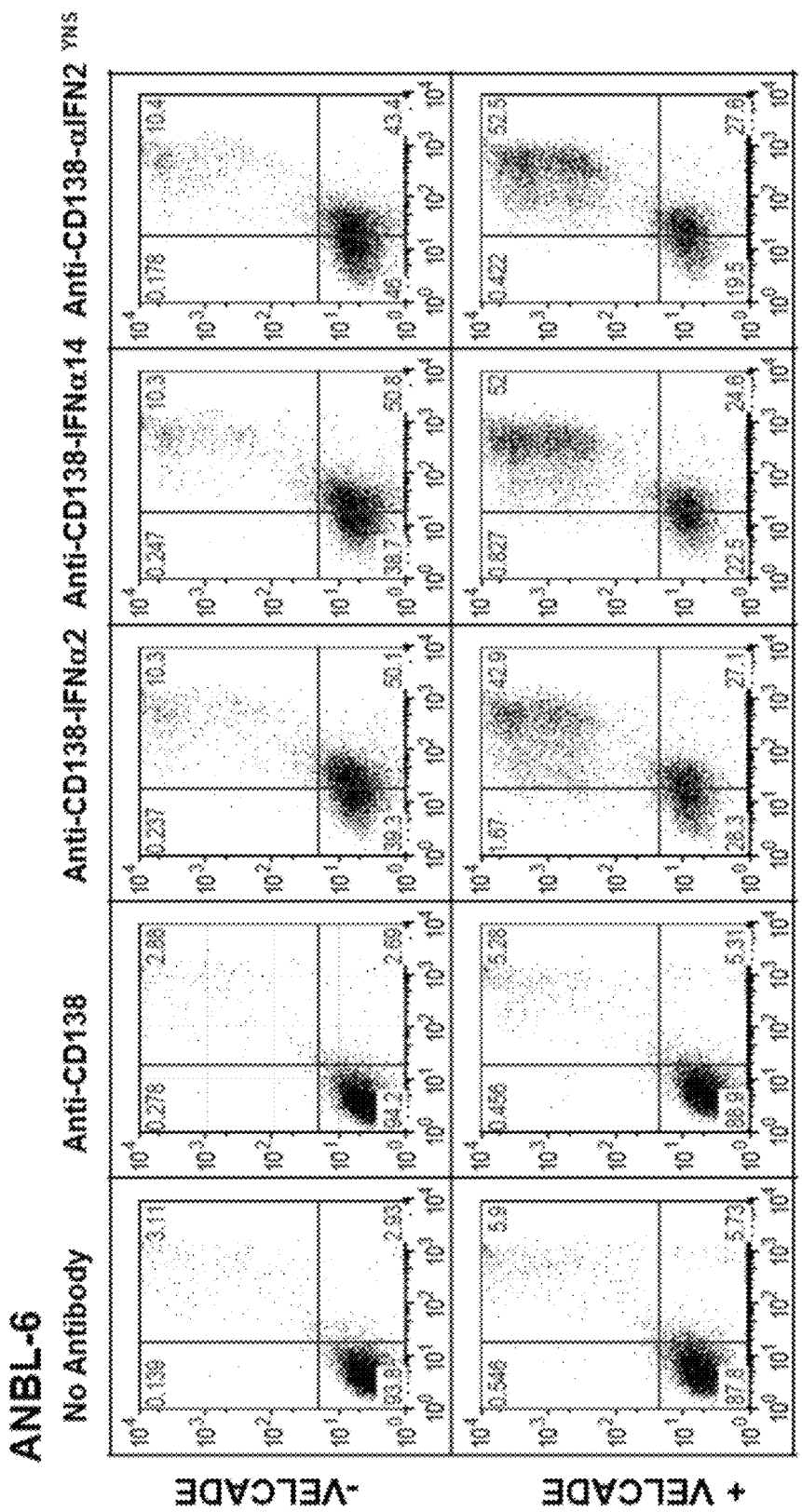
FIGS. 24-28 show flow cytometry results for apoptosis assays in various combination treatmetn using the IFN fusion proteins and VELCADE® as indicated.
Figure 25:
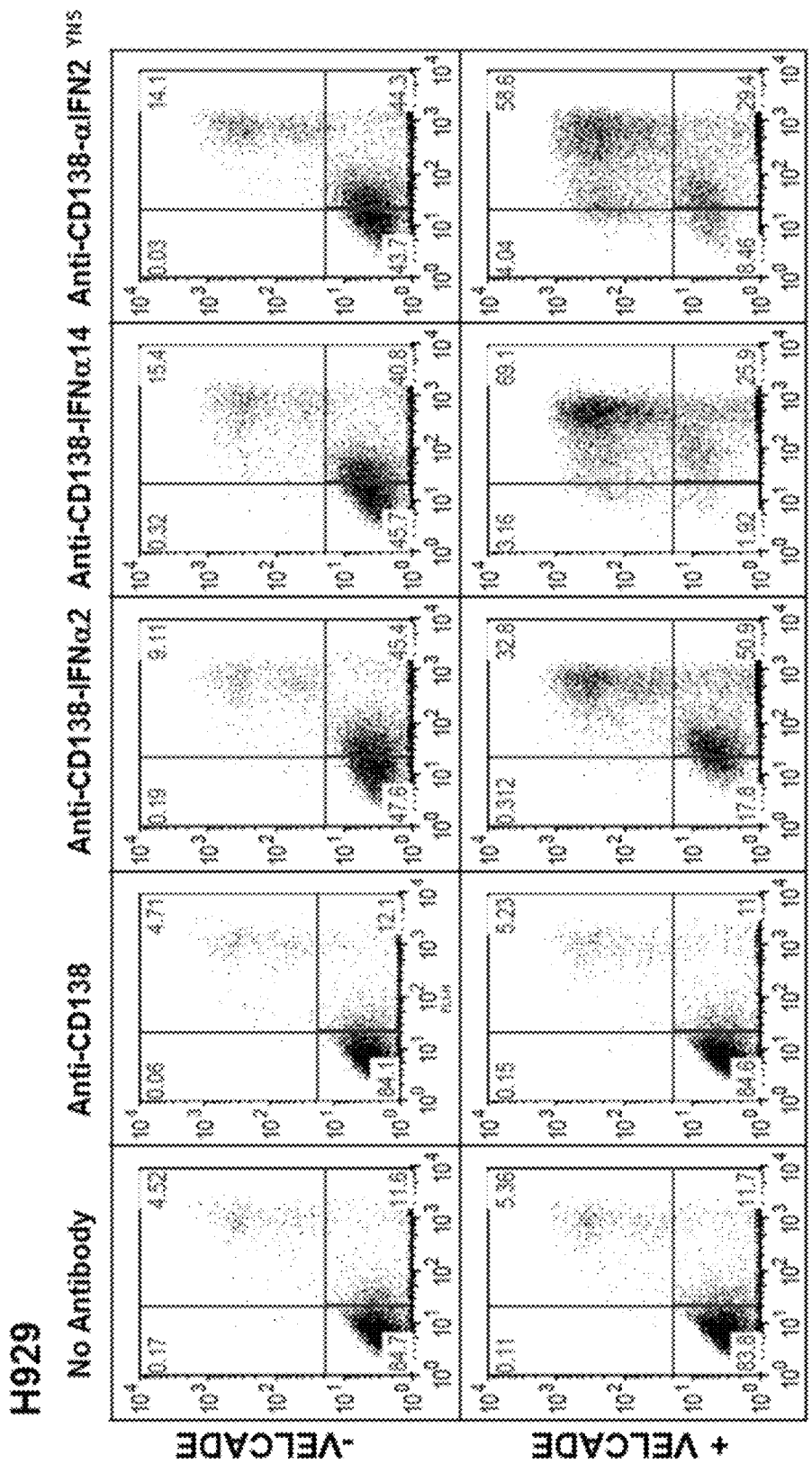
Figure 26:
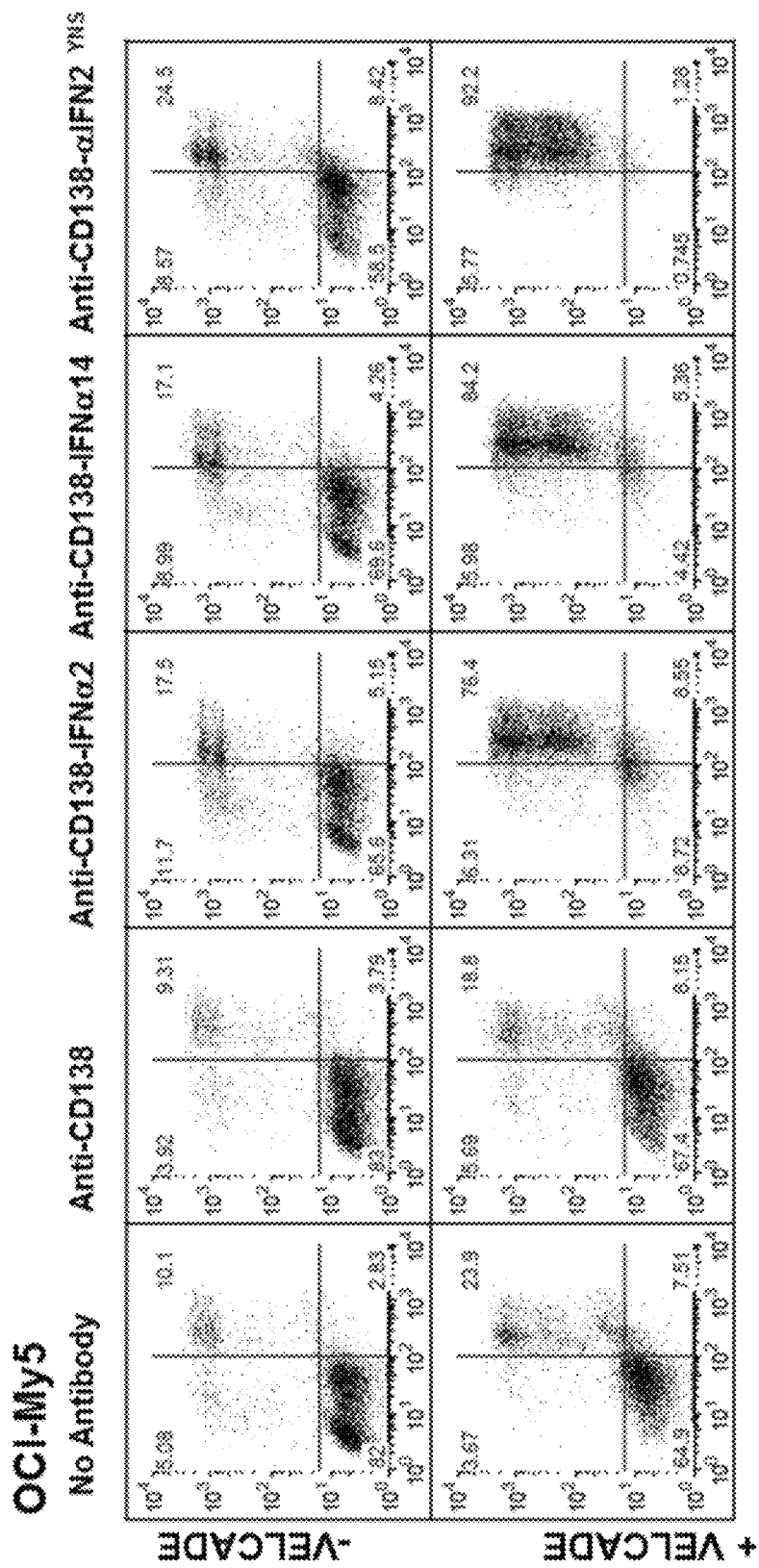
Figure 27:
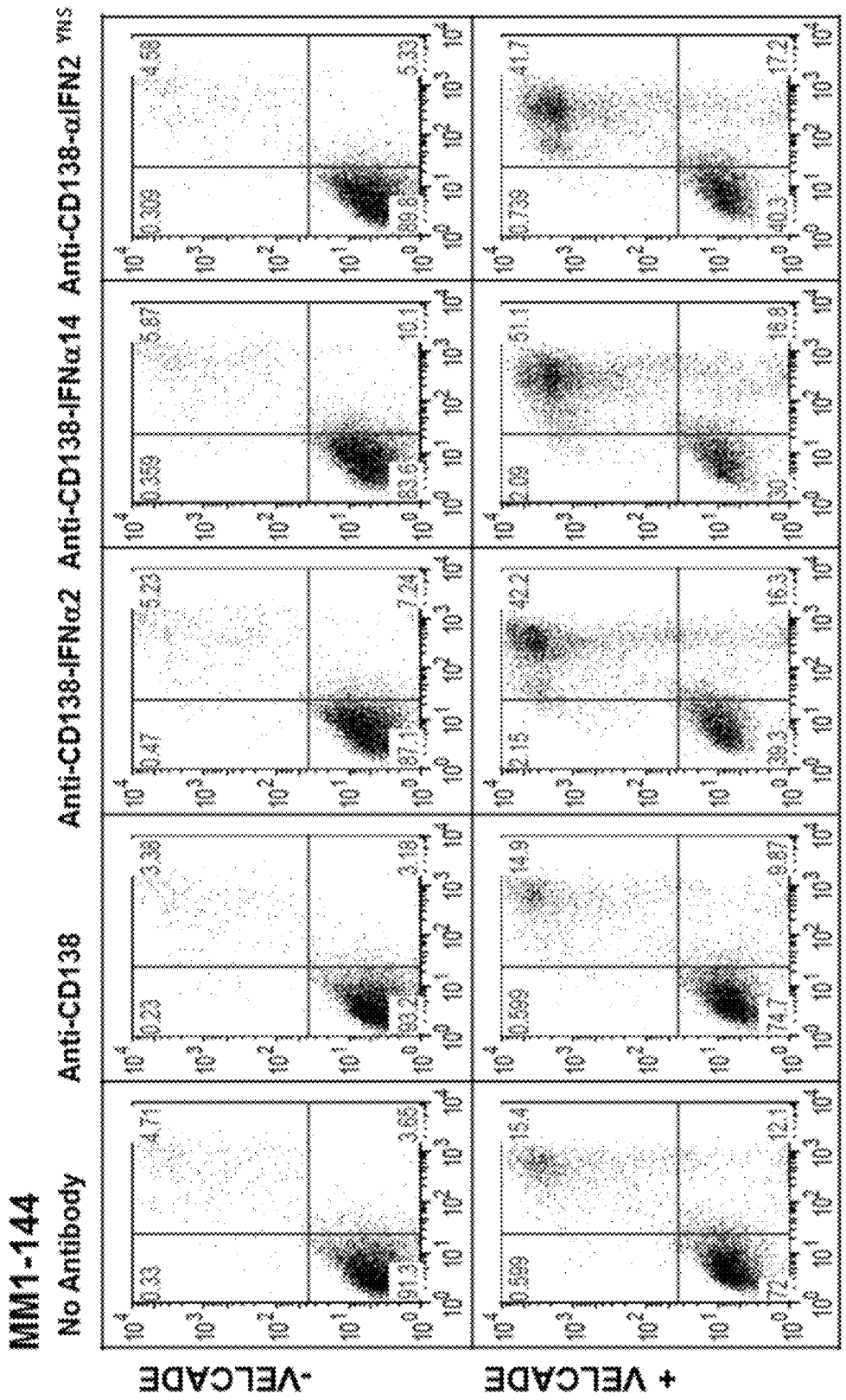
Figure 28:
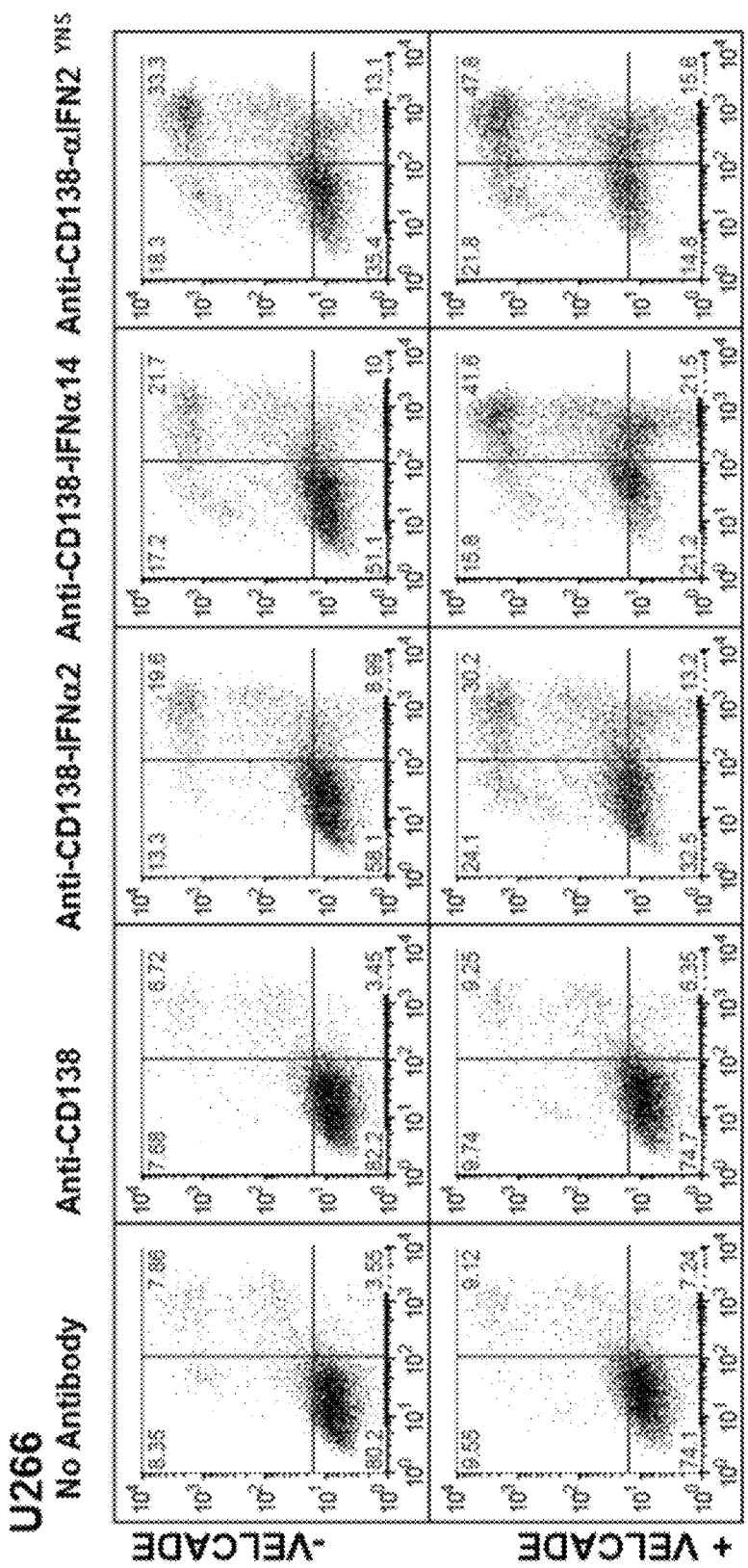

The proteasome inhibitor bortezomib (VELCADE® (bortezomib)) is an approved therapeutic for the treatment of myeloma. We tested for potential synergy of VELCADE® with anti-CD138 fusion proteins. FIG. 23: Cells were incubated with the indicated treatments for 3 days and then their proliferation measured using the MTS assay. For U266 VELCADE was used at 1.5 nM, anti-CD138-IFN$^{YNS}$ (a.k.a. anti-CD138-mutIFNα) at .5 pM and the other antibodies at 1.5 pM. For OCI-My5 VELCADE® was used at 1 nM and the antibodies at 1 pM. For the remaining cell lines, VELCADE was used at 5 nM and the antibodies at 5 pM. The Combination Index (CI) was calculated using Compusyn (see, e.g., Chou and Talalay, (1984) *Adv. Enz. Regul.* 22: 27-55). Values less than one indicate synergistic interactions; the smaller the number, the greater the synergy.

FIGS. 24-28: Cells were incubated with the indicated treatments for 3 days and then stained with Annexin V and PI and analyzed by flow cytometry. In all cases synergy is seen between VELCADE and the IFN fusion protein in the induction of apoptosis. ANBL-6 and MM1-144 were treated with 5 pM of antibody or antibody fusion protein and 4 nM VELCADE®. H929 was treated with 5 pM of antibody or antibody fusion protein and 5 nM VELCADE®. OCI-My5 was treated with 3 pM of antibody or antibody fusion protein and 3 nM VELCADE®. U266 was treated with 3 pM of antibody or antibody fusion protein and 1 nM VELCADE®.

Figure 29:
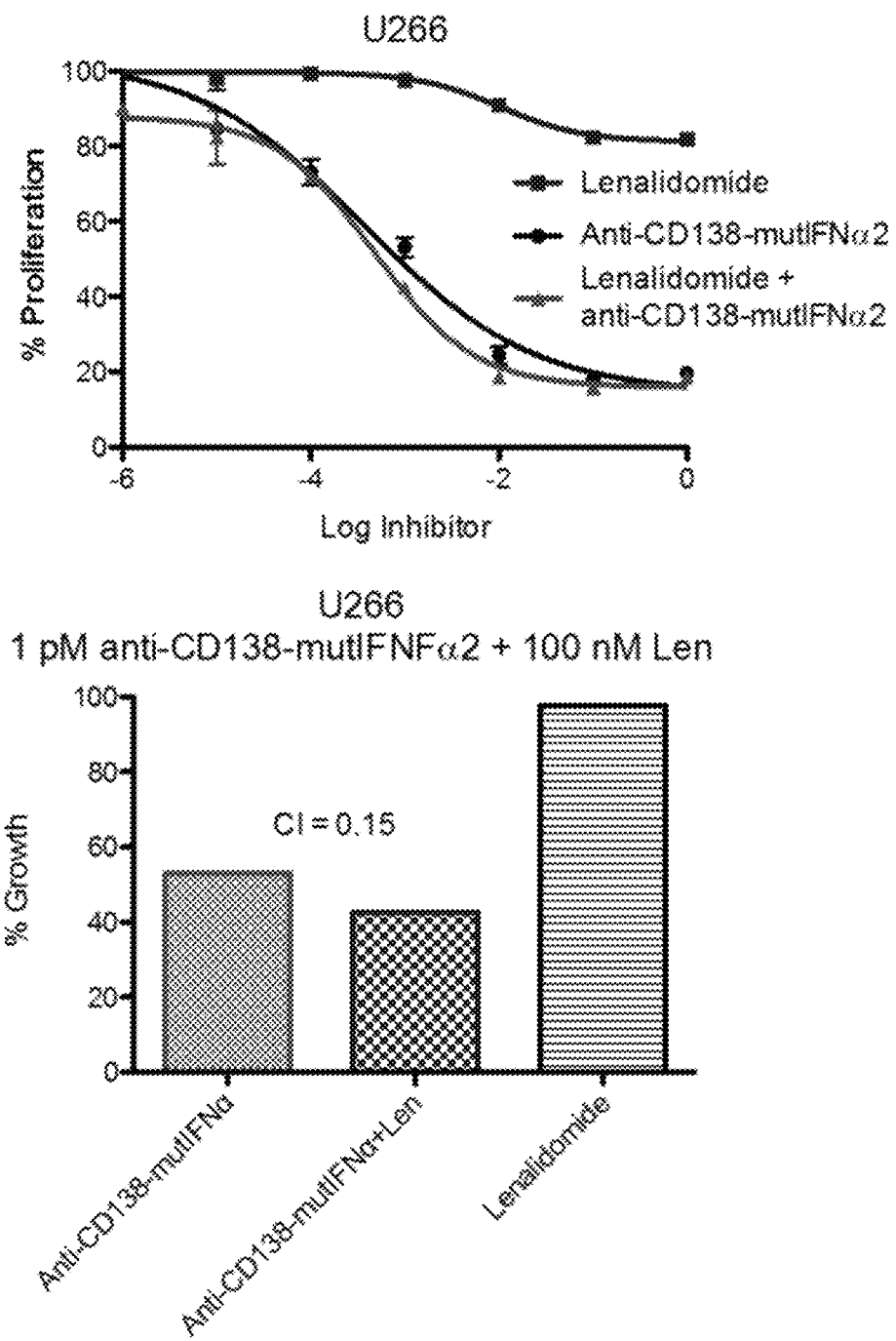
FIG. 29 illustrates a synergy between anti-CD138-mutIFNα and lenalidomide.

Lenalidomide, an analog of thalidomide, is FDA approved for the treatment of multiple myeloma. We also found evidence of synergy between anti-CD138-mutIFNα and lenalidomide (FIG. 29).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A chimeric construct comprising an interferon alpha, or a mutant interferon alpha comprising mutations H57Y, E58A, and Q61, attached by a proteolysis-resistant peptide linker that has a length shorter than 15 amino acids to a full-length antibody that binds CD138, where the amino acid sequence of said linker consists of the sequence SGGGGS (SEQ ID NO:8), and where said chimeric construct is effective to synergistically enhance the activity of lenalidomide in inducing apoptosis of cancer cells.

2. The construct of claim 1, wherein said construct, when contacted to a cell that expresses or overexpresses CD138, results in the killing or inhibition of growth or proliferation of said cell.

3. The construct of claim 2, wherein said cell that expresses or overexpresses CD138 is a cancer cell.

4. The construct of claim 2, wherein said cell that expresses or overexpresses CD138 is a cancer from a cancer selected from the group consisting of multiple myeloma, ovarian carcinoma, cervical cancer, endometrial cancer, kidney carcinoma, gall bladder carcinoma, transitional cell bladder carcinoma, gastric cancer, prostate adenocarcinoma, breast cancer, prostate cancer, lung cancer, colon cancer, Hodgkin's and non-Hodgkin's lymphoma, chronic lymphocytic leukemia (CLL), acute lymphoblastic leukemia (ALL), acute myeloblastic leukemia (AML), a solid tissue sarcoma, colon carcinoma, non-small cell lung carcinoma, squamous cell lung carcinoma, colorectal carcinoma, hepato-carcinoma, pancreatic cancer, and head and neck carcinoma.

5. The construct of claim 1, wherein said interferon is an interferon-alpha (IFN-α).

6. The construct of claim 5, wherein said interferon is an interferon alpha 2 (IFNα2).

7. The construct of claim 5, wherein said interferon is an interferon alpha 14 (IFNα14).

8. The construct of claim 1, wherein said interferon is a mutant interferon alpha comprising mutations H57Y, E58A, and Q61S.

9. The construct of claim 1, wherein said antibody comprises the complementarity determining regions of the B-B4 monoclonal antibody.

10. The construct of claim 9, wherein said antibody comprises the VH and/or VL domain of the B-B4 monoclonal antibody.

11. The construct of claim 10, wherein said antibody is the B-B4 monoclonal antibody.

12. A pharmaceutical formulation comprising a construct of claim 1 in a pharmaceutically acceptable excipient.

13. The formulation of claim 12, wherein said formulation further comprises bortezomib and/or lenalidomide.

* * * * *

SEQUENCE LISTING

```
<160> NUMBER OF SEQ ID NOS: 70

<210> SEQ ID NO 1
<211> LENGTH: 15
<212> TYPE: PRT
<213> ORGANISM: Artificial
<220> FEATURE:
<223> OTHER INFORMATION: Peptide linker

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 5
<212> TYPE: PRT
<213> ORGANISM: Artificial
<220> FEATURE:
<223> OTHER INFORMATION: Peptide linker.

<400> SEQUENCE: 2

Gly Gly Gly Gly Ser
1               5

<210> SEQ ID NO 3
<211> LENGTH: 184
<212> TYPE: PRT
<213> ORGANISM: Artificial
<220> FEATURE:
<223> OTHER INFORMATION: Truncated interferon beta

<400> SEQUENCE: 3

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Gln Thr
                20                  25                  30

His Ser Leu Gly Ser Arg Arg Thr Leu Met Leu Leu Ala Gln Met Arg
            35                  40                  45

Arg Ile Ser Leu Phe Ser Cys Leu Lys Asp Arg His Asp Phe Gly Phe
        50                  55                  60
```

-continued

```
Pro Gln Glu Glu Phe Gly Asn Gln Phe Gln Lys Ala Glu Thr Ile Pro
 65                  70                  75                  80

Val Leu His Glu Met Ile Gln Gln Ile Phe Asn Leu Phe Ser Thr Lys
                 85                  90                  95

Asp Ser Ser Ala Ala Trp Asp Glu Thr Leu Leu Asp Lys Phe Tyr Thr
            100                 105                 110

Glu Leu Tyr Gln Gln Leu Asn Asp Leu Glu Ala Cys Val Ile Gln Gly
        115                 120                 125

Val Gly Val Thr Glu Thr Pro Leu Met Lys Glu Asp Ser Ile Leu Ala
130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn Leu Gln
            180
```

<210> SEQ ID NO 4
<211> LENGTH: 183
<212> TYPE: PRT
<213> ORGANISM: Artificial
<220> FEATURE:
<223> OTHER INFORMATION: Truncated interferon beta

<400> SEQUENCE: 4

```
Met Gly Lys Met Ala Ser Leu Phe Ala Thr Phe Leu Val Val Leu Val
 1               5                  10                  15

Ser Leu Ser Leu Ala Ser Glu Ser Ala Cys Asp Leu Pro Gln Thr
             20                  25                  30

His Ser Leu Gly Ser Arg Arg Thr Leu Met Leu Leu Ala Gln Met Arg
         35                  40                  45

Arg Ile Ser Leu Phe Ser Cys Leu Lys Asp Arg His Asp Phe Gly Phe
     50                  55                  60

Pro Gln Glu Glu Phe Gly Asn Gln Phe Gln Lys Ala Glu Thr Ile Pro
 65                  70                  75                  80

Val Leu His Glu Met Ile Gln Gln Ile Phe Asn Leu Phe Ser Thr Lys
                 85                  90                  95

Asp Ser Ser Ala Ala Trp Asp Glu Thr Leu Leu Asp Lys Phe Tyr Thr
            100                 105                 110

Glu Leu Tyr Gln Gln Leu Asn Asp Leu Glu Ala Cys Val Ile Gln Gly
        115                 120                 125

Val Gly Val Thr Glu Thr Pro Leu Met Lys Glu Asp Ser Ile Leu Ala
130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn Leu
            180
```

<210> SEQ ID NO 5
<211> LENGTH: 182
<212> TYPE: PRT
<213> ORGANISM: Artificial
<220> FEATURE:
<223> OTHER INFORMATION: Truncated interferon beta

<400> SEQUENCE: 5

Met Gly Lys Met Ala Ser Leu Phe Ala Thr Phe Leu Val Leu Val
1               5                   10                  15

Ser Leu Ser Leu Ala Ser Glu Ser Ser Ala Cys Asp Leu Pro Gln Thr
            20                  25                  30

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
            85                  90                  95

Asp Ser Ser Ala Ala Trp Asp Glu Thr Leu Leu Asp Lys Phe Tyr Thr
            100                 105                 110

Glu Leu Tyr Gln Gln Leu Asn Asp Leu Glu Ala Cys Val Ile Gln Gly
        115                 120                 125

Val Gly Val Thr Glu Thr Pro Leu Met Lys Glu Asp Ser Ile Leu Ala
    130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
            165                 170                 175

Phe Ser Leu Ser Thr Asn
            180

<210> SEQ ID NO 6
<211> LENGTH: 15
<212> TYPE: PRT
<213> ORGANISM: Artificial
<220> FEATURE:
<223> OTHER INFORMATION: Peptide linker.

<400> SEQUENCE: 6

Gly Gly Gly Gly Ser Gly Gly Gly Ser Gly Gly Gly Ser
1               5                   10                  15

<210> SEQ ID NO 7
<211> LENGTH: 5
<212> TYPE: PRT
<213> ORGANISM: Artificial
<220> FEATURE:
<223> OTHER INFORMATION: Peptide linker.

<400> SEQUENCE: 7

Gly Gly Gly Gly Ser
1               5

<210> SEQ ID NO 8
<211> LENGTH: 6
<212> TYPE: PRT
<213> ORGANISM: Artificial
<220> FEATURE:
<223> OTHER INFORMATION: Peptide linker.

<400> SEQUENCE: 8

Ser Gly Gly Gly Gly Ser
1               5

<210> SEQ ID NO 9
<211> LENGTH: 10

```
<212> TYPE: PRT
<213> ORGANISM: Artificial
<220> FEATURE:
<223> OTHER INFORMATION: Peptide linker.

<400> SEQUENCE: 9

Gly Gly Gly Gly Ser Gly Gly Gly Gly Ser
1               5                   10

<210> SEQ ID NO 10
<211> LENGTH: 7
<212> TYPE: PRT
<213> ORGANISM: Artificial
<220> FEATURE:
<223> OTHER INFORMATION: Peptide linker.

<400> SEQUENCE: 10

Ala Glu Ala Ala Ala Lys Ala
1               5

<210> SEQ ID NO 11
<211> LENGTH: 12
<212> TYPE: PRT
<213> ORGANISM: Artificial
<220> FEATURE:
<223> OTHER INFORMATION: Peptide linker.

<400> SEQUENCE: 11

Ala Glu Ala Ala Ala Lys Glu Ala Ala Ala Lys Ala
1               5                   10

<210> SEQ ID NO 12
<211> LENGTH: 17
<212> TYPE: PRT
<213> ORGANISM: Artificial
<220> FEATURE:
<223> OTHER INFORMATION: Peptide linker.

<400> SEQUENCE: 12

Ala Glu Ala Ala Ala Lys Glu Ala Ala Ala Lys Glu Ala Ala Ala Lys
1               5                   10                  15

Ala

<210> SEQ ID NO 13
<211> LENGTH: 22
<212> TYPE: PRT
<213> ORGANISM: Artificial
<220> FEATURE:
<223> OTHER INFORMATION: Peptide linker.

<400> SEQUENCE: 13

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 14
<211> LENGTH: 27
<212> TYPE: PRT
<213> ORGANISM: Artificial
<220> FEATURE:
<223> OTHER INFORMATION: Peptide linker.

<400> SEQUENCE: 14

Ala Glu Ala Ala Ala Lys Glu Ala Ala Ala Lys Glu Ala Ala Ala Lys
1               5                   10                  15
```

Glu Ala Ala Ala Lys Glu Ala Ala Lys Ala
            20                  25

<210> SEQ ID NO 15
<211> LENGTH: 13
<212> TYPE: PRT
<213> ORGANISM: Artificial
<220> FEATURE:
<223> OTHER INFORMATION: Peptide linker.

<400> SEQUENCE: 15

Ala Glu Ala Ala Ala Lys Glu Ala Ala Ala Lys Ala Gly
1               5                   10

<210> SEQ ID NO 16
<211> LENGTH: 14
<212> TYPE: PRT
<213> ORGANISM: Artificial
<220> FEATURE:
<223> OTHER INFORMATION: Peptide linker.

<400> SEQUENCE: 16

Ala Glu Ala Ala Ala Lys Glu Ala Ala Ala Lys Ala Gly Ser
1               5                   10

<210> SEQ ID NO 17
<211> LENGTH: 5
<212> TYPE: PRT
<213> ORGANISM: Artificial
<220> FEATURE:
<223> OTHER INFORMATION: Peptide linker.

<400> SEQUENCE: 17

Gly Gly Gly Gly Gly
1               5

<210> SEQ ID NO 18
<211> LENGTH: 5
<212> TYPE: PRT
<213> ORGANISM: Artificial
<220> FEATURE:
<223> OTHER INFORMATION: Peptide linker.

<400> SEQUENCE: 18

Gly Gly Ala Gly Gly
1               5

<210> SEQ ID NO 19
<211> LENGTH: 8
<212> TYPE: PRT
<213> ORGANISM: Artificial
<220> FEATURE:
<223> OTHER INFORMATION: Peptide linker.

<400> SEQUENCE: 19

Gly Gly Gly Gly Gly Gly Gly Gly
1               5

<210> SEQ ID NO 20
<211> LENGTH: 10
<212> TYPE: PRT
<213> ORGANISM: Artificial
<220> FEATURE:
<223> OTHER INFORMATION: Peptide linker.

<400> SEQUENCE: 20

Gly Ala Gly Ala Gly Ala Gly Ala Gly Ala
1               5                   10

<210> SEQ ID NO 21
<211> LENGTH: 18
<212> TYPE: PRT
<213> ORGANISM: Artificial
<220> FEATURE:
<223> OTHER INFORMATION: Peptide linker.

<400> SEQUENCE: 21

Arg Pro Leu Ser Tyr Arg Pro Pro Phe Pro Phe Gly Phe Pro Ser Val
1               5                   10                  15

Arg Pro

<210> SEQ ID NO 22
<211> LENGTH: 18
<212> TYPE: PRT
<213> ORGANISM: Artificial
<220> FEATURE:
<223> OTHER INFORMATION: Peptide linker.

<400> SEQUENCE: 22

Tyr Pro Arg Ser Ile Tyr Ile Arg Arg His Pro Ser Pro Ser Leu
1               5                   10                  15

Thr Thr

<210> SEQ ID NO 23
<211> LENGTH: 18
<212> TYPE: PRT
<213> ORGANISM: Artificial
<220> FEATURE:
<223> OTHER INFORMATION: Peptide linker.

<400> SEQUENCE: 23

Thr Pro Ser His Leu Ser His Ile Leu Pro Ser Phe Gly Leu Pro Thr
1               5                   10                  15

Phe Asn

<210> SEQ ID NO 24
<211> LENGTH: 18
<212> TYPE: PRT
<213> ORGANISM: Artificial
<220> FEATURE:
<223> OTHER INFORMATION: Peptide linker.

<400> SEQUENCE: 24

Arg Pro Val Ser Pro Phe Thr Phe Pro Arg Leu Ser Asn Ser Trp Leu
1               5                   10                  15

Pro Ala

<210> SEQ ID NO 25
<211> LENGTH: 18
<212> TYPE: PRT
<213> ORGANISM: Artificial
<220> FEATURE:
<223> OTHER INFORMATION: Peptide linker.

<400> SEQUENCE: 25

Ser Pro Ala Ala His Phe Pro Arg Ser Ile Pro Arg Pro Gly Pro Ile
1               5                   10                  15

Arg Thr

```
<210> SEQ ID NO 26
<211> LENGTH: 18
<212> TYPE: PRT
<213> ORGANISM: Artificial
<220> FEATURE:
<223> OTHER INFORMATION: Peptide linker.

<400> SEQUENCE: 26

Ala Pro Gly Pro Ser Ala Pro Ser His Arg Ser Leu Pro Ser Arg Ala
1               5                   10                  15

Phe Gly

<210> SEQ ID NO 27
<211> LENGTH: 18
<212> TYPE: PRT
<213> ORGANISM: Artificial
<220> FEATURE:
<223> OTHER INFORMATION: Peptide linker.

<400> SEQUENCE: 27

Pro Arg Asn Ser Ile His Phe Leu His Pro Leu Leu Val Ala Pro Leu
1               5                   10                  15

Gly Ala

<210> SEQ ID NO 28
<211> LENGTH: 18
<212> TYPE: PRT
<213> ORGANISM: Artificial
<220> FEATURE:
<223> OTHER INFORMATION: Peptide linker.

<400> SEQUENCE: 28

Met Pro Ser Leu Ser Gly Val Leu Gln Val Arg Tyr Leu Ser Pro Pro
1               5                   10                  15

Asp Leu

<210> SEQ ID NO 29
<211> LENGTH: 18
<212> TYPE: PRT
<213> ORGANISM: Artificial
<220> FEATURE:
<223> OTHER INFORMATION: Peptide linker.

<400> SEQUENCE: 29

Ser Pro Gln Tyr Pro Ser Pro Leu Thr Leu Thr Leu Pro Pro His Pro
1               5                   10                  15

Ser Leu

<210> SEQ ID NO 30
<211> LENGTH: 18
<212> TYPE: PRT
<213> ORGANISM: Artificial
<220> FEATURE:
<223> OTHER INFORMATION: Peptide linker.

<400> SEQUENCE: 30

Asn Pro Ser Leu Asn Pro Pro Ser Tyr Leu His Arg Ala Pro Ser Arg
1               5                   10                  15

Ile Ser

<210> SEQ ID NO 31
<211> LENGTH: 17
<212> TYPE: PRT
<213> ORGANISM: Artificial
```

```
<220> FEATURE:
<223> OTHER INFORMATION: Peptide linker.

<400> SEQUENCE: 31

Leu Pro Trp Arg Thr Ser Leu Leu Pro Ser Leu Pro Leu Arg Arg
1               5                   10                  15

Pro

<210> SEQ ID NO 32
<211> LENGTH: 18
<212> TYPE: PRT
<213> ORGANISM: Artificial
<220> FEATURE:
<223> OTHER INFORMATION: Peptide linker.

<400> SEQUENCE: 32

Pro Pro Leu Phe Ala Lys Gly Pro Val Gly Leu Leu Ser Arg Ser Phe
1               5                   10                  15

Pro Pro

<210> SEQ ID NO 33
<211> LENGTH: 18
<212> TYPE: PRT
<213> ORGANISM: Artificial
<220> FEATURE:
<223> OTHER INFORMATION: Peptide linker.

<400> SEQUENCE: 33

Val Pro Pro Ala Pro Val Val Ser Leu Arg Ser Ala His Ala Arg Pro
1               5                   10                  15

Pro Tyr

<210> SEQ ID NO 34
<211> LENGTH: 17
<212> TYPE: PRT
<213> ORGANISM: Artificial
<220> FEATURE:
<223> OTHER INFORMATION: Peptide linker.

<400> SEQUENCE: 34

Leu Arg Pro Thr Pro Pro Arg Val Arg Ser Tyr Thr Cys Cys Pro Thr
1               5                   10                  15

Pro

<210> SEQ ID NO 35
<211> LENGTH: 18
<212> TYPE: PRT
<213> ORGANISM: Artificial
<220> FEATURE:
<223> OTHER INFORMATION: Peptide linker.

<400> SEQUENCE: 35

Pro Asn Val Ala His Val Leu Pro Leu Leu Thr Val Pro Trp Asp Asn
1               5                   10                  15

Leu Arg

<210> SEQ ID NO 36
<211> LENGTH: 18
<212> TYPE: PRT
<213> ORGANISM: Artificial
<220> FEATURE:
<223> OTHER INFORMATION: Peptide linker.

<400> SEQUENCE: 36
```

Cys Asn Pro Leu Leu Pro Leu Cys Ala Arg Ser Pro Ala Val Arg Thr
1               5                   10                  15

Phe Pro

<210> SEQ ID NO 37
<211> LENGTH: 14
<212> TYPE: PRT
<213> ORGANISM: Artificial
<220> FEATURE:
<223> OTHER INFORMATION: Peptide linker.

<400> SEQUENCE: 37

Leu Gly Thr Pro Thr Pro Thr Pro Thr Pro Thr Gly Glu Phe
1               5                   10

<210> SEQ ID NO 38
<211> LENGTH: 8
<212> TYPE: PRT
<213> ORGANISM: Artificial
<220> FEATURE:
<223> OTHER INFORMATION: Peptide linker.

<400> SEQUENCE: 38

Glu Asp Phe Thr Arg Gly Lys Leu
1               5

<210> SEQ ID NO 39
<211> LENGTH: 21
<212> TYPE: PRT
<213> ORGANISM: Artificial
<220> FEATURE:
<223> OTHER INFORMATION: Peptide linker.

<400> SEQUENCE: 39

Leu Glu Ala Ala Ala Arg Glu Ala Ala Ala Arg Glu Ala Ala Ala Arg
1               5                   10                  15

Glu Ala Ala Ala Arg
                20

<210> SEQ ID NO 40
<211> LENGTH: 16
<212> TYPE: PRT
<213> ORGANISM: Artificial
<220> FEATURE:
<223> OTHER INFORMATION: Peptide linker.

<400> SEQUENCE: 40

Leu Glu Ala Ala Ala Arg Glu Ala Ala Ala Arg Glu Ala Ala Ala Arg
1               5                   10                  15

<210> SEQ ID NO 41
<211> LENGTH: 11
<212> TYPE: PRT
<213> ORGANISM: Artificial
<220> FEATURE:
<223> OTHER INFORMATION: Peptide linker.

<400> SEQUENCE: 41

Leu Glu Ala Ala Ala Arg Glu Ala Ala Ala Arg
1               5                   10

<210> SEQ ID NO 42
<211> LENGTH: 6
<212> TYPE: PRT
<213> ORGANISM: Artificial

```
<220> FEATURE:
<223> OTHER INFORMATION: Peptide linker.

<400> SEQUENCE: 42

Leu Glu Ala Ala Ala Arg
1               5

<210> SEQ ID NO 43
<211> LENGTH: 20
<212> TYPE: PRT
<213> ORGANISM: Artificial
<220> FEATURE:
<223> OTHER INFORMATION: Peptide linker.

<400> SEQUENCE: 43

Glu Ala Ala Ala Arg Glu Ala Ala Ala Arg Glu Ala Ala Ala Arg Glu
1               5                   10                  15

Ala Ala Ala Arg
            20

<210> SEQ ID NO 44
<211> LENGTH: 15
<212> TYPE: PRT
<213> ORGANISM: Artificial
<220> FEATURE:
<223> OTHER INFORMATION: Peptide linker.

<400> SEQUENCE: 44

Glu Ala Ala Ala Arg Glu Ala Ala Ala Arg Glu Ala Ala Ala Arg
1               5                   10                  15

<210> SEQ ID NO 45
<211> LENGTH: 10
<212> TYPE: PRT
<213> ORGANISM: Artificial
<220> FEATURE:
<223> OTHER INFORMATION: Peptide linker.

<400> SEQUENCE: 45

Glu Ala Ala Ala Arg Glu Ala Ala Ala Arg
1               5                   10

<210> SEQ ID NO 46
<211> LENGTH: 5
<212> TYPE: PRT
<213> ORGANISM: Artificial
<220> FEATURE:
<223> OTHER INFORMATION: Peptide linker.

<400> SEQUENCE: 46

Glu Ala Ala Ala Arg
1               5

<210> SEQ ID NO 47
<211> LENGTH: 19
<212> TYPE: PRT
<213> ORGANISM: Artificial
<220> FEATURE:
<223> OTHER INFORMATION: Signal peptide

<400> SEQUENCE: 47

Met Gly Trp Ser Tyr Ile Ile Leu Phe Leu Val Ala Thr Ala Thr Gly
1               5                   10                  15

Val His Ser
```

-continued

```
<210> SEQ ID NO 48
<211> LENGTH: 20
<212> TYPE: PRT
<213> ORGANISM: Artificial
<220> FEATURE:
<223> OTHER INFORMATION: Signal peptide

<400> SEQUENCE: 48

Met Lys Ser Gln Thr Gln Val Phe Ile Phe Leu Leu Leu Cys Val Ser
1               5                   10                  15

Gly Ala His Gly
            20

<210> SEQ ID NO 49
<211> LENGTH: 11
<212> TYPE: DNA
<213> ORGANISM: Artificial
<220> FEATURE:
<223> OTHER INFORMATION: Kozak ribosomal recognition site

<400> SEQUENCE: 49
ggatatccac c                                                            11

<210> SEQ ID NO 50
<211> LENGTH: 7
<212> TYPE: DNA
<213> ORGANISM: Artificial
<220> FEATURE:
<223> OTHER INFORMATION: Cloning nucleic acic spacer

<400> SEQUENCE: 50 gctagcc                                                                 7

<210> SEQ ID NO 51
<211> LENGTH: 12
<212> TYPE: DNA
<213> ORGANISM: Artificial
<220> FEATURE:
<223> OTHER INFORMATION: Cloning nucleic acic spacer

<400> SEQUENCE: 51
cgtaagtcga cg                                                           12

<210> SEQ ID NO 52
<211> LENGTH: 141
<212> TYPE: PRT
<213> ORGANISM: Artificial
<220> FEATURE:
<223> OTHER INFORMATION: Antibody VH sequence

<400> SEQUENCE: 52

Met Gly Trp Ser Tyr Ile Ile Leu Phe Leu Val Ala Thr Ala Thr Gly
1               5                   10                  15

Val His Ser Gln Val Gln Leu Gln Gln Ser Gly Ser Glu Leu Met Met
            20                  25                  30

Pro Gly Ala Ser Val Lys Ile Ser Cys Lys Ala Thr Gly Tyr Thr Phe
        35                  40                  45

Ser Asn Tyr Trp Ile Glu Trp Val Lys Gln Arg Pro Gly His Gly Leu
    50                  55                  60

Glu Trp Ile Gly Glu Ile Leu Pro Gly Thr Gly Arg Thr Ile Tyr Asn
65                  70                  75                  80

Glu Lys Phe Lys Gly Lys Ala Thr Phe Thr Ala Asp Ile Ser Ser Asn
                85                  90                  95
```

```
Thr Val Gln Met Gln Leu Ser Ser Leu Thr Ser Glu Asp Ser Ala Val
            100                 105                 110

Tyr Tyr Cys Ala Arg Arg Asp Tyr Tyr Gly Asn Phe Tyr Tyr Ala Met
        115                 120                 125

Asp Tyr Trp Gly Gln Gly Thr Ser Val Thr Val Ser Ser
    130                 135                 140

<210> SEQ ID NO 53
<211> LENGTH: 127
<212> TYPE: PRT
<213> ORGANISM: Artificial
<220> FEATURE:
<223> OTHER INFORMATION: Antibody VLsequence

<400> SEQUENCE: 53

Met Lys Ser Gln Thr Gln Val Phe Ile Phe Leu Leu Leu Cys Val Ser
1               5                   10                  15

Gly Ala His Gly Asp Ile Gln Met Thr Gln Ser Thr Ser Ser Leu Ser
            20                  25                  30

Ala Ser Leu Gly Asp Arg Val Thr Ile Ser Cys Ser Ala Ser Gln Gly
        35                  40                  45

Ile Asn Asn Tyr Leu Asn Trp Tyr Gln Gln Lys Pro Asp Gly Thr Val
    50                  55                  60

Glu Leu Leu Ile Tyr Tyr Thr Ser Thr Leu Gln Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Gly Thr Tyr Tyr Cys Gln Gln Tyr Ser
            100                 105                 110

Lys Leu Pro Arg Thr Phe Gly Gly Gly Thr Lys Leu Glu Ile Lys
        115                 120                 125

<210> SEQ ID NO 54
<211> LENGTH: 30
<212> TYPE: DNA
<213> ORGANISM: Artificial
<220> FEATURE:
<223> OTHER INFORMATION: PCR primer

<400> SEQUENCE: 54
cgcggatcct gtgatctgcc tcaaacccac                                    30

<210> SEQ ID NO 55
<211> LENGTH: 30
<212> TYPE: DNA
<213> ORGANISM: Artificial
<220> FEATURE:
<223> OTHER INFORMATION: PCR primer

<400> SEQUENCE: 55
cctctagaat cattccttac ttcttaaact                                    30

<210> SEQ ID NO 56
<211> LENGTH: 33
<212> TYPE: DNA
<213> ORGANISM: Artificial
<220> FEATURE:
<223> OTHER INFORMATION: PCR primer

<400> SEQUENCE: 56
cctgtcctct acaatatgat ctcacagatc ttc                                33
```

<210> SEQ ID NO 57
<211> LENGTH: 33
<212> TYPE: DNA
<213> ORGANISM: Artificial
<220> FEATURE:
<223> OTHER INFORMATION: PCR primer

<400> SEQUENCE: 57
gaagatctgt gagatcatat tgtagaggac agg         33

<210> SEQ ID NO 58
<211> LENGTH: 137
<212> TYPE: PRT
<213> ORGANISM: Artificial
<220> FEATURE:
<223> OTHER INFORMATION: Antibody VH domain

<400> SEQUENCE: 58

Met Gly Trp Ser Tyr Ile Ile Leu Phe Leu Val Ala Thr Ala Thr Gly
1               5                   10                  15

Val His Ser Gln Val Gln Leu Gln Gln Ser Gly Ser Glu Leu Met Met
            20                  25                  30

Pro Gly Ala Ser Val Lys Ile Ser Cys Lys Ala Thr Gly Tyr Thr Phe
        35                  40                  45

Ser Asn Tyr Trp Ile Gln Arg Pro His Gly Leu Glu Trp Ile Gly
    50                  55                  60

Glu Ile Leu Pro Gly Thr Gly Arg Thr Ile Tyr Asn Glu Lys Phe Lys
65                  70                  75                  80

Gly Lys Ala Thr Phe Thr Ala Asp Ile Ser Ser Asn Thr Val Gln Met
                85                  90                  95

Gln Leu Ser Ser Leu Thr Ser Glu Asp Ser Ala Val Tyr Tyr Cys Ala
            100                 105                 110

Arg Arg Asp Tyr Tyr Gly Asn Phe Tyr Tyr Ala Met Asp Tyr Trp Gly
        115                 120                 125

Gln Gly Thr Ser Val Thr Val Ser Ser
    130                 135

<210> SEQ ID NO 59
<211> LENGTH: 127
<212> TYPE: PRT
<213> ORGANISM: Artificial
<220> FEATURE:
<223> OTHER INFORMATION: Antibody VL domain

<400> SEQUENCE: 59

Met Lys Ser Gln Thr Gln Val Phe Ile Phe Leu Leu Leu Cys Val Ser
1               5                   10                  15

Gly Ala His Gly Asp Ile Gln Met Thr Gln Ser Thr Ser Ser Leu Ser
            20                  25                  30

Ala Ser Leu Gly Asp Arg Val Thr Ile Ser Cys Ser Ala Ser Gln Gly
        35                  40                  45

Ile Asn Asn Tyr Leu Asn Trp Tyr Gln Gln Lys Pro Asp Gly Thr Val
    50                  55                  60

Glu Leu Leu Ile Tyr Tyr Thr Ser Thr Leu Gln Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Glu Asp Ile Gly Thr Tyr Tyr Cys Gln Gln Tyr Ser
            100                 105                 110

```
Lys Leu Pro Arg Thr Phe Gly Gly Gly Thr Lys Leu Glu Ile Lys
        115                 120                 125

<210> SEQ ID NO 60
<211> LENGTH: 19
<212> TYPE: PRT
<213> ORGANISM: Artificial
<220> FEATURE:
<223> OTHER INFORMATION: Signal peptide

<400> SEQUENCE: 60

Met Gly Trp Ser Tyr Ile Ile Leu Phe Leu Val Ala Thr Ala Thr Gly
1               5                   10                  15

Val His Ser

<210> SEQ ID NO 61
<211> LENGTH: 20
<212> TYPE: PRT
<213> ORGANISM: Artificial
<220> FEATURE:
<223> OTHER INFORMATION: Signal peptide

<400> SEQUENCE: 61

Met Lys Ser Gln Thr Gln Val Phe Ile Phe Leu Leu Leu Cys Val Ser
1               5                   10                  15

Gly Ala His Gly
            20

<210> SEQ ID NO 62
<211> LENGTH: 11
<212> TYPE: DNA
<213> ORGANISM: Artificial
<220> FEATURE:
<223> OTHER INFORMATION: Kozak ribosomal recognition site

<400> SEQUENCE: 62
ggatatccac c                                                          11

<210> SEQ ID NO 63
<211> LENGTH: 7
<212> TYPE: DNA
<213> ORGANISM: Artificial
<220> FEATURE:
<223> OTHER INFORMATION: Nucleic acid cloning spacer

<400> SEQUENCE: 63 gctagcc                                                                7

<210> SEQ ID NO 64
<211> LENGTH: 12
<212> TYPE: DNA
<213> ORGANISM: Artificial
<220> FEATURE:
<223> OTHER INFORMATION: Nucleic acid cloning spacer

<400> SEQUENCE: 64
cgtaagtcga cg                                                         12

<210> SEQ ID NO 65
<211> LENGTH: 30
<212> TYPE: DNA
<213> ORGANISM: Artificial
<220> FEATURE:
<223> OTHER INFORMATION: PCR primer
```

-continued

<400> SEQUENCE: 65
cgcggatcct gtgatctgcc tcaaacccac                                30

<210> SEQ ID NO 66
<211> LENGTH: 30
<212> TYPE: DNA
<213> ORGANISM: Artificial
<220> FEATURE:
<223> OTHER INFORMATION: PCR primer

<400> SEQUENCE: 66
cctctagaat cattccttac ttcttaaact                                30

<210> SEQ ID NO 67
<211> LENGTH: 24
<212> TYPE: DNA
<213> ORGANISM: Artificial
<220> FEATURE:
<223> OTHER INFORMATION: PCR primer

<400> SEQUENCE: 67
ctctacaata tgatctcaca gatc                                      24

<210> SEQ ID NO 68
<211> LENGTH: 24
<212> TYPE: DNA
<213> ORGANISM: Artificial
<220> FEATURE:
<223> OTHER INFORMATION: PCR primer

<400> SEQUENCE: 68
gatctgtgag atcatattgt agag                                      24

<210> SEQ ID NO 69
<211> LENGTH: 189
<212> TYPE: PRT
<213> ORGANISM: Homo sapiens

<400> SEQUENCE: 69

Met Ala Leu Pro Phe Ala Leu Met Met Ala Leu Val Val Leu Ser Cys
1               5                   10                  15

Lys Ser Ser Cys Ser Leu Gly Cys Asn Leu Ser Gln Thr His Ser Leu
            20                  25                  30

Asn Asn Arg Arg Thr Leu Met Leu Met Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Gln Glu Val Gly
        115                 120                 125

Val Glu Glu Thr Pro Leu Met Asn Glu Asp Ser Ile Leu Ala Val Lys
    130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser

```
                   165                 170                 175
Phe Ser Thr Asn Leu Gln Lys Arg Leu Arg Arg Lys Asp
            180                 185

<210> SEQ ID NO 70
<211> LENGTH: 23
<212> TYPE: PRT
<213> ORGANISM: Artificial
<220> FEATURE:
<223> OTHER INFORMATION: Hydrophobic leader peptide

<400> SEQUENCE: 70

Met Ala Leu Pro Phe Ala Leu Met Met Ala Leu Val Val Leu Ser Cys
1               5                   10                  15

Lys Ser Ser Cys Ser Leu Gly
            20
```